US008883841B2

(12) United States Patent
Fang et al.

(10) Patent No.: US 8,883,841 B2
(45) Date of Patent: Nov. 11, 2014

(54) ONCOGENIC RAS-SPECIFIC CYTOTOXIC COMPOUND AND METHODS OF USE THEREOF

(75) Inventors: Bingliang Fang, Pearland, TX (US); Jinsong Liu, Houston, TX (US); Wei Guo, Houston, TX (US); Shuhong Wu, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1469 days.

(21) Appl. No.: 12/094,739

(22) PCT Filed: Nov. 22, 2006

(86) PCT No.: PCT/US2006/061219
§ 371 (c)(1),
(2), (4) Date: Oct. 20, 2008

(87) PCT Pub. No.: WO2007/062399
PCT Pub. Date: May 31, 2007

(65) Prior Publication Data
US 2009/0286847 A1    Nov. 19, 2009

Related U.S. Application Data

(60) Provisional application No. 60/739,856, filed on Nov. 23, 2005.

(51) Int. Cl.
*A61K 31/404*    (2006.01)

(52) U.S. Cl.
CPC .................................. *A61K 31/404* (2013.01)
USPC ........................................................ 514/415

(58) Field of Classification Search
None
See application file for complete search history.

(56) References Cited

U.S. PATENT DOCUMENTS

| | | | | |
|---|---|---|---|---|
| 6,610,722 | B2 | 8/2003 | Stump et al. | 514/397 |
| 6,900,043 | B1 | 5/2005 | Belmont et al. | 435/196 |
| 7,371,875 | B2 | 5/2008 | Xiao et al. | 549/510 |
| 2001/0007877 | A1 | 7/2001 | Burton et al. | |
| 2003/0087902 | A1 | 5/2003 | Stolle et al. | |
| 2004/0138255 | A1 | 7/2004 | Huang et al. | 514/311 |

FOREIGN PATENT DOCUMENTS

| | | |
|---|---|---|
| CN | 1505613 A | 6/2004 |
| EP | 1 484 329 | 12/2004 |
| WO | WO 95/22524 | 8/1995 |
| WO | WO 01/64639 | 9/2001 |
| WO | WO 2004/108702 | 12/2004 |

OTHER PUBLICATIONS

Sausville et al. Cancer Research, 2006, vol. 66, pp. 3351-3354.*
Johnson et al. British J. of Cancer, 2001, 84(10):1424-1431.*
European Supplementary Search Report, issued in European Application No. 06840010.0-2112, dated Feb. 18, 2010.
Andreani et al., "Potential antitumor agents XIII: Indole derivatives related to lonidamine," *Arch. Pharm.*, 317:847-51, 1984.
Andreani et al., "Synthesis and anti-inflammatory activity of indole carboxylic acids and esters," *Acta. Pharm. Nord.*, 3:5-8, 1991.
Bacher et al., "D-24851, a novel synthetic microtubule inhibitor, exerts curative antitumoral activity in vivo, shows efficacy toward multidrug-resistant tumor cells, and lacks neurotoxicity," *Cancer Research*, 61:392-99, 2001.
Na et al., "Synthesis and antifungal activity of new 1-halogenobenzyl-3-imidazolylmethlindole derivatives," *Eur. J. Med. Chem.*, 38:75-87, 2003.
Akoulitchev et al., "TFIIH is negatively regulated by cdk8-containing mediator complexes," *Nature*, 407:102-106, 2000.
Alessi et al., "3-Phosphoinositide-dependent protein kinase-I (PDK I): structural and functional homology with the *Drosophila* DSTPK61 kinase," *Current Biology*, 7:776-789, 1997.
Allen and Chonn, "Large unilamellar liposomes with low uptake into the reticuloendothelial system," *FEBS Lett.*, 223:42-46, 1987.
Allen et al., "A new strategy for attachment of antibodies to sterically stablized liposomes resulting in efficient targeting to cancer cells," *Bichimica et Biophysica Acta*, 1237:99-108, 1995.
Archambault et al., "An essential component of a C-terminal domain phosphatase that interacts with transcription factor IIF in *Saccharomyces cerevisiae*," *Proc. Natl. Acad. Sci. USA*, 94:14300-14305, 1997.
Barnes and Karin, "Nuclear factor-kappaB: a pivotal transcription factor in chronic inflammatory diseases," *NE J. Medicine*, 336:1066-1071, 1997.
Baskaran et al., "Identification of a binding site in c-Abl tyrosine kinase for the C-terminal repeated domain of RNA polymerase II," *Molec. Cell. Biol.*, 16:3361-3369, 1996.
Baskaran et al., "Tyrosine phosphorylation of mammalian RNA polymerase II carboxyl-terminal domain," *Proc. Natl. Acad. Sci. USA*, 90:11167-11171, 1993.
Baum and Kirschmeier, "Preclinical and clinical evaluation of farnesyltransferase inhibitors," *Current Oncology Reports*, 5:99-107, 2003.
Baumann et al., "Human Rad51 protein promotes ATP-dependent homologous pairing and strand transfer reactions in vitro," *Cell*, 87:757-766, 1996.
Benson et al., "Purification and characterization of the human Rad51 protein, an analogue of *E. coli* RecA," *EMBO J.*, 13:5764-5771, 1994.
Bergo et al., "Inactivation of Icmt inhibits transformation by oncogenic K-Ras and B-Raf," *J. Clinical Investigation*, 113:539-550, 2004.
Bernards and Settleman, "GAP control: regulating the regulators of small GTPases," *Trends in Cell Biology*, 14:377-385, 2004.
Bernhard et al., "Direct evidence for the contribution of activated N-ras and K-ras oncogenes to increased intrinsic radiation resistance in human tumor cell lines," *Cancer Res.*, 60:6597-6600, 2000.
Berra et al., "Protein kinase C zeta isoform is critical for mitogenic signal transduction," *Cell*, 74:555-563, 1993.
Blume and Cevc, "Molecular mechanism of the lipid vesicle longevity in vito," *Biochim. Biophys. Acta.*, 1146:157-68, 1993.

(Continued)

*Primary Examiner* — James D Anderson
(74) *Attorney, Agent, or Firm* — Parker Highlander PLLC

(57) ABSTRACT

Embodiments of the present invention provide for methods and compositions comprising an Oncorasin, such as 1-[(4-chlorophenyl)methyl]-1H-Indole-3-carboxaldehyde (oncrasin-1) and/or its analogs or derivatives.

52 Claims, 25 Drawing Sheets

(56) References Cited

OTHER PUBLICATIONS

Bonnet et al., "Transcription-independent phosphorylation of the RNA polymerase II C-terminal domain (CTD) involves ERK kinases (MEK1/2).," *Nucleic Acids Research*, 27:4399-4404, 1999.
Bos et al., "Prevalence of ras gene mutations in human colorectal cancers," *Nature*, 327:293-297, 1987.
Bos, "ras oncogenes in human cancer: a review," *Cancer Res.*, 49:4682-9, 1989.
Brignall, "Prevention and treatment of cancer with indole-3-carbinol," *Alternative Medicine Review*, 6:580-589, 2001.
Cadwallader et al., "N-terminally myristoylated Ras proteins require palmitoylation or a polybasic domain for plasma membrane localization," *Molecular and Cellular Biology*, 14:4722-4730, 1994.
Carmo-Fonseca et al., "Transcription-dependent colocalization of the U1, U2, U4/U6, and U5 snRNPs in coiled bodies," *J. Cell Biology*, 117:1-14, 1992.
Chinni et al., "Indole-3-carbinol (I3C) induced cell growth inhibition, G1 cell cycle arrest and apoptosis in prostate cancer cells," *Oncogene*, 20:2927-2936, 2001.
Chodosh et al., "5,6-Dichloro-1-beta-D-ribofuranosylbenzimidazole inhibits transcription elongation by RNA polymerase II in vitro," *J. Biol. Chem.*, 264:2250-2257, 1989.
Coleman et al., "Overexpression of c-K-ras, c-N-ras and transforming growth factor beta co-segregate with tumorigenicity in morphologically transformed C3H 10T1/2 cell lines," *Carcinogenesis*, 15:1005-12, 1994.
Colicelli, "Human RAS superfamily proteins and related GTPases," *Science's STKE*, 1-31, 2004.
Colwill et al., "The Clk/Sty protein kinase phosphorylates SR splicing factors and regulates their intranuclear distribution," *EMBO J.*, 15:265-275, 1996.
Couvreur et al., "Nanocapsules: a new type of lysosomotropic carrier," *FEBS Lett.*, 84:323-326, 1977.
Critchfield et al., "Casein kinase II is a selective target of HIV-1 transcriptional inhibitors," *Proc. Natl. Acad. Sci. USA*, 94:6110-6115, 1997.
Cujec et al., "The HIV transactivator TAT binds to the CDK-activating kinase and activates the phosphorylation of the carboxy-terminal domain of RNA polymerase II," *Genes and Development*, 11:2645-2657, 1997.
Dancey, "Agents targeting Ras signaling pathway," *Current Pharmaceutical Design*, 8:2259-2267, 2002.
Davies et al., "Mutations of the BRAF gene in human cancer," *Nature*, 417:949-954, 2002.
Diaz-Meco et al., "Evidence for the in vitro and in vivo interaction of Ras with protein kinase C zeta," *J. Biol. Chem.*, 269:31706-31710, 1994.
Eder et al., "Atypical PKCiota contributes to poor prognosis through loss of apical-basal polarity and cyclin E overexpression in ovarian cancer," *Proc. Natl. Acad. Sci. USA*, 102:12519-12524, 2005.
Ehrhardt et al., "Distinct mechanisms determine the patterns of differential activation of H-Ras, N-Ras, K-Ras 4B, and M-Ras by receptors for growth factors or antigen," *Molecular and Cellular Biology*, 24:6311-6323, 2004.
Fakan and Nobis, "Ultrastructural localization of transcription sites and of RNA distribution during the cell cycle of synchronized CHO cells," *Experimental Cell Research*, 113:327-337, 1978.
Fedorov et al., "Atypical protein kinase Cs are the Ras effectors that mediate repression of myogenic satellite cell differentiation," *Molecular and Cellular Biology*, 22:1140-1149, 2002.
Filmus and Buick, "Stability of c-K-ras amplification during progression in a patient with adenocarcinoma of the ovary," *Cancer Res.*, 45:4468-4471, 1985.
Fiorucci and Hall, "All three human ras genes are expressed in a wide range of tissues," *Biochima. Biophysica. Acta.*, 950:81-83, 1988.
Fisher, "Apoptosis in cancer therapy: crossing the threshold," *Cell*, 78:539-42, 1994.
Fraley et al., "Entrapment of a bacterial plasmid in phospholipid vesicles: potential for gene transfer," *Proc. Natl. Acad. Sci. USA*, 76:3348-3352, 1979.
Fu and Maniatis, "Isolation of a complementary DNA that encodes the mammalian splicing factor SC35," *Science*, 256:535-538, 1992.
Fukuhara et al., "Utilization of host SR protein kinases and RNA-splicing machinery during viral replication," *Proc. Natl. Acad. Sci. USA*, 103:11329-11333, 2006.
Gabizon and Paphadjopoulos, "Liposome formulations with prolonged circulation time in blood and enhanced uptake by tumors," *Proc. Natl. Acad. Sci. USA*, 85:6949-6953, 1988.
Galiana et al., "High frequency of Ki-ras amplification and p53 gene mutations in adenocarcinomas of the human esophagus," *Molecular Carcinogenesis*, 14:286-293, 1995.
Garnett and Marais, "Guilty as charged: B-RAF is a human oncogene," *Cancer Cell*, 6:313-319, 2004.
Gu et al., "Tumor-specific transgene expression from the human telomerase reverse transcriptase promoter enables targeting of the therapeutic effects of the Bax gene to cancers," *Cancer Res.*, 60:5359-5364, 2000.
Gu et al., "hTERT promoter induces tumor-specific Bax gene expression and cell killing in syngenic mouse tumor model and prevents systemic toxicity," *Gene Ther.*, 9:30-37, 2002.
Guerrero et al., "K-ras codon 12 mutation induces higher level of resistance to apoptosis and predisposition to anchorage-independent growth than codon 13 mutation or proto-oncogene overexpression," *Cancer Res.*, 60:6750-6756, 2000.
Hancock et al., "A polybasic domain or palmitoylation is required in addition to the CAAX motif to localize p21ras to the plasma membrane," *Cell*, 63:133-139, 1990.
Hancock, "Ras proteins: different signals from different locations," *Nature Review Molecular Cell Biology*, 4:373-384, 2003.
Heath, "Covalent attachment of proteins to liposomes," *Methods in Enzymology*, 149:111-118, 1987.
Hengartner et al., "Temporal regulation of RNA polymerase II by Srb10 and Kin28 cyclin-dependent kinases," *Molecular Cell*, 2:43-53, 1998.
Hoa et al., "Amplification of wild-type K-ras promotes growth of head and neck squamous cell carcinoma," *Cancer Res.*, 62:7154-7156, 2002.
James et al., "Polylysine and CVIM sequences of K-RasB dictate specificity of prenylation and confer resistance to benzodiazepine peptidomimetic in vitro," *Biological Chemistry*, 270:6221-6226, 1995.
James et al., "Resistance of K-RasBV12 proteins to farnesyltransferase inhibitors in Rat1 cells," *Proc. Natl. Acad. Sci. USA*, 93:4454-4458, 1996.
Jun et al., "Tangled webs: evidence of cross-talk between c-raf-1 and Akt," Science's *STKE* [Electronice Resources]: Signal Transduction Knowledge Environment, E1, 1999.
Kamenski et al., "Structure and mechanism of RNA polymerase II CTD phosphatases," *Molecular Cell*, 15:399-407, 2004.
Kaelin, "The concept of synthetic lethality in the context of anticancer therapy," *Nature Reviews*, 5:689-698, 2005.
Karin and Ben Neriah, "Phosphorylation meets ubiquitination: the control of NF-[kappa]B activity," *Annual Review of Immunology*, 18:621-663, 2000.
Karin, "Nuclear factor-kappaB in cancer development and progression," *Nature*, 441:431-436, 2006.
Karin et al., "The IKK NF-kappa B system: a treasure trove for drug development," *Nature Reviews, Drug Discovery*, 3:17-26, 2004.
Kelloff et al., "New agents for cancer chemoprevention," *Journal of Cellular Biology*, 26:1-28, 1996.
Kim et al., "Phosphorylation of the RNA polymerase II carboxyl-terminal domain by CDK9 is directly responsible for human immunodeficiency virus type 1 Tat-activated transcriptional elongation," *Molecular and Cellular Biology*, 22:4622-4637, 2002.
Koumenis and Giaccia, "Transformed cells require continuous activity of RNA polymerase II to resist oncogene-induced apoptosis," *Molecular and Cellular Biology*, 17:7306-7316, 1997.
Krainer et al., "Functional expression of cloned human splicing factor SF2: homology to RNA-binding proteins, U1 70K, and *Drosophila* splicing regulators," *Cell*, 66:383-394, 1991.
Larochelle et al., "T-loop phosphorylation stabilizes the CDK7-cyclin H-MAT1 complex in vivo and regulates its CTD kinase activity," *EMBO Journal*, 20:3749-3759, 2001.

(56) References Cited

OTHER PUBLICATIONS

Lasic, "Novel applications of liposomes," *Trends Biotechnol.*, 16:307-321, 1998.
Le Good et al., "Protein kinase C isotypes controlled by phosphoinositide 3-kinase through the protein kinase PDK1," *Science*, 281:2042-2045, 1998.
Leclerc et al., "*Drosophila* Cdk8, a kinase partner of cyclin C that interacts with the large subunit of RNA polymerase II," *Molecular Biology of the Cell*, 7:505-513, 1996.
Leonetti et al., "Antibody-targeted liposomes containing oligodeoxyribonucleotides complementary to viral RNA selectively inhibit viral replication," *Proc. Natl. Acad. Sci. USA*, 87:2448-2451, 1990.
Liu et al., "A genetically defined model for human ovarian cancer," *Cancer Res.*, 64:1655-1663, 2004.
Marciniak and Sharp, "HIV-1 Tat protein promotes formation of more-processive elongation complexes," *EBMO J.*, 10:4189-4196, 1991.
Mathiowitz et al., "Biologically erodable microspheres as potential oral drug delivery systems," *Nature*, 386:410-414, 1997.
McCracken et al., "The C-terminal domain of RNA polymerase II couples mRNA processing to transcription," *Nature*, 385:357-361, 1997.
Mills et al., "Increased prevalence of K-ras oncogene mutations in lung adenocarcinoma," *Cancer Res.*, 55:1444-7, 1995.
Misteli and Spector, "RNA polymerase II targets pre-mRNA splicing factors to transcription sites in vivo," *Molcecular Cell*, 3:697-705, 1999.
Misteli et al., "The dynamics of a pre-mRNA splicing factor in living cells," *Nature*, 387:523-527, 1997.
Morishita et al., "Single intraluminal delivery of antisense cdc2 kinase and proliferating-cell nuclear antigen oligonucleotides results in chronic inhibition of neointimal hyperplasia," *Proc. Natl. Acad. Sci. USA*, 90:8474, 1993.
Mortillaro et al., "A hyperphosphorylated form of the large subunit of RNA polymerase II is associated with splicing complexes and the nuclear matrix," *Proc. Natl. Acad. Sci. USA*, 93:8253-8257, 1996.
Murray et al., "Protein kinase Ciota is required for Ras transformation and colon carcinogenesis in vivo," *Journal of Cell Biology*, 164:797-802, 2004.
Nakanishi et al., "Activation of the zeta isozyme of protein kinase C by phosphatidylinositol 3,4,5-trisphosphate," *Journal of Biological Chemistry*, 268:13-16, 1993.
Nemunaitis et al., "Irinotecan hydrochloride (CPT-1 1) resistance identified by K-ras mutation in patients with progressive colon cancer after treatment with 5-fluorouracil (5-FU)," *Am. J. Clin. Oncol.*, 20:527-529, 1997.
Neri et al., "Increase in nuclear phosphatidylinositol 3-kinase activity and phosphatidylinositol (3,4,5) trisphosphate synthesis precede PKC-zeta translocation to the nucleus of NGF-treated PC12 cells," *FASEB Journal*, 13:2299-2310, 1999.
Nottage and Siu, "Rationale for Ras and Raf-kinase as a target for cancer therapeutics," *Current Pharmaceutical Design*, 8:2231-2242, 2002.
Oelgeschläger, "Regulation of RNA polymerase II activity by CTD phosphorylation and cell cycle control," *Journal of Cellular Physiology*, 190:160-169, 2002.
O'Keefe et al., "Disruption of pre-mRNA splicing in vivo results in reorganization of splicing factors," *Journal of Cell Biology*, 124:249-260, 1994.
Oltvai et al., "Bcl-2 heterodimerizes in vivo with a conserved homolog, Bax, that accelerates programmed cell death," *Cell*, 74:609-19, 1993.
O'Neill et al., "Role of the kinase MST2 in suppression of apoptosis by the proto-oncogene product Raf-1," *Science*, 306:2267-2270, 2004.
Pacold et al., "Crystal structure and functional analysis of Ras binding to its effector phosphoinositide 3-kinase gamma," *Cell*, 103:931-943, 2000.
Papahadjopoulos et al., "Sterically stabilized liposomes: improvements in pharmacokinetics and antitumor therapeutic efficacy," *Proc. Natl. Acad. Sci. USA*, 88:11460-11464, 1991.
Papaldo et al., "Addition of either Ionidamine or granulocyte colony-stimulating factor does not improve survival in early breast cancer patients treated with high-dose epirubicin and cyclophosphamide," *Journal of Clinical Oncology*, 21:3462-3468, 2003.
Pellegata et al., "K-ras and p53 gene mutations in pancreatic cancer: ductal and nonductal tumors progress through different genetic lesions," *Cancer Res.*, 54:1556-60, 1994.
Pells et al., "Developmentally-regulated expression of murine K-ras isoforms," *Oncogene*, 15:1781-1786, 1997.
Perander et al., "Nuclear import and export signals enable rapid nucleocytoplasmic shuttling of the atypical protein kinase C lambda," *Journal of Biological Chemistry*, 276:13015-13024, 2001.
Peterson et al., "Stimulation of the DNA-dependent protein kinase by RNA polymerase II transcriptional activator proteins," *Journal of Biological Chemistry*, 270:1449-1454, 1995.
Prasad et al., "The protein kinase Clk/Sty directly modulates SR protein activity: both hyper-and hypophosphorylation inhibit splicing," *Molecular and Cellular Biology*, 19:6991-7000, 1999.
Pullen et al., "Phosphorylation and activation of p70s6k by PDK1," *Science*, 279:707-710, 1998.
Quintanar-Guerrero et al., "Preparation and characterization of nanocapsules from preformed polymers by a new process based on emulsification-diffusion technique," *Pharm. Res.*, 15:1056-1062, 1998.
Ravagnan et al., "Lonidamine triggers apoptosis via a direct, Bcl-2-inhibited effect on the mitochondrial permeability transition pore," *Oncogene*, 18:2537-2546, 1999.
Regala et al., "Atypical protein kinase C iota is an oncogene in human non-small cell lung cancer," *Cancer Res.*, 65:8905-8911, 2005.
Renneisen et al., "Inhibition of expression of human immunodeficiency virus-1 in vitro by antibody-targeted liposomes containing antisense RNA to the env region," *J. Bio. Chem.*, 265:16337-16342, 1990.
Rodriguez-Viciana et al., "Phosphatidylinositol-3-OH kinase as a direct target of Ras," *Nature*, 370:527-532, 1994.
Rossi et al., "Specific phosphorylation of SR proteins by mammalian DNA topoisomerase I," *Nature*, 381:80-82, 1996.
Rossman et al., "GEF means go: turning on RHO GTPases with guanine nucleotide-exchange factors," *Nature Reviews Molecular Cell Biology*, 6:167-180, 2005.
Rowley and Van Ness, "Activation of N-ras and K-ras induced by interleukin-6 in a myeloma cell line: implications for disease progression and therapeutic response," *Oncogene*, 21:8769-8775, 2002.
Rubinstein et al., "Comparison of in vitro anticancer-drug-screening data generated with a tetrazolium assay versus a protein assay against a diverse panel of human tumor cell lines," *J. Natl. Cancer Inst.*, 82:1113-1118, 1990.
Samuels et al., "Nerve growth factor stimulates the interaction of ZIP/p62 with atypical protein kinase C and targets endosomal localization: evidence for regulation of nerve growth factor-induced differentiation," *Journal of Cellular Biochemistry*, 82:452-66, 2001.
Sapra and Allen, "Ligand-targeted liposomal anticancer drugs," *Prog. Lipid Res.*, 42:439-462, 2003.
Sebti and Adjei, "Farnesyltransferase inhibitors," *Seminars in Oncology*, 31:28-39, 2004.
Shiekhattar et al., "Cdk-activating kinase complex is a component of human transcription factor TFIIH," *Nature*, 374:283-287, 1995.
Stephens et al., "Protein kinase B kinases that mediate phosphatidylinositol 3,4,5-trisphosphate-dependent activation of protein kinase B," *Science*, 279:710-714, 1998.
Sun et al., "Phase I and pharmacokinetic trial of the proapoptotic sulindac analog CP-461 in patients with advanced cancer," *Clinical Cancer Research*, 8:3100-3104, 2002.
Takenaga et al., "Microparticle resins as a potential nasal drug delivery system for insulin," *J. Control Release*, 52:81-87, 1998.
Taylor et al., "Sulindac sulfone inhibits K-ras-dependent cyclooxygenase-2 expression in human colon cancer cells," *Cancer Res.*, 60:6607-6610, 2000.
Teraishi et al., "P-glycoprotein-independent apoptosis induction by a novel synthetic compound, MMPT [5-[(4-

(56) References Cited

OTHER PUBLICATIONS methylphenyl)methylene]-2-(phenylamino)-4(5H)-thiazolone]," *Journal of Pharmacology and Experimental Therapeutics*, 314:355-362, 2005.

Thompson, "Apoptosis in the pathogenesis and treatment of disease," *Science*, 267:1456-62, 1995.

Vellard et al., "A potential splicing factor is encoded by the opposite strand of the trans-spliced c-myb exon," *Proc. Natl. Acad. Sci. USA*, 89:2511-2515, 1992.

Vivanco and Sawyers, "The phosphatidylinositol 3-Kinase AKT pathway in human cancer," *Nature Reviews Cancer*, 2:489-501, 2002.

Vlahos et al., "A specific inhibitor of phosphatidylinositol 3-kinase, 2-(4-morpholinyl)-8-phenyl-4H-1-benzopyran-4-one (LY294002).," *Journal of Biological Chemistry*, 269:5241-5248, 1994.

Vogelstein et al., "Genetic alterations during colorectal-tumor development," *N. Engl. J. Med.*, 319:525-32, 1988.

von Gise et al., "Apoptosis suppression by Raf-1 and MEK1 requires Mek- and phosphatidylinositol 3-kinase-dependent signals," *Molecular and Cellular Biology*, 21:2324-2336, 2001.

Wang et al., "Bcl-2 targets the protein kinase Raf-1 to mitochondria," *Cell*, 87:629-638, 1996.

Wang et al., "SRPK2: a differentially expressed SR protein-specific kinase involved in mediating the interaction and localization of pre-mRNA splicing factors in mammalian cells," *Journal of Cell Biology*, 140:737-750, 1998.

Wei et al., "A novel CDK9-associated C-type cyclin interacts directly with HIV-1 Tat and mediates its high-affinity, loop-specific binding to TAR RNA," *Cell*, 92:451-462, 1998.

Wellbrock et al., "The RAF proteins take centre stage," *Nature Reviews Molecular Cell Biology*, 5:875-885, 2004.

White et al., "Phosphorylation of tyrosine 256 facilitates nuclear import of atypical protein kinase C," *Journal of Cellular Biochemistry*, 85:42-53, 2002.

Whyte et al., "K- and N-Ras are geranylgeranylated in cells treated with farnesyl protein transferase inhibitors," *Journal of Biological Chemistry*, 272:14459-14464, 1997.

Williams et al., "Low density lipoprotein receptor-independent hepatic uptake of a synthetic, cholesterol-scavenging lipoprotein: implications for the treatment of receptor-deficient atherosclerosis," *Porc. Natl. Acad. Sci USA*, 85:242-246, 1988.

Winter-Vann et al., "A small-molecule inhibitor of isoprenylcysteine carboxyl methyltransferase with antitumor activity in cancer cells," *Proc. Natl. Acad. Sci. USA*, 102:4336-4341, 2005.

Wu et al., "Induction of apoptosis and down-regulation of Bcl-XL in cancer cells by a novel small molecule, 2 [[3-(2,3-dichlorophenoxy)propyl]amino]ethanol," *Cancer Res.*, 64:1110-1113, 2004.

Yamaguchi et al., "Stimulation of RNA polymerase II elongation by hepatitis delta antigen," *Science*, 293:124-127, 2001.

Yamamoto et al., "Sulindac inhibits activation of the NF-kappaB pathway," *Journal of Biological Chemistry*, 274:27307-27314, 1999.

Yin et al., "The anti-inflammatory agents aspirin and salicylate inhibit the activity of I(kappa)B kinase-beta," *Nature*, 396:77-80, 1998.

Zalipsky et al., "Long circulating, cationic liposomes containing amino-PEG-phosphatidylethanolamine," *FEBS Lett.*, 353:71-74, 1994.

Zalipsky, "Synthesis of an end-group functionalized polyethylene glycol-lipid conjugate for preparation of polymer-grafted liposomes," *Bioconjug. Chem.*, 4:296-299, 1993.

Zambaux et al., "Influence of experimental parameters on the characteristics of poly(lactic acid) nanoparticles prepared by a double emulsion method," *J. Control Release*, 50:31-40, 1998.

Zandomeni and Weinmann, "Inhibitory effect of 5,6-dichloro-1-beta-D-ribofuranosylbenzimidazole on a protein kinase," *Journal of Biological Chemistry*, 259:14804-14811, 1984.

Zeng et al., "Dynamic relocation of transcription and splicing factors dependent upon transcriptional activity," *EMBO J.*, 16:1401-1412, 1997.

Zhang et al., "Integrative genomic analysis of protein kinase C (PKC) family identifies PKCiota as a biomarker and potential oncogene in ovarian carcinoma," *Cancer Res.*, 66:4627-4635, 2006.

Zhang et al., "Role of BAX in the apoptotic response to anticancer agents," *Science*, 290:989-992, 2000.

Zhu et al., "Farnesyltransferase inhibitors as anticancer agents: current status," *Current Opinion in Investigational Drugs*, 4:1428-1435, 2003.

Zhu et al., "Induction of S-phase arrest and p21 overexpression by a small molecule 2[[3-(2,3-dichlorophenoxy)propyl] amino]ethanol in correlation with activation of ERK," *Oncogene*, 23:4984-4992, 2004.

Zhu et al., "Bik/NBK accumulation correlates with apoptosis-induction by bortezomib (PS-341, Velcade) and other proteasome inhibitors," *Oncogene*, 24:4993-4999, 2005.

zur Mühlen et al., "Solid lipid nanoparticles (SLN) for controlled drug delivery—drug release and release mechanism," *Eur. J. Pharm. Biopharm.*, 45:149-155, 1998.

Office Communication issued in Chinese Patent Application No. 200680051618.4, dated Mar. 12, 2012. (English Translation).

\* cited by examiner

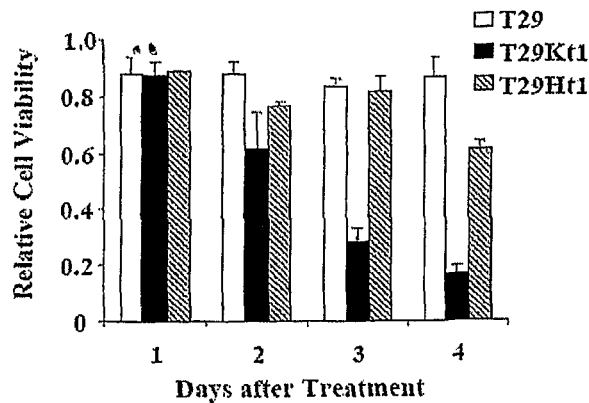
FIG. 1C
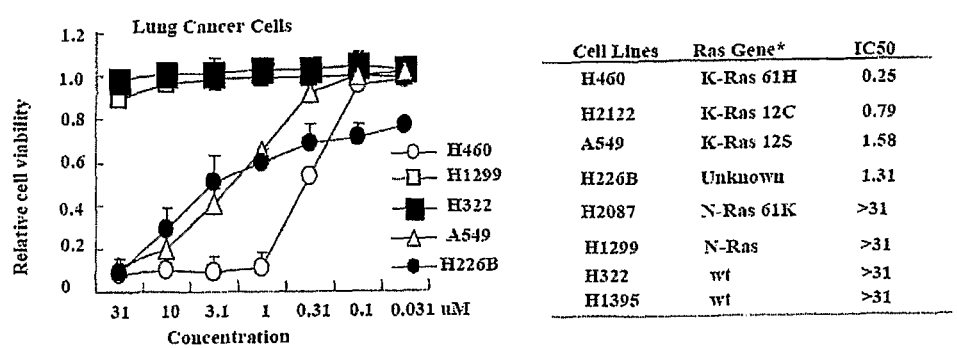
* Based on published data and Cancer Genome Project database (http://www.sanger.ac.uk/genetics/CGP/)
FIG. 2A      FIG. 2B

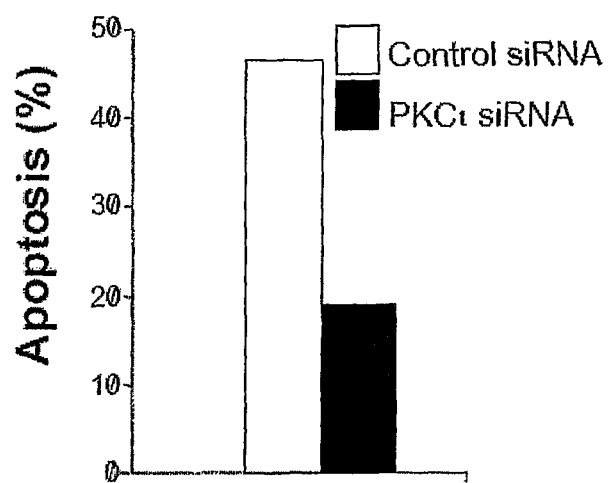
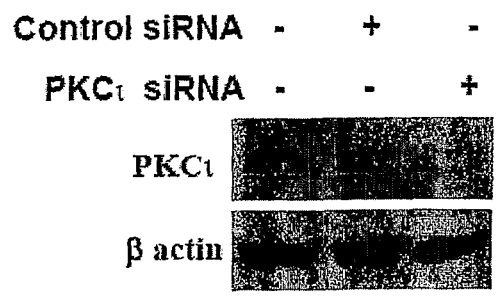
FIG. 9A

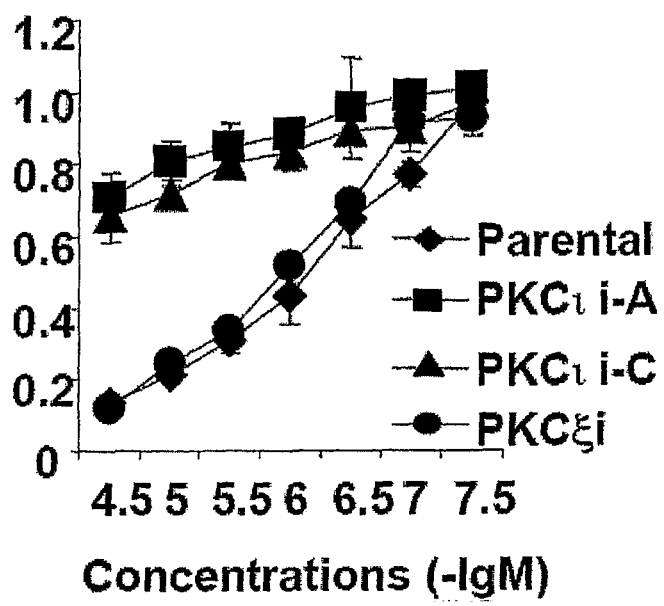
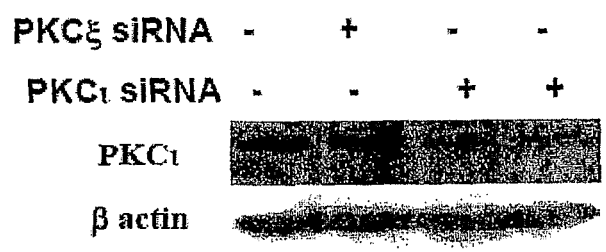
FIG. 9B

R2 = 2-, 3-, 4-, 5- substitute, Br; CF$_3$; Cl; Me; NO$_2$;

ONCOGENIC RAS-SPECIFIC CYTOTOXIC COMPOUND AND METHODS OF USE THEREOF

This application is a national phase application under 35 U.S.C. §371 of International Application No. PCT/US06/61219 filed 22 Nov. 2006, which claims priority to U.S. Provisional Patent application Ser. No. 60/739,865 filed Nov. 23, 2005 both of which are incorporated herein by reference in their entirety.

This invention was made with government support under grant numbers CA092487 and CA098582 awarded by the National Institutes of Health. The government has certain rights in the invention.

BACKGROUND OF THE INVENTION

I. Field of the Invention

This invention relates generally to treatments for cancers and, more specifically, to small molecules that induce cell death and/or suppress cell growth of cancer cells, particularly Ras-mutant and tumorigenic cancer cells.

II. Background

Mutations that lead to activation of three oncogenic ras genes, R-ras, K-ras, and N-ras, were frequently found in a variety of tumor types, including 90% pancreatic, 50% colorectal and 50% lung adenocarcinomas, 50% of thyroid tumors, and 30% myeloid leukemia, but these mutations are not present in normal cells. Of the three ras genes, K-ras mutations are the most frequently found in tumors, including adenocarcinomas of pancreas (70-90%), colon (50%) and lung (50%). Mouse strains carrying alleles of K-ras that can be activated by spontaneous recombination are highly predisposed to a range of tumor types, predominantly early onset lung cancer. Addition of HRAS(V12) or KRAS(V12) mutant gene can be sufficient to render human ovarian surface epithelial cells immortalized with the catalytic subunit of human telomerase reverse transcriptase (hTERT) and the SV40 early genomic region to form tumors in nude mice. Moreover, withdrawal of doxycycline-inducible oncogenic 1H-ras or K-ras can cause apoptosis in tumor cells and regression of tumors of transgenic mice. Therefore, mutations of ras genes play important roles in tumorigenesis and maintenance of malignant phenotypes, and these mutations of ras genes serve as important targets of anticancer therapy. Moreover, because active ras functions are required for replication of some viruses, such as reovirus, hepatitis B virus, herpes virus, and coxsaclievirus and some adenovirus, agents that suppress ras function may also be used as antiviral therapeutics.

Because ras proteins have to be translocated to the inner leaflet of the plasma membrane in order for them to interact with a diversity of membrane receptors and modulate signal transduction of a variety signaling pathways that govern cell growth, proliferation, differentiation and death, agents that interrupt posttranslational modifications required for ras trafficking to the plasma membrane have been intensively investigated for suppression of ras function. For example, farnesyltransferase inhibitors (FTIs) have been intensively investigated in preclinical and clinical cancer therapy. This approach, however, may be effective in preventing the trafficking of H-ras to the plasma membrane, but not K-ras and N-ras, because in the presence of FTIs, N- and K-Ras proteins are geranylgeranylated and transferred to the membrane. Clinical trials from several phase II and phase III studies also showed that FTIs fail to show significant single-agent activity in lung cancer, pancreatic cancer, colorectal cancer, bladder cancer and prostate cancer. Thus, novel compounds that specifically induce cell death or suppress cell proliferation of Ras mutant cells are desirable for anticancer therapy.

A major challenge in cancer therapy is to identify therapeutic agents that are highly specific for malignant cells or malignant tissues. Because malignant cells have the same metabolic pathways as normal cells, and because they are adopted as "self" cells despite the numerous mutations they contain, all anticancer drugs used today affect cellular targets that are shared by normal and cancerous cells. As a result, the use of conventional chemotherapy and radiation therapy is usually limited by a low therapeutic index. In fact, most anticancer drugs used today were discovered because of their ability to kill rapidly dividing cancer cells in vitro and thus are also toxic to rapidly dividing normal cells, such as bone-marrow hematopoietic precursors and gastrointestinal mucosal epithelial cells (Kaelin, 2005). Nevertheless, because of genetic and epigenetic changes in cancer cells, it is possible to identify tumor-selective cytotoxic agents by synthetic lethality screening for compounds that kill cancer cells but not normal cells.

SUMMARY OF THE INVENTION

Embodiments of the invention are directed to a group of compounds (Oncrasins, for oncogenic Ras inhibiting compounds) that have synthetic lethal effects on cancer cells, particularly cancer cells with oncogenic K-Ras and/or atypical protein kinase C. Oncrasin compounds can effectively kill a variety of lung, colon, and pancreatic cancer cells with K-Ras mutations at low micromolar or nanomolar concentrations but did not kill normal cells with normal levels of wild-type K-Ras. The cytotoxic effects correlated with the induction of apoptosis. Treatment with Oncrasin compounds led to abnormal intracellular distribution of atypical protein kinase C iota (KCl or PKCiota), aggregation of RNA spliceosome or malfunction of RNA processing. Knockdown of K-Ras or PKCiota by siRNA diminishes Oncrasin-induced apoptosis in cancer cells, suggesting that Oncrasin-induced apoptosis requires activity of K-Ras and/or PKCiota. The Oncrasin compounds can also suppress Raf-1 expression and TNFα-induced NFκB activation. The in vivo administration of Oncrasin compounds suppressed the growth of human xenograft tumors in nude mice and prolonged the survival of tumor-bearing animals without causing detectable toxicity. Of more than 100 analogues tested, about 30 Oncrasin compounds are effective in inducing cytotoxicity in a variety of cancer cell lines. This toxicity is contemplated to be an induction of a synthetic lethality or a Ras protein or Ras related pathway. A synthetic lethality need not depend on the presence of a mutated Ras protein and may be effective in cells having a wild-type or variant Ras, i.e., one that has no pathologic consequences and is thus not considered a "mutant." Thus, Oncrasin compounds could be promising potential agents for treatment of cancers, inflammatory, and infectious diseases.

In view of the foregoing, to search for compounds that can specifically kill ras mutant cancer cells, embodiments of methods of the present invention can use immortalized human ovarian surface epithelial cells (designated T29), and its tumorigenic derivatives transformed with either mutant H-ras (T29H) or mutant K-ras (T29K), to screen a chemical library (e.g., ChemBridge Corporation library) for compounds that can selectively kill tumor cells. Several compounds can be identified that can selectively kill T29K, T29H or both, but not parental T29 cells. One compound (1-[(4-chlorophenyl)methyl]-1H-Indole-3-carboxaldehyde, or CPMIC, i.e., Oncrasin-1 for Oncogenic Ras Inhibiting compound 1) that is highly specific for T29K is also very effective for several lung cancer cell lines with K-ras mutations. This compound is not toxic to T29, T29H and H322 (lung cancer cell, ras wild-type) at 33 μM (the highest concentration tested), but it can effectively kill K-ras mutant T29K or H460 (lung cancer cells) at 10 μM and 1 μM, respectively. Oncrasin-1 also induces apoptosis in ras-mutant cells as evidenced by dramatic increases of Propidium Iodide (PI) or Annexin V stained cells, cleavage of caspase-3, and cleavage of caspase-8. Oncrasin-1 dramatically reduces raf-1, a serine/threonine kinase that plays a pivotal role in rar-mediated proliferation and survival of tumor cells. Furthermore, it was determined that several of the analogs of Oncrasin-1 can induce more potent Kras-selective cyclotoxic effects. Together, these results demonstrate that Oncrasin-1 and its analogs can induce oncogenic ras-selective cytotoxic effects in cancer with minimal toxicity to cells with Ras capable of normal function, e.g., wildtype and variants thereof.

Embodiments of invention include compounds and methods that can be therapeutic with reduced risk of toxicity. Typically, a compound will have the general formula or structure represented by Formula I.

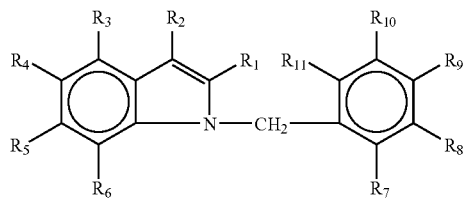

Formula I

In certain embodiments, the groups $R_1$, $R_2$, $R_3$, $R_4$, $R_5$, $R_6$, $R_7$, $R_8$, $R_9$, $R_{10}$, and/or $R_{11}$ are each independently —H, hydroxy, amino, cyano, halo, bromo, chloro, nitro, mercapto, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_2$-$C_{15}$-amido, $C_1$-$C_{15}$-alkylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, or $C_0$-$C_{15}$-silyl.

In certain embodiments, $R_1$, $R_2$, $R_3$, $R_4$, $R_5$, $R_6$, $R_7$, $R_8$, $R_9$, $R_{10}$, and/or $R_{11}$, are substituted or unsubstituted versions of alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkyloxy, acyloxy, alkylamino, alkenylamino, alkynylamino, arylamino, aralkylamino, heteroarylamino, heteroaralkylamino, or amido.

In certain aspects, $R_1$, $R_2$, $R_3$, $R_4$, $R_5$, $R_6$, $R_7$, $R_8$, $R_9$, $R_{10}$, and/or $R_{11}$ are each independently —H, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$C(CH$_3$)$_3$, —C$_6$H$_5$, —C$_6$H$_4$CH$_3$, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)$_2$, —C$_6$H$_3$(CH$_3$)CH$_2$CH$_3$, F, Cl, Br, I, —OH, —OCH$_3$, —OCH$_2$CH$_3$, —OCH$_2$CH$_2$CH$_3$, —OCH(CH$_3$)$_2$, —OCH(CH$_2$)$_2$, —OCH$_2$CF$_3$, —OCOCH$_3$, —OC$_6$H$_5$, —NH$_2$, —NHCH$_3$, —NHCH$_2$CH$_3$, —NHCH$_2$CH$_2$CH$_3$, —NHCH(CH$_3$)$_2$, —NHCH(CH$_2$)$_2$, —N(CH$_3$)$_2$, —N(CH$_3$)CH$_2$CH$_3$, —N(CH$_2$CH$_3$)$_2$, —NHCOCH$_3$, —NHCO$_2$C(CH$_3$)$_3$, —CH$_2$F, —CH$_2$Cl, —CH$_2$Br, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH(CH$_2$)$_2$, —CH$_2$OCH$_2$CF$_3$, —CH$_2$OCOCH$_3$, —CH$_2$NH$_2$, —CH$_2$NHCH$_3$, —CH$_2$N(CH$_3$)$_2$, —CH$_2$NHCH$_2$CH$_3$, —CH$_2$N(CH$_3$)CH$_2$CH$_3$, —CH$_2$NHCH$_2$CH$_2$CH$_3$, —CH$_2$NHCH(CH$_3$)$_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_2$CH$_2$I, —CH$_2$CH$_2$OH, CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH$_2$CH$_2$NHCH(CH$_2$)$_2$, —CH$_2$CH$_2$N(CH$_2$CH$_3$)$_2$, —CH$_2$CH$_2$NHCO$_2$C(CH$_3$)$_3$, —CH$_2$CH═CH$_2$, —CH$_2$CH═CHCH$_3$, —CH$_2$CH═CHCH$_2$CH$_3$, —CH$_2$CH═CHCH$_2$CH$_2$CH$_3$, —CH$_2$CH═CHCH(CH$_3$)$_2$, —CH$_2$CH═CHCH(CH$_2$)$_2$, —CF$_3$, —CN, —CH═CH$_2$, —CH═CHCH$_3$, —COH, —COCH$_3$, —COCH$_2$CH$_3$, —COCH$_2$CH$_2$CH$_3$, —COCH(CH$_3$)$_2$, —COCH(CH$_2$)$_2$, —COCH$_2$CF$_3$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, —COC$_6$H$_3$(CH$_3$)$_2$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_7$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$, —CONHCH$_2$CF$_3$, —C$_6$H$_4$CH═CH$_2$, —C$_6$H$_4$CH═CHCH$_3$, —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$OH, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —C$_{61}$CH$_2$CH═CH$_2$, —C$_6$H$_4$CF$_3$, —C$_6$H$_4$CN, —C$_6$H$_4$C≡CH, —C$_6$H$_4$C≡CCH$_3$, —C$_6$H$_4$C≡CSi(CH$_3$)$_3$, —C$_6$H$_4$COH, —C$_6$H$_4$COCH$_3$, —C$_6$H$_4$COCH$_2$CH$_3$, —C$_6$H$_4$COCH$_2$CF$_3$, —C$_6$H$_4$COC$_6$H$_5$, —C$_6$H$_1$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, —SH, —SCH$_3$, —SC$_6$H$_5$, —SCH$_2$C$_6$H$_5$, or —SCOCH$_3$.

In certain aspects, $R_1$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethyl carboxyethyl, carboxypropyl, carboxybutyl, carbonyl, aldehyde, ester, or ketone group; $R_2$ is alkyl, methyl, ethyl, n-propyl, isopropyl, n-butyl, isobutyl, sec-butyl, tert-butyl, pentyl, hexyl, isopentyl, carboxymethyl carboxyethyl, carboxypropyl, carboxybutyl, alcohol, methanol, ethanol, propanol, butanol, caronyl, aldehyde, ester, ketone, benzyl, or aryl; $R_3$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; $R_4$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, ketone, aryl, heteroaryl, furanyl, indolyl, thiophenyl, thiazolyl, imidazolyl, isoxazoyl, oxazoyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinoline, isoxazolyl, isoquinoline cycloalkyl, alkenyl, cycloalkenyl, phenyl, or pyridyl; $R_5$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, amide, amine, caronyl, aldehyde, ester, or ketone; $R_6$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; $R_7$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; $R_8$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; $R_9$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; $R_{10}$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone; and/or $R_{11}$ is halo, chloro, bromo, hydrogen, alkyl, methyl, ethyl, n-propyl, isopropyl, n-butyl, isobutyl, sec-butyl, tert-butyl, pentyl, hexyl, isopentyl, carboxymethoyl carboxyethyl, carboxypropyl, carboxybutyl, caronyl, aldehyde, ester, or ketone.

In particular aspects, $R_1$ is a halo group, particularly $R_1$ is a chloro or bromo group. In a further aspect $R_2$ is a hydroxy, alkoxy, aldehyde, carboxy, or carbonyl group, particularly $R_2$ is an aldehyde. In still further aspects $R_9$ is a chloro group, in particular $R_9$ is a bromo group. In yet further aspects, $R_3$ is a halo group. In certain aspects, $R_4$ is halo, methyl ester, or methyl quinoline ester group. In further aspects, $R_5$ is methyl or amide group. In still further aspects, $R_6$ is an alkyl group. In yet further aspects, $R_7$ is chloro or bromo group. In certain aspects, $R_8$ is chloro or bromo group. In further aspects, $R_9$ is a chloro group. In still further aspects, $R_{10}$ is a chloro or bromo group. In yet further aspects, $R_{11}$ is chloro group.

The letter "n", in a formula or structure can be 0, 1, 2, 3, 4, 5, or 6.

In some embodiments, a pharmaceutically acceptable salt or prodrug of a compound is provided. The invention also provides optical isomers of the compounds defined by formula or structure. In certain embodiments, the optical isomer of a compound defined by a formula or structure is substantially free from the other optical isomers. In other embodiments, two or more optical isomers are present in the same composition. In certain of these embodiments, two optical isomers are present is roughly equal amounts. In some embodiments, the invention provides for a racemic mixture of an enantiomeric pair of compounds.

In certain embodiments the compounds are 1-[(4-chlorophenyl)methyl]-1H-indole-3-carboxaldehyde (Oncrasin 1), 1-(3-chlorobenzyl)-1H-indole-3-carbaldehyde (Oncrasin 27), 1-(4-bromobenzyl)-1H-indole-3-carbaldehyde (Oncrasin 29), sulfanilamide, N4-[(1-benzylindol-3-yl)methylene]-N1-2-thiazolyl (Oncrasin 42), [1-(3,4-dichlorobenzyl)-1H-indole-3-yl]methanol (Oncrasin 49), [1-(2-fluorobenzyl)-1H-indole-3-carbaldehyde (Oncrasin 51), 1-[(4-chlorophenyl)methyl-1H-indole-3-methanol (Oncrasin 60), (1-[3-(trifluoromethyl)benzyl]-1H-indole-3-yl)methanol (Oncrasin 63), 1-(3-nitrobenzyl)-1H-indole-3-carbaldehyde (Oncrasin 68), 1-[(3-nitrophenyl)methyl-1H-indole-3-methanol (Oncrasin 69), 1-[(4-nitrophenyl)methyl-1H-indole-3-methanol (Oncrasin 71), 1-[(3-chlorophenyl)methyl]-1H-indole-3-methanol (Oncrasin 72); and/or 1-[(4-bromophenyl)methyl-1H-indole-3-methanol (Oncrasin 73).

In some methods of the invention, the cancer cell is a tumor cell. Furthermore, the cell may be administered compositions of the invention in vitro, in vivo, or ex vivo. Thus, the cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds and/or derivatives or analogs thereof, can be used with these combination therapies.

In some embodiments, the cancer cell administered such compositions may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

In certain aspects, the Ras protein is a mutant Ras protein, in particular a mutant K-Ras protein. The K-Ras can have a mutation at any amino acid in the protein, and in particular amino acid glycine 12, glycine 13, glutamine 61, or a combination thereof.

Other methods contemplated by the present invention include: Methods of treating cancer comprising administering a compound cytotoxic to the cancer cell in an amount sufficient to induce apoptosis or inhibit growth of the cancer cell; wherein the cytotoxic compound, or a salt, a metabolite or a prodrug thereof. Methods of treating a viral infection comprising administering an antiviral compound to a subject infected with or at risk of being infected by a virus in an amount sufficient to reduce replication or inhibit growth of the virus in the subject; wherein the antiviral compound in selected from the compounds described herein.

As used herein, the term "$IC_{50}$" refers to an inhibitory dose which results in 50% of the maximum response obtained.

Embodiments of the invention can also include methods of modulating various cellular pathways including, but not limited to PKC activity in a cell, e.g., PKC zeta and/or PKC iota activity; NFκB activation in a cell; RNA transcription in a cell; RNA splicing in a cell; protein metabolism in a cell; protein synthesis in a cell; protein degradation in a cell; Raf-1 activity in a cell or the like.

Also contemplated are pharmaceutical compositions comprising an amount of one or more compounds described herein, or a pharmaceutically acceptable salt or ester thereof, sufficient to inhibit cancer cell growth or viral replication or modulate cellular pathway in a cell and a pharmaceutically acceptable carrier, wherein the compound has the formula:

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Any embodiment discussed with respect to a particular cancer, viral infection, or disorder can be applied or implemented with respect to a different cancer, viral infection, or disorder. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1C (FIG. 1A) Chemical structures of the 6 compounds tested for dose-response. (FIG. 1B) Dose effect of several compounds on T29, T29Ht1, and T29Kt1 cells. The cells were treated with various concentrations (ranging from 0.1 μM to 33 μM) of the compounds listed in A. Cell viability was determined by SRB assays. Control cells were treated with solvent (DMSO), and their value was set as 1. (FIG. 1C) Time course after treatment of T29, T29Kt1, and T29Ht1 cells with compound 1 at a concentration of 33 μM. Cell viability was then determined by SRB assays. The values shown are the mean±SD of 2 assays done in quadruplicate.

FIGS. 2A and 2B Effects of Oncrasin-1 on human lung cancer cells. (FIG. 2A) Human lung cancer cell lines with various statuses of oncogenic Ras genes were treated with Oncrasin-1 at various concentrations. The values shown are the mean±SD of 2 assays done in quadruplicate. (FIG. 2B) The status of Ras gene mutations.

(FIG. 3B) Western blot analysis. H460 cells treated with 1 μM Oncrasin-1 for various times as indicated. Activation of caspase-3 and caspase-8 was detected by Western blot analysis 12-24 h after treatment.

(FIG. 4A) Human lung cancer cell H460 was treated with either a control siRNA or K-Ras siRNA, and then treated with DMSO or Oncrasin-1 (1 μM) for 12 h. Oncrasin-induced apoptotic cells were determined by FACS analysis and normalized with that of DMSO treated cells. The value represents each of two experiments. (FIG. 4B) Western blot analysis of siRNA-mediated K-Ras knockdown.

(FIG. 6C) Comparison of PKCI in T29Kt1, T29 and T29Kt1 knockdown cells.

(FIG. 8A) T29Kt1 cells were treated with Oncrasin-1 or radiation, subcellular localization of SC35 and Rad51 were then determined by antibody staining. (FIG. 8B) Colocalization of PKCiota and SC35 determined under regular fluorescent microscope and (FIG. 8C) confocal microscope. (FIG. 8D) T29Kt1 and T29 cells were treated with DMSO or Oncrasin-1 and then stained with ASF/SF2 antibody.

FIGS. 9A and 9B Effects of PKCiota in Oncrasin-induced cytotoxicity. (FIG. 9A) Transient knockdown of PKCiota in H460 cells. (FIG. 9B) Stably knockdown of PKCiota in T29Kt1 cells. PKCzeta siRNA vector was used as control. Apoptosis induction and cell viability were compared in knockdown and control cells upon Oncrasin-1 treatment.

(FIG. 10A) H460 cells were treated with various concentrations of Oncrasin-1 and harvested 24 h later for Western blot analysis. (FIG. 10B) Reverse transcriptase-based polymerase chain reaction (RT-PCR) assay. H460 cells treated with 1 μM Oncrasin-1 for various times or at various concentrations for 24 h, as indicated. (+, −, positive and negative controls). (FIG. 10C) Western blot analysis showed the changes in Raf-1 expression in the cells 24 h after treatment with DMSO or Oncrasin-1 (10 μM). (FIG. 10D) Dose effects of Oncrasin-1 on stable cell lines transfected with Raf-1 plasmids. Parental H460 cells and H460 cells transfected with wild-type Raf-1 (Raf-1), constitutive Raf-1 (Raf-1C), or dominant-negative Raf-1 Raf-1/DN) were treated with various concentrations of Oncrasin-1, and cell viability was determined by SRB assay.

(FIG. 11C) H460 and T29K cells were treated with DMSO or different concentrations of Oncrasin-1 as indicated for 12 h, with or without TNFα (1 ng/ml). The NFκB activity was analyzed by EMSA.

(FIG. 13B) NMR test of Oncrasin-27.

(FIG. 14A) Suppression of H460 tumor growth in vivo. Mice with subcutaneous tumors derived from H460 cells were treated with Oncrasin-1 or Oncrasin-27 as indicated. Tumor volumes were monitored over time after the treatments. The values represent the means±SD of data from 5 mice per group. The mean tumor volume in the mice treated with Oncrasin-1 or Oncrasin-27 alone differed significantly from that of the solvent-treated mice (p<0.05). (FIG. 14B) Average survival. The mean survivals in mice treated with solvent, Oncrasin-1, and Oncrasin-27 were 24, 32, and 34 days, respectively.

(FIG. 16A) T29, T29Kt1, and H460 cells were treated with 10 μM Oncrasin-1 (T29 and T29Kt1) or 1 μM Oncrasin-1 (H460). Twelve hours later, cells were harvested for Western blot analysis for phosphorylation of RNA polymerase II and SR proteins. Cells treated with DMSO were used as control (C). (T) cells treated with Oncrasin-1. Arrows indicate reduced phosphorylation of the polymerase II (pPolII) and SR proteins (pSR) (FIG. 16B) In vitro transcription assay with HeLa cell nuclear extracts (Promoega). The assay was performed following manufacturers instructions. The concentrations used are indicated on the top of the panel. DRB was used as positive control for transcription inhibition.

DETAILED DESCRIPTION OF THE INVENTION

Figure 1A:
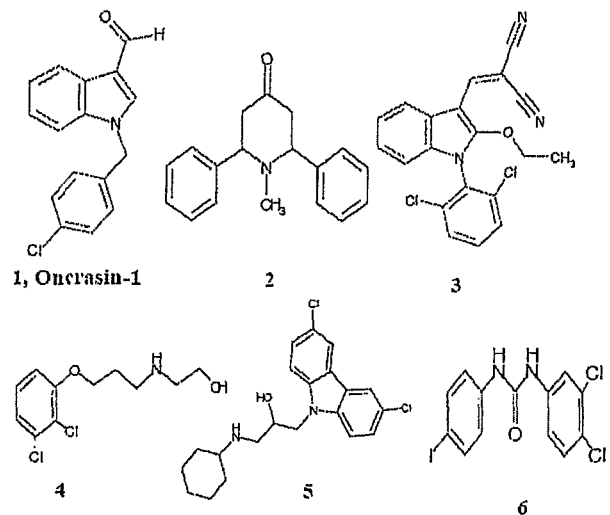

The present invention now will be described more fully hereinafter with reference to the accompanying drawings in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

I. Ras Related Conditions and Pathways

A. Cancers

Oncogenic ras genes, H-ras, K-ras, and N-ras, are frequently found in a variety of tumor types. The K-ras gene encodes 2 splicing isoforms, a major K-Ras 4B and a minor K-Ras 4A. The K-Ras 4B, H-Ras, and N-ras are ubiquitously expressed, whereas K-Ras 4A is expressed mainly in kidney, liver, and gastrointestinal tissues (Pells et al., 1997; Fiorucci and Hall, 1988). As a subfamily of small guanine nucleotide-binding proteins, Ras proteins cycle between an active GTP-bound form and an inactive GDP-bound form (Bar-Sagi and Hall, 2000; Colicelli, 2004). Binding of Ras with GTP is facilitated by guanine nucleotide exchange factors through catalyzing the release of GDP and is required for the interaction of Ras with target proteins (Rossman et al., 2005). The intrinsic GTPase activity that is enhanced by GTPase-activating proteins (Bernards and Settleman, 2004) converts GTP to GDP, leading to a GDP-bound, inactive Ras. Ras mutations that diminish the GTPase activity or decrease the GDP binding capacity render Ras in a constitutively active, GTP-bound status. Ras protein can also be activated by other mechanisms. In the absence of a Ras mutation, increased activity of Ras proteins is frequently detected in human cancer due to gene amplification (Galinana et al., 1995; Hoa et al., 2002; Filmus and Buick, 1985), overexpression (Algarra et al., 1998; Coleman, 1994) and an increase in upstream signals from tyrosine-kinase growth-factor receptors such as Her2 (Ehrhardt et al., 2004; Rowley and Van Ness, 2002).

Synthesized in cytosol, Ras proteins are transferred to the inner leaflet of the plasma membrane, where they interact with a diversity of membrane receptors and execute signal transduction in a variety of signaling pathways that govern cell growth, proliferation, differentiation, and death. Several steps of posttranslational modifications are critical for trafficking of Ras to the plasma membrane, including farnesylation at the cysteine residue of the carboxy-terminal CAAX motif, removal of the AAX peptide, and methylation of farnesyl-cysteine at the C-terminus (Hancock, 2003). For H-Ras and N-Ras, palmitoylation on cysteine residues near the C-terminal is also required for Ras relocalization to the membrane. For K-Ras, a polybasic domain located at the C-terminal serves as the second signal for membrane localization (Cadeallader et al., 1994; Hancock et al., 1990). Because farnesylation of Ras is critical for its biologic function, farnesyltransferase inhibitors (FTIs) have been intensively investigated in preclinical and clinical cancer therapy (Sebti and Adjei, 2004; Zhu et al., 2003; Baum and Kirschmeier, 2003). This approach, however, may be effective in preventing the trafficking of H-Ras to plasma membrane, but not K-Ras and N-Ras, because in the presence of FTIs, N- and K-Ras proteins are geranylgeranylated and transferred to the membrane (James, et al., 1995; Whyte et al., 1997; James et al., 1996). Several phase II and phase III clinical trials also showed that FTIs did not have significant single-agent activity in lung, pancreatic, colorectal, bladder, and prostate cancers (Sebti and Adjei, 2004; Zhu et al., 2003; Baum and Kirschmeier, 2003). Therefore, although oncogenic Ras could be an ideal target for anticancer therapy, oncogenic Ras-targeted, effective therapeutic agent is not yet clinically available.

In the ongoing search for compounds that can specifically kill Ras-mutant cancer cells, the inventors used human ovarian surface epithelial cells immortalized with the catalytic subunit of human telomerase reverse transcriptase and the SV40 early genomic region (designated T29) and their tumorigenic derivatives transformed with either mutant H-Ras (T29Ht1) or mutant K-Ras (T29Kt1), which were established in Dr. Jinsong Liu's laboratory at M. D. Anderson Cancer Center (Liu et al., 2004), to screen a chemical library from ChemBridge Corporation (San Diego, Calif.). Cell-based, synthetic lethality was used for the screening. Of 10,000 compounds screened, the inventors identified a compound, (1-[(4-chlorophenyl)methyl]-1H-indole-3-carboxaldehyde), designated Oncrasin-1 (Oncogenic Ras inhibiting compound 1), that was highly selective for T29Kt1 cells at a wide range of doses. This compound was not toxic to T29 or T29Ht1 at any of the doses tested. Moreover, Oncrasin-1 was effective against several human lung, colon, and pancreatic cancer cells that harbor K-ras mutations. The inventors also tested more than 100 analogues with chemical structures similar to that of Oncrasin-1, obtained commercially or synthesized in my laboratory, and found more than 30 of them are effective against cancer cells with K-Ras mutations. Around 20 of them are more effective or as effective as Oncrasin-1 in inducing oncogenic Ras-specific cytotoxicity. Molecular studies revealed that Oncrasin compounds induced apoptosis, aggregation of RNA spliceosomes, and abnormal subcellular distribution of PKCiota, and dephosphorylation of the largest subunit of mammalian RNA polymerase II. Knockdown of K-Ras or PKCiota by siRNA diminishes Oncrasin-induced apoptosis in cancer cells, suggesting that Oncrasin-induced apoptosis requires activity of K-Ras and/or PKCiota. Moreover, Oncrasin compounds can suppress Raf protein expression and inhibit TNFα induced NFκB activation. Thus, Oncrasin compounds could be a useful new class of oncogenic Ras-selective anticancer agents that impose minimal toxicity.

To test the effect of the compounds that selectively kill T29K or T29H cells, several of these compounds were obtained from ChemBridge Corporation in order to determine the dose responses in these cells. Of six compounds tested, one compound (1-[(4-chlorophenyl)methyl]-1H-Indole-3-carboxaldehyde) (Oncrasin 1) was highly selective for T29K at a wide range of doses, while the others had either limited selectivity or narrow selective dose windows (FIG. 1). Focus was thus placed on the antitumor effect of that K-ras specific compound. A time course assay showed that oncrasin-1 also caused time-dependent toxicity in T29K cells but not in other counterparts. Chemically, this compound has a similar core structure as Indole-3-carbinol (I3C), a naturally occurring constituent of many plant foods that has been tested for prevention and treatment of cancer. However, I3C did not induce any cytotoxicity in the three cell lines tested, when tested at the same dose range as tested for the leader (data not shown).

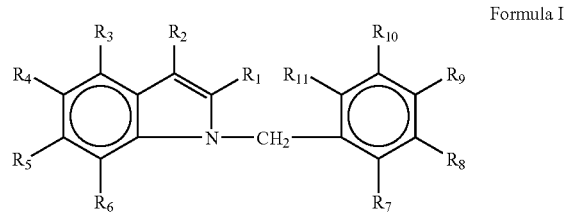

Formula I

To further evaluate the antitumor activity of Oncrasin-1 (Formula I where $R_2$ is CH=O; $R_9$ is Cl; and $R_1$, $R_3$, $R_4$, $R_5$, $R_6$, $R_7$, $R_8$, $R_{10}$, and $R_{11}$ are hydrogen), the effects of this compound were tested in six human lung cancer cell lines with differing ras statuses. The result showed that Oncrasin-1 is highly effective on the lung cancer cell line H460, H212, and A549. These three cell lines contain Q61H, G12C, and G12S mutation in Kras, respectively. Oncrasin-1 is also effective on H226b, which ras status is unknown. It is not effective on H322 (ras wild-type), H1299 (with mutation in Nras), and A549 (with mutation at K12). This result suggested that Oncrasin-1 is not only effective on ovarian cancer cells with Kras mutations, but is also effective on some lung cancers with Kras mutations.

To study whether Oncrasin-1 induced antitumor activity is caused by suppression of cell proliferation or by cell killing, Annexin V/Propidium Iodide (PI) staining of T29, T29K and H460 cells after treatment with 30 μM (for T29 or T29K) or 3 μM (for H460) was performed. At 12-24 h after the treatment, 70% to 90% of H460 and T29K cells were staining positive for either Annexin V, PI or both, suggesting that the majority of the cells were killed by treatment with Oncrasin-1. In contrast, the control samples of H460 and T29K cells, and samples of T29 cells treated with Oncrasin-1, had less than 10% Annexin V and/or PI positive cells. This result indicated that Oncrasin-1 can effectively induce cell killing in T29K and H460 cells.

Apoptosis induction in H460 cells was also analyzed. H460 cells were treated with 1 μM of Oncrasin-1 for 6 to 24 h. Cells treated with DMSO were used as controls. The cell lysates were then used for a western blot assay to detect the cleavage of caspase-3 and caspase-8. The result showed that Oncrasin-1 can effectively induce caspase-3 and caspase-8 activation, indicating that Oncrasin-1 can induce apoptosis in these cells. After treatment with Oncrasin-1, the expression of some molecules involved in Ras signaling pathways was also evaluated. Western blot analysis showed that treatment of H460 with Oncrasin-1 resulted in a dramatic reduction in Raf-1, a serine/threonine kinase that plays a pivotal role in RAR-mediated proliferation and the survival of tumor cells, and serves as an important target of anticancer therapy. Active Raf-1 can be translocated to mitochondria where it executes antiapoptosis signaling by interaction with Bad or other protein substrates. Raf-1 is also a pivotal regulator of endothelial cell survival during angiogenesis. Ablation of Raf-1 renders cells hypersensitive to apoptosis despite normal regulation of extracellular signal-regulated kinases. Thus, it is possible to induce antitumor activity by suppressing raf-1.

To study whether a similar antitumor effect can be induced by analogs of Oncrasin-1, four analogs from ChemBridge Corporation were obtained and their cytotoxic effect in H460, T29 and T29K cells was evaluated. Three of them were highly effective on H460. Two of them were very effective on T29K cells, with the other two having some selectivity for T29K and T29H cells when compared with T29 cells, but with less potency. This result suggested that some analogs of Oncrasin-1 can also function as antitumor agents.

As a subfamily of small guanine nucleotide-binding proteins, Ras cycles between an active GTP-bound form and an inactive GDP-bound form. Binding of Ras with GTP is facilitated by guanine nucleotide exchange factors (GEFs) through catalyzing the release of GDP, and is required for the interaction of Ras with target proteins. The intrinsic GTPase activity that is enhanced by GTPase-activating proteins (GAPs), converts GTP to GDP, leading to a GDP-bound, inactive Ras. Ras mutations that diminish the GTPase activity or decrease the GDP binding capacity render ras in a constitutively active, GTP-bound status. Interestingly, Oncrasin-1 has a similar core structure as guanine. Whether Oncrasin-1 will compete with GTP for binding with mutant ras protein or other ras family members is not yet clear.

Because Ras is frequently mutated in pancreatic cancers and colorectal cancers, the compounds and their analogs may be useful for treatment of those cancers. The antitumor activity of Oncrasin-1 and its analogs will be assessed in cultured cancer cells derived from those cancers. The in vivo antitumor activity of those compounds will also be investigated in nude mice bearing human cancer xenografts or in transgenic mice that develop tumors because of ras gene mutation.

Ongcogenic Ras mutations were observed in about 30% of human cancers, including 90% of pancrease cancer and 50% of lung and colon cancers. K-ras mutations are most frequent in human cancers. Farnesylate transferase inhibitors (FTIs) that can inhibit ras function are currently being tested in clinical trials for the treatment of cancers. FTIs are effective for H-ras mutations, but not for K-ras mutations. Most clinical trials with FTIs failed when used alone, probably because K-ras mutations but not H-ras mutations are common in human cancers. The compound described here effectively kills K-ras mutant cancers and, therefore, might prove more effective than FTIs for cancer therapy. It has been reported that some viruses replicate more effectively in Ras-active cells. Thus, Ras-specific cytotoxic compounds may also be used for anti-viral therapy.

A. Ras Signaling Pathway and Molecular Mechanisms of Oncrasin-Induced Apoptosis

Molecular mechanisms of apoptosis induction use several pathways and proteins to effect cell death. Proteins involved in apoptosis and/or involved in Ras signaling pathways include, but is not limited to Bax, Bik, Bcl2, Bcl-XL, Raf-1, B-Raf, Akt, Mst1 and atypical protein kinase C (aPKC) zeta and PKCiota. Bax and Bik are proapoptotic proteins whereas Bcl2 and BclXL are antiapoptotic proteins. The ratio of those pro- and anti-apoptotic proteins has been reported to be the critical determinant for the induction or inhibition of apoptosis (Oltvai et al., 1993; Zhang et al., 2000). Raf proteins are serine/threonine kinases that plays pivotal role in Ras-mediated signaling pathway (Jun et al., 1999; Wellbrock et al., 2004). In humans and other vertebrates, there are three RAF genes that encode A-Raf, B-Raf and C-Raf (Raf-1), respectively (Wellbrock et al., 2004; Garnett and marais, 2004). Raf is activated by Ras and in turn activates mitogen-activated protein kinase kinase (MEK) and extracellular signal-regulated kinases (ERK) signaling cascade (Wellbrock et al., 2004), leading to resistance to apoptosis. In addition activation of MEK/ERK pathway, active Raf-1 can be translocated to mitochondria and execute antiapoptosis signaling by interaction with Bad or other protein substrates (von Gisse et al., 2001; Wang et al., 1996). Raf-1 can also counteract apoptosis by suppressing the activation of mammalian sterile 20-like kinase (MST2) (O'Neill et al., 2004). Recently, various activating mutations of the B-RAF gene have been identified in various human cancers, including malignant melanomas (60-70%), thyroid cancer (36-50%), colorectal cancer (5-22%), and serous ovarian cancer (30%), and at lower frequency in a wide range of other human cancers (Davies et al., 2002; von Gise et al., 2001), underscoring the importance of Raf in anticancer therapy.

The AKT and the atypical PKCs, PKC zeta and PKCiota, are activated by Ras via PI3K/PDK1 pathway. Unlike other protein kinase C members, PKCzeta and PKCiota are insensitive to the regulation by diacylglycerol (DAG), $Ca^{2+}$, or phorbol esters, but are activated by phosphoinositol-3-kinase (PI3K) and its lipid product phosphotidylinositol-3,4,5-triphosphate (PIP3) (Nakanishi et al., 1993). Phosphorylation of Thr410 (Thr 403) in aPKCs by 3-Phosphoinositide-dependent protein kinase-1 CPDK1) is PI3K dependent and serve as direct ON/OFF switch for aPKCs (Le Good, 1998). PDK1 is a constitutively active kinase, however, its access to substrates is regulated by phosphoinositides (Pullen et al., 1998; Stephens et al., 1998). Ras directly interacts with the catalytic subunit of phosphatidylinositol-3-OH kinase (PI3Ks) in a GTP-dependent manner and activates PI3Ks (Rodriguez-Viciana et al., 19941 Pacold et al., 2000), leading to generation of short-lived second messenger product such as phosphatidylinositol 3,4,5-phosphate (PIP3) (Vivanco and Sawyers, 2002) and activation of many PI3K/PDK1-dependent kinases, including aPKC (Le Good et al., 1998) and Akt (Alessi et al., 1997). Moreover, Ras proteins can directly interact with aPKCs in vitro and in vivo, regulating aPKC activities (Diaz-Meco et al., 1994; Fedorov et al., 2002). Evidences also demonstrated that the aPKCs function as downstream Ras effectors mediating signal transduction of Ras signaling pathways (Fedorov et al., 2002; Berra et al., 1993) and being required for Ras-induced oncogenesis (Murray et al., 2004).

II. Oncrasin Compounds

Oncrasin and Oncrasin Analogs. Chemically, Oncrasin-1 has the same core structure as indole-3-carbinol, a naturally occurring constituent of many plant foods that has been tested for the prevention and treatment of cancer (Brignall, 2001; Kelloff et al., 1996; Chinni et al., 2001). Oncrasin-1 also has structural similarity to sulindac (Taylor et al., 2000; Sun et al., 2002) and lonidamine (Ravagnan et al., 1999; Papaldo et al., 2003), both of which have been evaluated preclinically and clinically for treatment of cancers. However, indole-3-carbinol, sulindac, and lonidamine did not have any cytotoxic effects in T29, T29Kt1, T29Ht1, and H460 cells at any of the concentrations tested (up to 100 µM; data not shown), suggesting that they have different anticancer spectrums or molecular targets from indole-3-carbinol, sulindac, and lonidamine. Oncrasin compounds also bear a indole core structure as the small-molecule inhibitor of isoprenylcysteine carboxylmethyltransferase (Icmt), 2-[5-(3-methylphenyl)-1-octyl-1H-indol-3-yl]acetamide (cysmethynil), which also induces antitumor activity in Ras gene mutant cancer cells (Winter-Vann et al., 2005). Cysmethynil is reported to induce Icmt-dependent growth inhibition in wild-type mouse embryonic fibroblasts (MEF) but not in Icmt-knockout MEF cells, and block anchorage-independent growth human colon cancer cells (Winter-Vann et al., 2005). Because cysmethynil is not commercially available, the inventors tested whether Oncrasin compounds can induce Icmt-dependent growth inhibition in MEF cells. The result showed that Oncrasin-1 did not induce Icmt-dependent growth inhibition in MEF cells. Both wild-type MEF and Icmt−/− MEF (Bergo et al., 2004) (kindly provided by Dr. S G Young at the University of California, San Francisco) were resistant to Oncrasin-1. At the highest concentration tested (100 µM), Oncrasin-1 only induced similar and mild growth suppression in both cells, suggesting that Oncrasin has different mechanism of action from cysmethynil.

Based on a Chemical Abstract Service database search, the inventors obtained more than 100 analogues of Oncrasin-1. These compounds were either synthesized by the inventors, obtained from ChemBridge Corporation, the National Cancer Institute [NCI] Drug Synthesis and Chemistry Branch, or from various other companies in the United States, Russia, and the Ukraine. More than 30 compounds were identified that induce cytotoxicity in T29Kt1 and H460 cells but not in T29 cells. Of those, more than 20 compounds were similar to or better than Oncrasin-1 in cell killing activity in T29Kt1 and H460 cells. A brief structure/activity relationship (SAR) analysis based on the $IC_{50}$ in these cells showed that a ring structure attached to the indole in Oncrasin-1 is required for its activity, although the ring can be a benzyl ring or a five member ring. Various substitutions in the ring change the $IC_{50}$ in T29Kt1 and H460 cells; however, such changes are quantitative rather than qualitative. Changing of the aldehyde group attached to the indole to ketone or to a carbolic group led to a dramatic reduction of activity, whereas changing it to a hydroxyl group or salts led to an increase in activity without a loss of specificity. The analogues tested and their $IC_{50}$s for T29, T29Kt1, and H460 cells are listed in Table 1. Table 2 shows $IC_{50}$ of some active Oncrasin compounds in various other cancer cells.

A. Compound Synthesis, Purification and Quality Test.

Figure 12:
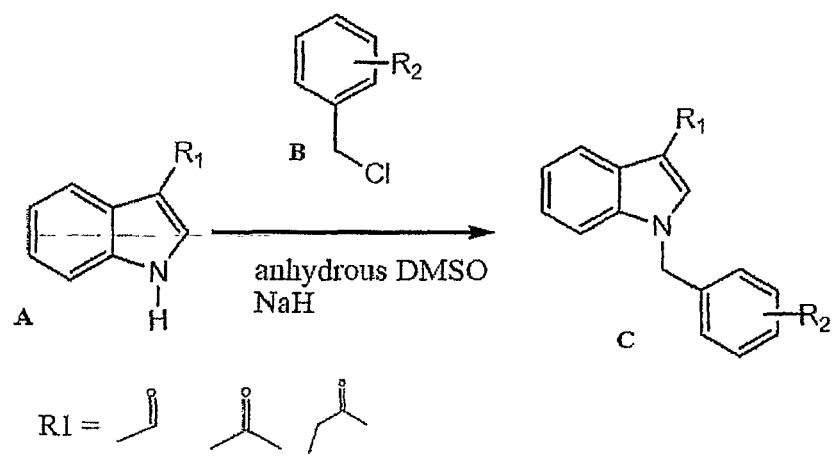
FIG. 12 The synthesis route of Oncrasin analogues. The compound building blocks A (containing indole) and B (benzyl halides) were reacted using NaH as a catalyst.
Figure 13A:
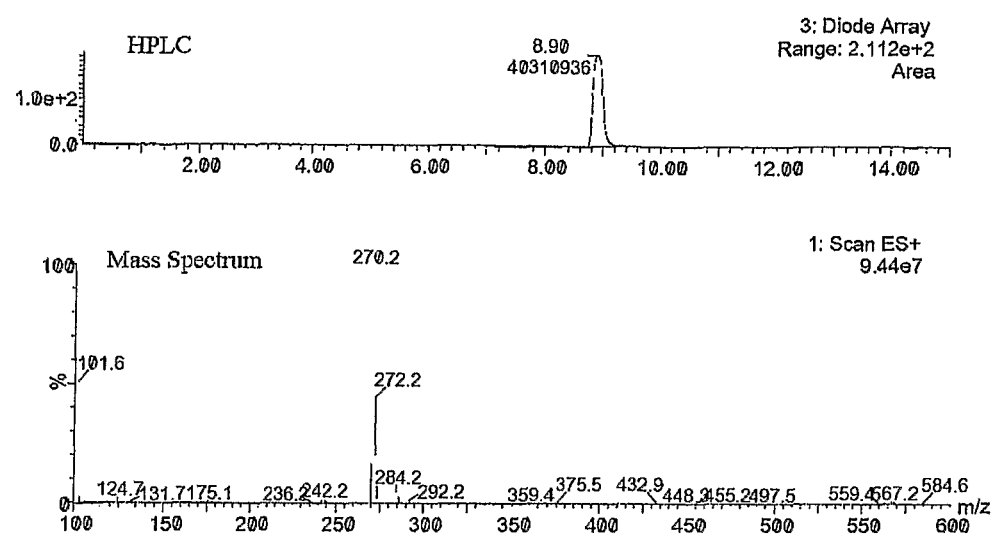
FIGS. 13A and 13B (FIG. 13A) HPLC-MS analysis of Oncrasin-27 after synthesis and purification.
Figure 13B:
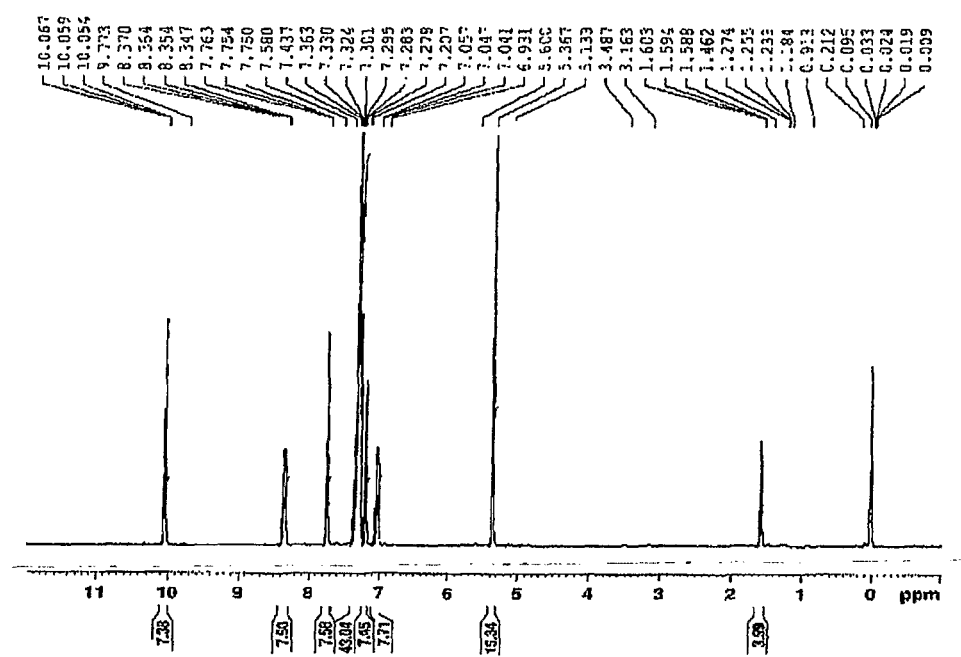

As mentioned herein, many of the compounds studied were obtained from ChemBridge Corporation or from the NCI's Drug Synthesis and Chemistry Branch. The inventors also synthesized several dozens of analogs in their laboratory, e.g., 1-[1-(2-chlorobenzyl)-1H-indol-3-yl]ethanone, 1-[1-(3-chlorobenzyl)-1H-indol-3-yl]ethanone, 1-[1-(4-chlorobenzyl)-1H-indol-3-yl]ethanone, {1-[4-(trifluoromethyl)benzyl]-1H-indol-3-yl}methanol, 1-[3,5-bis(trifluoromethyl)benzyl]-1H-indole-3-carbaldehyde, {1-[3,5-bis(trifluoromethyl)benzyl]-1H-indol-3-yl}methanol, 1-(4-tert-butylbenzyl)-1H-indole-3-carboxylic acid, (1-(4-tert-butylbenzyl)-1H-indol-3-yl)methanol, 1H-Indole-3-carboxaldehyde, 1-[(3-methoxy-4-chlorophenyl)methyl], 1H-Indole-3-methanol, 1-[(3-chloro-4-fluorophenyl)methyl], Methanol, 1-[1-(b-D-glucopyranosyloxy)-1H-indol-3-yl], 1H-Indole-3-methanol,1-(b-D-ribofuranosyloxy), and 1H-Indole-3-biocytin-hydrazide, 1-[(4-chlorophenyl)methyl]-(9CI). Typically, two approaches were used to synthesize new analogs or analogs that are not commercially available. One approach was through reduction by $LiAlH_4$ or $NaBH_4$ or oxidation by $KMnO_4$ of commercially available indole-3-carboxyaldehyde analogs to obtain indole-3-methanol or indole-3-carboxylic acid analogues. The second approach was to synthesize new compounds by using various compound building blocks as shown in FIG. 12. Briefly, 1.0 mmol of building block A (containing indole) was dissolved in anhydrous DMSO and mixed with 1.1 mmol of NaH. After 1 h of stirring at room temperature, 1.2 mmol of building block B (benzyl halides) was added, and the mixture was stirred at room temperature for another 24 h. Then, after the addition of distilled water (3× volume of DMSO), the mixture was extracted with chloroform or dichloromethane. The organic phase was washed with 10% NaCl. The water residue was then removed by adding anhydrous $Na_2SO_4$ which was in turn removed by filtering through a paper filter. The solution was then concentrated by rotary vacuum evaporation. The products were separated and purified by silica gel column chromatography based on the polarity of the compounds, using $CH_2Cl_2$:n-hexane (1:1) or $CHCl_3$:methanol (20:1) as eluents, or by crystallization based on their solubility in various agents. The organic eluents were then removed by vacuum evaporation to obtain the final products. The purity and molecular weight of the final products were determined by high-performance liquid chromatography-mass spectrometry (HPLC-MS) (performed at the Pharmaceutical Development Center of our institution). The identities of the compounds were determined by nuclear magnetic resonance (NMR) analyses. The examples for HPLC-MS and NMR analysis for Oncrasin-27 after synthesis and purification are shown in FIG. 13. Most of the compounds had purity of >95~99%, and their molecular weights matched the predicted molecule, as shown by HPLC-MS. Only compounds with a purity of 95% or higher shown by HPLC-MS were used for testing in cultured cells.

TABLE 1

Oncrasin Analogs and $IC_{50}$ in T29, T29K, or H460 cells.

| COMPOUND CAS # OR IDENTIFIER | | NAME/STRUCTURE | T29 | T29k | H460 |
|---|---|---|---|---|---|
| K001 | 75629-57-1 | 1H-Indole-3-carboxaldehyde, 1-[(4-chlorophenyl)methyl]-(9CI) | >4.5 | 5.6 | 6.6 |
| K002 | 302828-82-6 | 4H-1,2,4-Triazol-4-amine, N-[[1-[(2,4-dichlorophenyl)methyl]-1H-indol-3-yl]methyle> | >4.5 | >4.5 | 4.8 |
| K003 | 302829-20-5 | 1-(2-chlorobenzyl)-1H-indole-3-carbaldehyde N-ethylthiosemicarbazone | >4.5 | >4.5 | 4.75 |
| K004 | 337506-29-3 | N-[2-(1-benzyl-2-methyl-1H-indol-3-yl)ethyl]acetamide | <45 | <45 | <45 |
| K005 | 525-02-0 | [2-(1-benzyl-5-methoxy-2-methyl-1H-indol-3-yl)ethyl]amine hydrochloride | 4.8 | 4.8 | 5.2 |
| K006 | 92407-89-1 | [1-(2-chlorobenzyl)-1H-indol-3-yl]methanol | >4.5 | 5.6 | 7 |
| K007 | 677015-20-2 | 4-[(3-benzoyl-1H-indol-1-yl)methyl]benzonitrile | >4.5 | >4.5 | >4.5 |
| K008 | 3377-71-7 | 1-benzyl-1H-indole | >4.5 | >4.5 | >4.5 |
| K009 | 5102-18-1 | Ethanone, 1-(5-hydroxy-2-methyl-1-phenyl-1H-indol-3-yl)- | >4.5 | >4.5 | >4.5 |
| K010 | 676537-97-6 | (1-benzyl-1H-indol-3-yl)(cyclopropyl)methanone | >4.5 | >4.5 | >4.5 |
| K011 | 609823-07-6 | methyl 5-hydroxy-2-methyl-1-(1-naphthylmethyl)-1H-indole-3-carboxylate | 5.5 | 5.5 | 5.8 |
| K012 | 29957-93-5 | 1H-Indole-3-propanol, 1-(phenylmethyl)- | >4.5 | >4.5 | >4.5 |
| K013 | 2731-06-8 | 2-(2-methyl-1H-indol-3-yl)ethanamine | >4.5 | >4.5 | >4.5 |
| K014 | 10511-51-0 | 1-Benzylindole-3-carboxaldehyde | >4.5 | 5.3 | 7.6 |
| K015 | 487-89-8 | 1H-Indole-3-carboxaldehyde (9CI) | >4.5 | >4.5 | >4.5 |
| K016 | 56344-53-7 | 7H-Pyrrolo[2,3-d]pyrimidin-4-amine, 5,6-dimethyl-7-(phenylmethyl)- | >4.5 | >4.5 | >4.5 |
| K017 | 842975-80-8 | 7H-Pyrrolo[2,3-d]pyrimidin-4-amine, N-[3-(1H-imidazol-1-yl)propyl]-5,6-diphenyl-7- | 4.8 | 5 | >4.5 |
| K018 | 4584-39-8 | 1H-Indole-3-acetic acid, 1-[(4-chlorophenyl)methyl]-5-methoxy-2-methyl- | >4.5 | >4.5 | >4.5 |

TABLE 1-continued

Oncrasin Analogs and IC$_{50}$ in T29, T29K, or H460 cells.

| COMPOUND CAS # OR IDENTIFIER | | NAME/STRUCTURE | T29 | T29k | H460 |
|---|---|---|---|---|---|
| K019 | 173458-80-5 | 7-benzyl-4-chloro-5,6-dimethyl-7H-pyrrolo [2,3-d]pyrimidine1-(3-chlorobenzyl)-1H-indole-3-carbonitrile | >4.5 | >4.5 | >4.5 |
| K020 | 833441-48-8 | | >4.5 | >4.5 | >4.5 |
| K021 | 385382-15-0 | 1-{1-[2-(4-chlorophenyl)ethyl]-5-hydroxy-2-methyl-1H-indol-3-yl}ethanone | >4.5 | >4.5 | >4.5 |
| K022 | 342398-67-8 | 3-acetyl-1-[2-(3,4-dimethoxyphenyl)ethyl]-2-methyl-1H-indol-5-yl 2-furoate | >4.5 | >4.5 | >4.5 |
| K023 | 432008-82-7 | methyl 1-[(4-methoxyphenyl)acetyl]-1H-indole-3-carboxylate | >4.5 | >4.5 | >4.5 |
| K024 | 583818-66-0 | 5-{[1-(3,4-dichlorobenzyl)-1H-indol-3-yl]methylene}-2,4-imidazolidinedione | >4.5 | >4.5 | >4.5 |
| K025 | 151409-77-7 | 1-(1-naphthylmethyl)-1H-indole-3-carbaldehyde | >4.5 | >4.5 | >4.5 |
| K026 | 331869-66-0 | ethyl 5-hydroxy-1-[2-hydroxy-2-(4-nitrophenyl)ethyl}-2-methyl-1H-benzo[g]indole-3 | >4.5 | >4.5 | >4.5 |
| K027 | 90815-01-3 | 1-(3-chlorobenzyl)-1H-indole-3-carbaldehyde | >4.5 | 6.43 | 8.43 |
| K028 | 90815-00-2 | 1-(2-chlorobenzyl)-1H-indole-3-carbaldehyde | >4.5 | >4.5 | >4.5 |
| K029 | 174367-70-5 | 1-(4-bromobenzyl)-1H-indole-3-carbaldehyde | >4.5 | 5 | >4.5 |
| K030 | 27018-76-4 | 1-benzyl-1H-indole-3-carboxylic acid | >4.5 | >4.5 | >4.5 |
| K031 | 155883-86-6 | Hydrazinecarbothioamide, 2-[[1-(phenylmethyl)-1H-indol-3-yl]methylene]-(9CI) | >4.5 | 5 | >4.5 |
| K032 | 146-82-7 | 1H-Indole-3-acetic acid, 1-[(4-chlorophenyl)methyl]-5-methyl-2-phenyl-(9CI) | >4.5 | >4.5 | >4.5 |
| K033 | 500726-45-4 | 1H-1,2,3-Triazolo[4,5-b]pyrazine, 5,6-dichloro-(9CI) | >4.5 | >4.5 | >4.5 |
| K034 | 93548-92-6 | 1H-Indole-3-carboxylic acid, 2-chloro-1-[(2,4-dichlorophenyl)methyl]-(9CI) | >4.5 | >4.5 | >4.5 |
| K035 | NSC131904 | IUPAC: (6-bromo-3-methyl-2,3-dihydroindol-1-yl)-phenyl-methanone | >4.5 | >4.5 | >4.5 |
| K036 | 94005-21-7 | Indole-3-acetic acid, 1-benzyl-5-methoxy-(6CI,7CI) | >4.5 | >4.5 | >4.5 |
| K037 | NSC66574 | IUPAC: 2-[1-[(4-chlorophenyl)methyl]-2-ethyl-5-methyl-indol-3-yl]acetic acid | >4.5 | >4.5 | >4.5 |
| K038 | NSC74617 | IUPAC: 2-[1-[(4-chlorophenyl)methyl]-2-ethyl-5-methyl-indol-3-yl]acetic acid | >4.5 | >4.5 | >4.5 |
| K039 | NSC66575 | IUPAC: 2-[1-[(4-chlorophenyl)methyl]-5-methoxy-2-(4-methoxyphenyl)-indol-3-IUPAC: 2-[1-[(4-chlorophenyl)methyl]-5-methoxy-2-(4-methoxyphenyl)-indol-3-methoxyphenyl)-indol-3- | >4.5 | >4.5 | >4.5 |
| K040 | NSC77541 | IUPAC: 2-[1-(4-chlorobenzoyl)-5-methoxy-2-methyl-indol-3-yl]acetic acid | >4.5 | >4.5 | >4.5 |
| K041 | NSC674196 | IUPAC: tert-butyl 2-amino-1-benzyl-7a-methyl-5-oxo-indole-3-carboxylate | 5.3 | 5.3 | >4.5 |
| K042 | 28558-66-9NSC54775 | Sulfanilamide, N4-[(1-benzylindol-3-yl)methylene]-N1-2-thiazolyl-(8CI) | >4.5 | 6 | 8 |
| K043 | | IUPAC: 2-(1-benzyl-5-methoxy-2-methyl-indol-3-yl)acetamide | >4.5 | >4.5 | >4.5 |
| K044 | | IUPAC: 2-chloro-N-[5-[(4-chloro-2-methyl-phenyl)carbamoylmethyl]-4-oxo-1,3-thiazol-2-yl]-benzamide | >4.5 | >4.5 | >4.5 |
| K045 | NSC17383 | IUPAC: 2-[1-[(2-chlorophenyl)methyl]-2-methyl-5-methylsulfanyl-indol-3-yl]ethanamine | >4.5 | >4.5 | >4.5 |
| K046 | 25791-28-0 | 2-Indolinone, 1-benzyl-3-(2-pyridylmethylene)-(8CI) | 5.3 | 5.3 | >4.5 |
| K047 | 109448-43-3 | Indoxyl, 1-benzyl-, acetate (6CI) | >4.5 | 4.5 | 5 |
| K048 | NSC99693 | IUPAC: ethyl 2-(1-benzyl-3-hydroxy-2-oxo-indol-3-yl)acetate | >4.5 | >4.5 | >4.5 |
| K049 | 92407-93-7 | [1-(3,4-dichlorobenzyl)-1H-indol-3-yl]methanol | >4.5 | 6.5 | 7.5 |
| K050 | 90815-03-5 | 1-(2,4-dichlorobenzyl)-1H-indole-3-carbaldehyde | >4.5 | 5.8 | 7 |

TABLE 1-continued

Oncrasin Analogs and IC$_{50}$ in T29, T29K, or H460 cells.

| COMPOUND CAS # OR IDENTIFIER | | NAME/STRUCTURE | T29 | T29k | H460 |
|---|---|---|---|---|---|
| K051 | 1192997-17-4 | 1-(2-fluorobenzyl)-1H-indole-3-carbaldehyde | >4.5 | 6.5 | 7 |
| K052 | 420814-87-5 | 1-(2-chloro-6-fluorobenzyl)-1H-indole-3-carbaldehyde | >4.5 | >4.5 | >4.5 |
| K053 | 93548-80-2 | 1-(2,6-dichlorobenzyl)-1H-indole-3-carbaldehyde | >4.5 | >4.5 | >4.5 |
| K054 | 50264-69-2 | 1H-Indazole-3-carboxylic acid, 1-[(2,4-dichlorophenyl)methyl]-(9CI) (Lonidamine) | >4.5 | >4.5 | >4.5 |
| K055 | 38194-50-2 | 1H-Indene-3-acetic acid, 5-fluoro-2-methyl-1-[[4-(methylsulfinyl)phenyl]methylene] | >4.5 | >4.5 | >4.5 |
| K056 | 63804-15-9 | 1H-Indene-3-acetic acid, 5-fluoro-2-methyl-1-[[4-(methylsulfinyl)phenyl]methylene] | >4.5 | >4.5 | >4.5 |
| K057 | SW1 | ACD: 1-[1-(2-chlorobenzyl)-1H-indol-3yl]ethanone | >4.5 | >4.5 | >4.5 |
| K058 | SW2 | ACD: 1-[1-(3-chlorobenzyl)-1H-indol-3-yl]ethanone | >4.5 | 4.5 | >4.5 |
| K059 | SW3 | ACD: 1-[1-(4-chlorobenzyl)-1H-indol-3-yl]ethanone | >4.5 | >4.5 | >4.5 |
| K060 | 92407-91-5 | 1H-Indole-3-methanol, 1-[(4-chlorophenyl)methyl]- | >4.5 | 7.1 | 7.8 |
| K61 | 93548-89-1 | 1H-Indole-3-carboxylic acid, 1-[(4-chlorophenyl)methyl]-(9CI) | >4.5 | >4.5 | >4.5 |
| K62 | 192997-22-1 | 1-[3-(trifluoromethyl)benzyl]-1H-indole-3-carbaldehyde | >4.5 | 5.25 | 7.86 |
| K63 | R4-OH-3-CF3 | ACD: {1-[3-(trifluoromethyl)benzyl]-1H-indol-3-yl}methanol | >4.5 | 6.25 | 7.4 |
| K64 | 501660-56-6 | 1H-Indole-3-carboxaldehyde, 1-[[4-(trifluoromethyl)phenyl]methyl]-(9CI) | >4.5 | >4.5 | 5.8 |

TABLE 1-continued

Oncrasin Analogs and IC$_{50}$ in T29, T29K, or H460 cells.

| COMPOUND CAS # OR IDENTIFIER | NAME/STRUCTURE | T29 | T29k | H460 |
|---|---|---|---|---|
| K65 | SW7 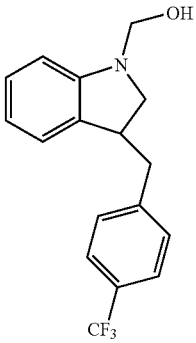 {1-[4-(trifluoromethyl)benzyl]-1H-indol-3-yl}methanol | >4.5 | 5.9 | 5.9 |
| K66 | 151409-79-9 1H-Indole-3-carboxaldehyde, 1-[(4-methylphenyl)methyl]- | 4.5 | 5.4 | 7.2 |
| K67 | 664317-83-3 1H-Indole-3-methanol, 1-[(4-methylphenyl)methyl]-(9CI) | 4.8 | 6.1 | 7 |
| K68 | 591210-47-8 1-(3-nitrobenzyl)-1H-indole-3-carbaldehyde | 4.5 | 6.3 | 7.4 |
| K69 | 678182-31-5 1H-Indole-3-methanol, 1-[(3-nitrophenyl)methyl]- | >4.5 | 6.4 | 7.4 |
| K70 | 192997-25-4 1-(4-nitrobenzyl)-1H-indole-3-carbaldehyde | >4.5 | 5 | 6.3 |
| K71 | 678551-69-4 1H-Indole-3-methanol, 1-[(4-nitrophenyl)methyl]- | >4.5 | 6.8 | 7.1 |
| K27 | 90815-01-3 1-(3-chlorobenzyl)-1H-indole-3-carbaldehyde | >4.5 | 4.5 | 7 |
| K72 | 92407-90-4 1H-Indole-3-methanol, 1-[(3-chlorophenyl)methyl]-(9CI) | >4.5 | 5.75 | 5.9 |
| K29 | 174367-70-5 1-(4-bromobenzyl)-1H-indole-3-carbaldehyde | >4.5 | 6.6 | 8.5 |
| K73 | 210426-43-0 1H-Indole-3-methanol, 1-{(4-bromophenyl)methyl]-(9CI) | >4.5 | 6.4 | 9.5 |
| K50 | 90815-03-5 1-(2,4-dichlorobenzyl)-1H-indole-3-carbaldehyde | >4.5 | 5 | 6.3 |
| K74 | 92407-92-6 1H-Indole-3-methanol, 1-[(2,4-dichlorophenyl)methyl]- | >4.5 | 5.8 | 7.1 |
| K75 | 93548-82-4 1H-Indole-3-carboxaldehyde, 1-[(3,5-dichlorophenyl)methyl]-(9CI) | >4.5 | >4.5 | >4.5 |
| K76 | SW23 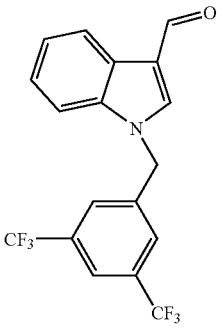 1-[3,5-bis(trifluoromethyl)benzyl]-1H-indole-3-carbaldehyde | 5.2 | 5.4 | 5.9 |

TABLE 1-continued
Oncrasin Analogs and IC$_{50}$ in T29, T29K, or H460 cells.
| COMPOUND CAS # OR IDENTIFIER | NAME/STRUCTURE | T29 | T29k | H460 |
|---|---|---|---|---|
| K77  SW24 | 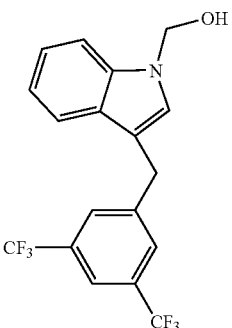<br>{1-[3,5-bis(trifluoromethyl)benzyl]-1H-indol-3-yl}methanol | 5.2 | 5.1 | 5.1 |
| K078  SW25 | 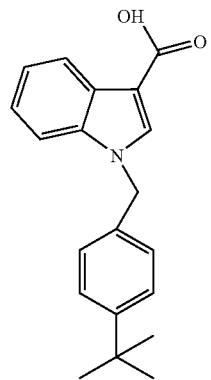<br>1-(4-tert-butylbenzyl)-1H-indole-3-carboxylic acid | | | |
| K079  SW26 | 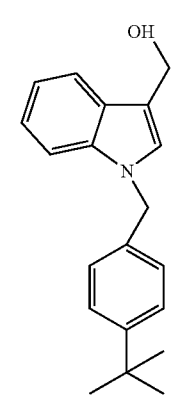<br>(1-(4-tert-butylbenzyl)-1H-indol-3-yl)methanol | | | |
| K080  781589-99-9 | 1H-indole-3-ethanamine, 1-[(2-methylphenyl)methyl]- | | | |

TABLE 1-continued
Oncrasin Analogs and IC$_{50}$ in T29, T29K, or H460 cells.
| COMPOUND CAS # OR IDENTIFIER | NAME/STRUCTURE | T29 | T29k | H460 |
|---|---|---|---|---|
| K081 SW28 | 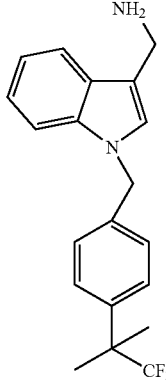<br>1H-indol-3-ethanamine, 1-[[3-(trifluoromethyl)phenyl]methyl]- | | | |
| K082 SW29 | 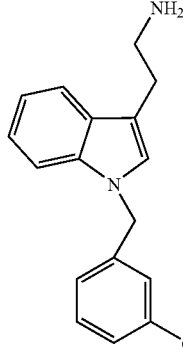<br>1H-indole-3-ethanamine, 1-[(3-chlorophenyl)methyl]- | | | |
| K83 SW30 | 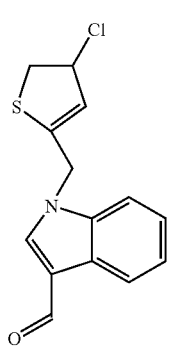<br>1H-indole-3-carboxaldehyde, 1-[(5-chloro-2-thienyl)methyl]- | | | |

TABLE 1-continued

Oncrasin Analogs and IC$_{50}$ in T29, T29K, or H460 cells.

| COMPOUND CAS # OR IDENTIFIER | NAME/STRUCTURE | T29 | T29k | H460 |
|---|---|---|---|---|
| K84   SW31 | 1H-Indole-3-carboxaldehyde, 1-[(3-chloro-4-fluorophenyl)methyl]- | | | |
| K85   SW32 | 1H-Indole-3-carboxaldehyde, 1-[(3-chloro-4-methoxyphenyl)methyl]- | | | |
| K86   SW33 | 1H-Indole-3-carboxaldehyde, 1-[(3-methoxy-4-chlorophenyl)methyl]- | | | |
| K87   SW34 | 1H-Indole-3-methanol, 1-[(3-chloro-4-fluorophenyl)methyl]- | | | |

TABLE 1-continued

Oncrasin Analogs and IC$_{50}$ in T29, T29K, or H460 cells.

| COMPOUND CAS # OR IDENTIFIER | | NAME/STRUCTURE | T29 | T29k | H460 |
|---|---|---|---|---|---|
| K88 | SW35 | [structure: 1-(4-chlorobenzyl)-1H-indole-3-carboxylic acid] | | | |
| K89 | 10511-51-0 | 1H-Indole-3-carboxaldehyde, 1-(phenylmethyl)- | | | |
| K90 | 53-85-0 | 1H-Benzimidazole, 5,6-dichloro-1-b-D-ribofuranosyl- | >4.5 | >4.5 | >4.5 |
| K91 | Chemistry 14 | [structure: 1-(β-D-ribofuranosyl)-3-(hydroxymethyl)-1H-indole] | | | |
| K92 | 121103-34-2 | 1H-Indole-3-carboxaldehyde, 5-bromo-1-(phenylmethyl)- | | | |
| K93 | 593235-84-8 | 1H-Indole-3-carboxaldehyde, 5-bromo-1-[(3-chlorophenyl)methyl]- | | | |
| K94 | 713085-30-4 | 1-Propanone, 1-[1-[(4-chlorophenyl)methyl]-1H-indol-3-yl]- | | | |
| K95 | 92407-86-8 | 1H-Indole-3-carboxaldehyde, 1-[(4-chlorophenyl)methyl]-2-methyl- | | | |
| K96 | 593236-94-3 | 1H-Indole-3-carboxaldehyde, 1-[(3-chlorophenyl)methyl]-7-ethyl- | | | |
| K97 | 664317-83-3 | 1H-Indole-3-methanol, 1-[(4-methylphenyl)methyl]- | | | |
| K98 | 420811-32-1 | 1H-Indole-3-carboxylic acid, 1-(4-chlorobenzoyl)-, methyl ester | | | |
| K99 | 592546-71-9 | Benzoic acid, 4-[(3-formyl-1H-indol-1-yl)methyl]- | | | |
| K100 | 340318-80-1 | 1H-Indole-3-carboxaldehyde, 1-[2-(2-chlorophenoxy)ethyl]- | | | |
| K101 | 885526-36-3 | 1H-Indole-3-methanol, 5-methoxy-1-(phenylmethyl)- | | | |
| K102 | 677345-08-3 | Methanone, cyclopropyl[1-[(3,4-dichlorophenyl)methyl]-1H-indol-3-yl]- | | | |
| K103 | 676247-82-8 | 1H-Indole-3-methanol, 1-(1-naphthalenylmethyl)- | | | |
| K104 | 59121047-8 | 1H-Indole-3-carboxaldehyde, 1-[(3-nitrophenyl)methyl]- | | | |
| K105 | 40158042-5 | 1H-Indole-3-carboxylic acid, 1-(4-fluorobenzoyl)-, methyl ester | | | |
| K106 | 487-60-5 | b-D-Glucopyranoside, 1H-indol-3-yl | | | |
| K107 | Chemistry 15 | Methanol, 1-[1-(b-D-glucopyranosyloxy)-1H-indol-3-yl]- | | | |
| K108 | 34365-14-5 | Ethanone, 1-[1-(b-D-glucopyranosyloxy)-1H-indol-3-yl]- | | | |
| K109 | 754199-86-5 | 1H-Indole-3-carboxylic acid, 1-[(2,4-dichlorophenyl)methyl]-, methyl ester | | | |
| K110 | 412284-65-2 | 1H-Indole-3-carboxaldehyde, 5-chloro-1-methyl- | | | |
| K111 | 329061-82-7 | 1H-Indole-3-carboxaldehyde, 1-[2-(4-chlorophenoxy)ethyl]- | | | |
| K112 | 833441-48-8 | 1H-Indole-3-carbonitrile, 1-[(3-chlorophenyl)methyl]- | | | |
| K113 | 155134-26-2 | 1H-Indole-3-carboxylic acid, 1-(phenylmethyl)-, methyl ester | | | |
| K114 | 29957-93-5 | 1H-Indole-3-propanol, 1-(phenylmethyl)- | | | |
| K115 | 299936-51-9 | 1H-Indole-3-carboxaldehyde, 1-(2-phenoxyethyl)- | | | |
| K116 | 22948-94-3 | 1H-Indole-3-carboxaldehyde, 1-acetyl- | | | |
| K117 | 773101-94-3 | 1H-Indole, 3-(1,3-dioxolan-2-yl)-1-(phenylmethyl)- | | | |
| K118 | 5414-45-9 | Quinoline, 1-[(4-chlorophenyl)methyl]-1,2,3,4-tetrahydro- | | | |

TABLE 1-continued

Oncrasin Analogs and IC$_{50}$ in T29, T29K, or H460 cells.

| COMPOUND CAS # OR IDENTIFIER | | NAME/STRUCTURE | T29 | T29k | H460 |
|---|---|---|---|---|---|
| K119 | 10745642-8 H | Benzimidazole, 1-p-chlorobenzyl- | | | |
| K120 | 862652-44-6 | 1H-Indole-3-carboxaldehyde, 1-{2-(1-naphthalenyloxy)ethyl]- | | | |
| K121 | 89542-38-1 | Benzothiazolium, 3-[(4-chlorophenyl)methyl]-, bromide | | | |
| K122 | 906345-77-5 | Glucosiduronic acid, 3-carboxyindolyl | | | |
| K123 | 4958-11-6 | Indoline, 1-glucopyranosyl- | | | |
| K124 | 400782-50-5 | 1H-Indole, 1-(b-D-glucopyranosyloxy)-5-nitro- | | | |
| K125 | 444794-70-1 | 1H-Indole, 1-[(2-deoxy-b-D-erythro-pentofuranosyl)oxy]-4-methyl- | | | |
| K126 | Chemistry 16 | 1H-Indole-3-methanol, 1-(b-D-ribofuranosyloxy)- | | | |
| K127 | 400782-53-8 | 1H-Indole, 5-nitro-1-(b-D-ribofuxanosyloxy)- | | | |
| K128 | 78434-21-6 | 1H-Benzimidazole-2-carbonitrile, 1-(b-D-glucopyranosyloxy)- | | | |
| K129 | 207598-26-3 | b-D-Galactopyranoside, 1-methyl-1H-indol-3-yl | | | |
| K130 | SW37 Biotin | 1H-Indole-3-biocytin-hydrazide, 1-[(4-chlorophenyl)methyl]-(9CI) | >4.5 | 5.6 | 6.4 |

TABLE 2

Activity in different cell lines (IC$_{50}$ (−LogM))

| Cell Lines | Cancers | OnK-1 | OnK-60 | OnK62 | Onk63 | OnK68 | Onk69 | OnK71 | Onk29 |
|---|---|---|---|---|---|---|---|---|---|
| H460 | Lung | 6.6 | 7.8 | 7.8 | 7.4 | 7.4 | 7.4 | 7.1 | 8.5 |
| H226B | Lung | 7 | 8.6 | 5.5 | 6.5 | 8.6 | 7.5 | 6.5 | 7.1 |
| H226B | Lung | 5.6 | 8.5 | 5 | 5.8 | 7.2 | 7 | 5.8 | 5.5 |
| A549 | Lung | >4.5 | 5.7 | 5 | >4.5 | 5.3 | >4.5 | >4.5 | >4.5 |
| A549CK8 | Lung | 5.8 | 6 | 5.1 | 5 | 5.5 | 5.9 | 5.1 | 5.5 |
| Hct116 | Colon | 5.5 | 7 | 4.9 | 5.1 | 6.8 | 6.5 | 5.5 | 5.6 |
| CT116P53 | Colon | >4.5 | >4.5 | >4.5 | >4.5 | >4.5 | >4.5 | >4.5 | >4.5 |
| HKE3 | Colon | 6.4 | 7.6 | 5.5 | 6 | 7 | 7.1 | 6.4 | 7 |
| HKE3 | Colon | 6 | >8.5 | 5.3 | 5.8 | 6.4 | 6 | 6.7 | 6.3 |
| H322 | Lung | 4.5 | 4.5 | 5 | 4.5 | 4.5 | >4.5 | >4.5 | 4.5 |
| h1299 | Lung | >4.5 | 5.5 | 5 | >4.5 | 5 | >4.5 | 5 | 4.9 |
| ASPC1 | Pancrease | 5.5 | 5.7 | 4.8 | 5 | 5.7 | 5.1 | 5 | 5.4 |
| DLD1 | Colon | >4.5 | >4.5 | >4.5 | >4.5 | >4.5 | >4.5 | >4.5 | >4.5 |
| Heb46 | Kidney | 6.1 | 6.7 | 5 | 5 | 6.7 | 6.5 | 5.4 | 6.6 |
| Heb44 | Kidney | 8 | 8 | 7 | 6.6 | 8 | 7.1 | 6.8 | 8.1 |
| capanc1 | Pancrease | 5 | 5 | 4.5 | 4.5 | 4.5 | 4.5 | 6.9 | 6 |
| Sw620 | Colon | 5.4 | 5.3 | >4.5 | >4.5 | 4.5 | 4.5 | 4.5 | 4.5 |
| miapac | Pancrease | >4.5 | >4.5 | >4.5 | >4.5 | >4.5 | >4.5 | >4.5 | >4.5 |
| H2122 | Lung | 6.1 | 6 | | 6 | 5.7 | 5.5 | 5.7 | |
| H2009 | Lung | >4.5 | 4.8 | | | 4.5 | >4.5 | >4.5 | >4.5 |
| H23 | Lung | >4.5 | 4.8 | | | 4.5 | 4.5 | 4.5 | 4.5 |
| H1933 | Lung | >4.5 | 5 | | | 4.6 | >4.5 | 4.5 | 4.5 |
| H1395 | Lung | >4.5 | 4.7 | | | >4.5 | >4.5 | >4.5 | 4.5 |
| H2087 | Lung | >4.5 | 4.6 | | | 4.5 | 4.5 | >4.5 | 4.5 |

TABLE 2-continued

| Activity in different cell lines (IC$_{50}$ (−LogM)) | | | | | | | | |
|---|---|---|---|---|---|---|---|---|
| Ovcar3 | Ovary | 5.6 | 7 | | 6.8 | 6.6 | 5.6 | 5.3 |
| Ovcar443 | Ovary | 4.5 | 5.6 | | 5 | >4.5 | | 5 |
| Hey | Ovary | 4.6 | 5 | | >4.5 | >4.5 | 4.5 | 4.5 |
| Ovca429 | Ovary | 4.5 | 4.5 | | 4.5 | 4.5 | | 5.5 |
| SKOV3 | Ovary | 5.8 | 6.2 | | 6 | 5.5 | | 5.5 |

| Cell Lines | Cancers | OnK73 | OnK42 | OnK6 | OnK49 | OnK29 | OnK51 | Onk27 | OnK14 |
|---|---|---|---|---|---|---|---|---|---|
| H460 | Lung | 8.5 | 8 | 7 | 7.5 | 8.5 | 7 | 8.4 | 7.6 |
| H226B | Lung | 7 | 5.5 | 8.6 | 8.6 | 6.9 | 6.1 | 6.5 | 5.7 |
| H226B | Lung | 5.8 | 5.3 | 7.4 | 8.5 | 5.3 | 5 | 5.4 | 4.5 |
| A549 | Lung | >4.5 | 5 | 4.9 | 5 | 5 | 4.9 | 5 | 4.5 |
| A549CK8 | Lung | 5.5 | 5.3 | 5.4 | 5.2 | 5.5 | 5 | 4.8 | 5.2 |
| Hct116 | Colon | 5.5 | 5 | 6.3 | 8 | 5.5 | 5 | 5.4 | 5.1 |
| CT116P53 | Colon | >4.5 | >4.5 | >4.5 | >4.5 | >4.5 | >4.5 | >4.5 | >4.5 |
| HKE3 | Colon | 6.5 | 6 | 6.9 | 8.6 | 6.6 | | 6 | 6 |
| HKE3 | Colon | 6.1 | 5 | 6.6 | 8.5 | 5.8 | 5 | 5.9 | 5.3 |
| H322 | Lung | >4.5 | >4.5 | 4.5 | 5 | 4.5 | >4.5 | >4.5 | >4.5 |
| h1299 | Lung | >4.5 | >4.5 | 5 | 5 | 5.1 | 5.1 | 4.8 | >4.5 |
| ASPC1 | Pancrease | 5.5 | 5 | 5.4 | 5 | 5.3 | 5.1 | 4.8 | 5.1 |
| DLD1 | Colon | >4.5 | >4.5 | >4.5 | >4.5 | >4.5 | >4.5 | >4.5 | >4.5 |
| Heb46 | Kidney | 6.1 | 5.4 | 5.7 | 7.5 | 5.6 | 5 | 5.7 | 5.5 |
| Heb44 | Kidney | 7.4 | 6.7 | 8 | 8 | 7.2 | 6.5 | 7.2 | 6.3 |
| capanc1 | Pancrease | 5.5 | 5.5 | 4.9 | 4.9 | 5 | 4.5 | 4.5 | 4.5 |
| Sw620 | Colon | >4.5 | >4.5 | 5 | >4.5 | >4.5 | >4.5 | >4.5 | >4.5 |
| miapac | Pancrease | >4.5 | >4.5 | >4.5 | >4.5 | >4.5 | >4.5 | >4.5 | >4.5 |
| H2122 | Lung | 5.6 | | 5.4 | 6.5 | | | 6.2 | |
| H2009 | Lung | >4.5 | | 4.5 | 5 | | | >4.5 | |
| H23 | Lung | 4.5 | | 4.6 | 4.8 | | | >4.5 | |
| H1933 | Lung | 4.5 | | 4.8 | 4 | | | >4.5 | |
| H1395 | Lung | >4.5 | | 4.5 | 4.8 | | | >4.5 | |
| H2087 | Lung | 4.5 | | 4.6 | 5.1 | | | >4.5 | |
| Ovcar3 | Ovary | 5.9 | | 6.2 | 8 | | | 5.5 | |
| Ovcar443 | Ovary | 4.8 | | 5.1 | 5 | | | | |
| Hey | Ovary | 4.5 | | 4.5 | | | | | |
| Ovca429 | Ovary | 5.5 | | 5 | 5.1 | | | | |
| SKOV3 | Ovary | 5.5 | | 5.4 | 5.5 | | | | |

B. Chemical Formulas of Oncrasin Compounds

Chemical formulas of the Oncrasin compounds can be generally defined by the general formula or structure of Formula I.

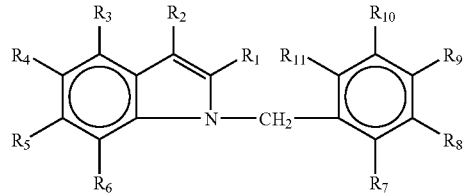

Formula I

In certain embodiments, the groups $R_1$, $R_2$, $R_3$, $R_4$, $R_5$, $R_6$, $R_7$, $R_8$, $R_9$, $R_{10}$, and/or $R_{11}$ are each independently —H, hydroxy, amino, cyano, halo, bromo, chloro, nitro, mercapto, or substituted or unsubstituted versions of $C_1$-$C_{15}$-alkyl, $C_2$-$C_{15}$-alkenyl, $C_2$-$C_{15}$-al/ynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_1$-$C_{15}$-heteroaralkylamino, $C_2$-$C_{15}$-amido, $C_1$-$C_{15}$-alkylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, or $C_0$-$C_{15}$-silyl.

In certain embodiments, $R_1$, $R_2$, $R_3$, $R_4$, $R_5$, $R_6$, $R_7$, $R_8$, $R_9$, $R_{10}$, and/or $R_{11}$ are substituted or unsubstituted versions of alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkyloxy, acyloxy, alkylamino, alkenylamino, alkynylamino, arylamino, aralkylamino, heteroarylamino, heteroaralkylamino, or amido.

In certain aspects, $R_1$, $R_2$, $R_3$, $R_4$, $R_5$, $R_6$, $R_7$, $R_8$, $R_9$, $R_{10}$, and/or $R_{11}$ are each independently —H, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$C(CH$_3$)$_3$, —C$_6$H$_5$, —C$_6$H$_4$CH$_3$, —C$_6$H$_4$CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)$_2$, —C$_6$H$_3$(CH$_3$)CH$_2$CH$_3$, F, Cl, Br, I, —OH, —OCH$_3$, —OCH$_2$CH$_3$, —OCH$_2$CH$_2$CH$_3$, —OCH(CH$_3$)$_2$, —OCH(CH$_2$)$_2$, —OCH$_2$CF$_3$, —OCOCH$_3$, —OC$_6$H$_5$, —NH$_2$, —NHCH$_3$, —NHCH$_2$CH$_3$, —NHCH$_2$CH$_2$CH$_3$, —NHCH(CH$_3$)$_2$, —NHCH(CH$_2$)$_2$, —N(CH$_3$)$_2$, —N(CH$_3$)CH$_2$CH$_3$, —N(CH$_2$CH$_3$)$_2$, —NHCOCH$_3$, —NHCO$_2$C(CH$_3$)$_3$, —CH$_2$F, —CH$_2$Cl, —CH$_2$Br, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH(CH$_2$)$_2$, —CH$_2$OCH$_2$CF$_3$, —CH$_2$OCOCH$_3$, —CH$_2$NH$_2$, —CH$_2$NHCH$_3$, —CH$_2$N(CH$_3$)$_2$, —CH$_2$NHCH$_2$CH$_3$, —CH$_2$N(CH$_3$)CH$_2$CH$_3$, —CH$_2$NHCH$_2$CH$_2$CH$_3$, —CH$_2$NHCH(CH$_3$)$_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_7$CH$_2$I, —CH$_2$CH$_2$OH, CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH₂CH₂NHCH(CH₂)₂, —CH₂CH₂N(CH₂CH₃)₂, —CH₂CH₂NHCO₂C(CH₃)₃, —CH₂CH=CH₂, —CH₂CH=CHCH₃, —CH₂CH=CHCH₂CH₃, —CH₂CH=CHCH₂CH₂CH₃, —CH₂CH=CHCH(CH₃)₂, —CH₂CH=CHCH(CH₂)₂, —CF₃, —CN, —CH=CH₂, —CH=CHCH₃, —COH, —COCH₃, —COCH₂CH₃, —COCH₂CH₂CH₃, —COCH(CH₃)₂, —COCH(CH₂)₂, —COCH₂CF₃, —COC₆H₅, —COC₆H₄CH₃, —COC₆H₄CH₂CH₃, —COC₆H₄CH₂CH₂CH₃, —COC₆H₄CH(CH₃)₂, —COC₆H₄CH(CH₂)₂, —COC₆H₃(CH₃)₂, —CO₂H, —CO₂CH₃, —CO₂CH₂CH₃, —CO₂CH₂CH₂CH₃, —CO₂CH(CH₃)₂, —CO₂CH(CH₂)₂, —CONH₂, —CONHCH₃, —CONHCH₂CH₃, —CONHCH₂CH₂CH₃, —CONHCH(CH₃)₂, —CONHCH(CH₂)₂, —CON(CH₃)₂, —CON(CH₂CH₃)CH₃, —CON(CH₂CH₃)₂, —CONHCH₂CF₃, —C₆H₄CH=CH₂, —C₆H₄CH=CHCH₃, —C₆H₄F, —C₆H₄Cl, —C₆H₄Br, —C₆H₄I, —C₆H₄OH, —C₆H₄OCH₃, —C₆H₄OCH₂CH₃, —C₆H₄OCOCH₃, —C₆H₄OC₆H₅, —C₆H₄NH₂, —C₆H₄NHCH₃, —C₆H₄NHCH₂CH₃, —C₆H₄CH₂Cl, —C₆H₄CH₂Br, —C₆H₄CH₂OH, —C₆H₄CH₂OCOCH₃, —C₆H₄CH₂NH₁₂, —C₆H₄N(CH₃)₂, —C₆H₄CH₂Cl, —C₆H₄CH₂OH, —C₆H₁CH₂CH₂OCH₃, —C₆H₄CH₂CH₂NH₂, —C₆H₄CH₂CH=CH₂, —C₆H₄CF₃, —C₆H₄CN, —C₆H₄C≡CH, —C₆H₄C≡CCH₃, —C₆H₄C≡CSi(CH₃)₃, —C₆H₄COH, —C₆H₁COCH₃, —C₆H₄COCH₂CH₃, —C₆H₄COCH₂CF₃, —C₆H₄COC₆H₅, —C₆H₄CO₂H, —C₆H₄CO₂CH₃, —C₆H₄CONH₂, —C₆H₄CONHCH₃, —C₆H₄CON(CH₃)₂, —SH, —SCH₃, —SC₆H₅, —SCH₂C₆H₅, or —SCOCH₃.

The letter "n", in a formula or structure can be 0, 1, 2, 3, 4, 5, or 6.

As used herein, the term "amino" means —NH₂; the term "nitro" means —NO₂; the term "halo" designates —F, —Cl, —Br or —I; the term "mercapto" means —SH; the term "cyano" means —CN; the term "silyl" means —SiH₃, and the term "hydroxy" means —OH.

The term "substituted," when used to modify a class of organic radicals (e.g., alkyl, aryl, acyl, etc.), means that one or more than one hydrogen atom of that radical has been replaced by a heteroatom, or a heteroatom containing group. Specific substituted organic radicals are defined more fully below.

The term "unsubstituted," when used to modify a class of organic radicals (e.g., alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group substituted. For example, the group —C₆H₄C=CH is an example of an unsubstituted aryl group, while —C₆H₄F is an example of a substituted aryl group. Specific unsubstituted organic radicals are defined more fully below.

The term "unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, an unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl substituted cycloalkyl groups, and cycloalkyl substituted alkyl groups. The groups, —CH₃, —CH₂CH₃, —CH₂CH₂CH₃, —CH(CH₃)₂, —CH(CH₂)₂, —CH₂CH₂CH₂CH₃, —CH(CH₃)CH₂CH₃, —CH₂CH(CH₃)₂, —C(CH₃)₃, and —CH₂C(CH₃)—₃, are all examples of unsubstituted alkyl groups.

The term "substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a substituted $C_1$-$C_{10}$-alkyl has 1 to 10 carbon atoms. The following groups are all examples of substituted alkyl groups: trifluoromethyl, —CH₂F, —CH₂Cl, —CH₂Br, —CH₂OH, —CH₂OCH₃, —CH₂OCH₂CH₃, —CH₂OCH₂CH₂CH₃, —CH₂OCH(CH₃)₂, —CH₂OCH(CH₂)₂, —CH₂OCH₂CF₃, —CH₂OCOCH₃, —CH₂NH₂, —CH₂NHCH₃, —CH₂N(CH₃)₂, —CH₂NHCH₂CH₃, —CH₂N(CH₃)CH₂CH₃, —CH₂NHCH₂CH₂CH₃, —CH₂NHCH(CH₃)₂, —CH₂NHCH(CH₂)₂, —CH₂N(CH₂CH₃)₂, —CH₂CH₂F, —CH₂CH₂Cl, —CH₂CH₂Br, —CH₂CH₂I, —CH₂CH₂OH, CH₂CH₂OCOCH₃, —CH₂CH₂NH₂, —CH₂CH₂N(CH₃)₂, —CH₂CH₂NHCH₃, —CH₂CH₂N(CH₃)CH₂CH₃, —CH₂CH₂NHCH₂CH₃, —CH₂CH₂NHCH(CH₃)₂, —CH₂CH₂NHCH(CH₂)₂, —CH₂CH₂N(CH₂CH₃)₂, —CH₂CH₂NHCO₂C(CH₃)₃, and —CH₂Si(CH₃)₃.

The term "unsubstituted $C_n$-alkenyl" refers to a radical, having a linear or branched, cyclic or acyclic structure, further having at least one carbon-carbon double bond, at total of n carbon atoms, all of which are nonaromatic, 3 or more hydrogen atoms, and no heteroatoms. For example, an unsubstituted $C_2$-$C_{10}$-alkenyl has 2 to 10 carbon atoms. Unsubstituted alkenyl groups include: —CH=CH₂, —CH=CHCH₃, —CH=CHCH₂CH₃, —CH=CHCH₂CH₂CH₃, —CH=CHCH(CH₃)₂, —CH=CHCH(CH₂)₂, —CH₂CH=CH₂, —CH₂CH=CHCH₃, —CH₂CH=CHCH₂CH₃, —CH₂CH=CHCH₂CH₂CH₃, —CH₂CH=CHCH(CH₃)₂, and —CH₂CH=CHCH(CH₂)₂.

The term "substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkenyl has 2 to 10 carbon atoms. The groups, —CH=CHF, —CH=CHCl and —C=CHBr, are examples of substituted alkenyl groups.

The term "unsubstituted $C_n$-alkynyl" refers to a radical, having a linear or branched, cyclic or acyclic structure, further having at least one carbon-carbon triple bond, a total of n carbon atoms, all of which are nonaromatic, at least one hydrogen atom, and no heteroatoms. For example, an unsubstituted $C_2$-$C_{10}$-alkynyl has 2 to 10 carbon atoms. The groups, —C≡H and —C≡CCH₃, are examples of unsubstituted alkynyl groups.

The term "substituted $C_n$-alkynyl" refers to a radical, having a single nonaromatic carbon atom as the point of attachment and at least one nonaromatic carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, A, Cl, Br, I, Si, P, and S. For example, a substituted $C_2$-$C_{10}$-alkynyl has 2 to 10 carbon atoms. The group, —C≡CSi(CH₃)₃, is an example of a substituted alkynyl group.

The term "unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, an unsubstituted $C_6$-$C_{10}$-aryl has 6 to 10 carbon atoms. Examples of unsubstituted aryl groups include phenyl, methylphenyl, di(methyl)phenyl, —$C_6H_4CH_2CH_3$, —$C_6H_4CH_2CH_2CH_3$, —$C_6H_4Cl_1(CH_3)_2$, —$C_6H_4CH(CH_2)_2$, —$C_6H_3(CH_3)CH_2CH_3$, —$C_6H_4CH$=$CH_2$, —$C_6H_4CH$=$CHCH_3$, —$C_6H_4C_3H$, and —$C_6H_4C_3H_3$. Aryl groups also include polycyclic fused aromatic groups such as naphthyl, quinolyl, indolyl, and the like.

The term "substituted $C_n$-aryl" refers to a radical, having a single carbon atom as point of attachment, wherein the carbon atom is part of an aromatic ring structure containing only carbon atoms, further having a total of n aromatic or non-aromatic carbon atoms, 0, 1, or more than one hydrogen atom, and at least one nonaromatic heteroatom, wherein each heteroatom is independently selected from the group consisting of N, O, F, Cl, Br, L Si, P, and S. For example, a substituted $C_6$-$C_{10}$-aryl has 6 to 10 carbon atoms. The groups, —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH$=$CH_2$, —$C_6H_4CF_3$, —$C_6H_4CN$, —$C_6H_4C$≡$CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$ are examples of substituted aryl groups.

The term "unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, an unsubstituted $C_7$-$C_{10}$-aralkyl has 7 to 10 carbon atoms. An "aralkyl" includes an alkyl substituted with an aryl group. Examples of unsubstituted aralkyls include phenylmethyl (benzyl) and phenylethyl.

The term "substituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 0, 1, or more than one hydrogen atom, and at least one heteroatom, wherein each heteroatom is independently selected from the group consisting of N, O, F, Cl, Br, I, Si, P, and S. For example, a substituted $C_7$-$C_{10}$-aralkyl has 7 to 10 carbon atoms.

The term "unsubstituted $C_n$-heteroaryl" refers to a radical, having either a single aromatic carbon atom or a single aromatic heteroatom as the point of attachment, fisher having a total of n carbon atoms, at least one hydrogen atom, and at least one heteroatom, wherein at least one of the carbon atoms and all of the heteroatoms are incorporated into one or more aromatic ring structures, further wherein each heteroatom is independently selected from the group consisting of N, O, F, Cl, Br, I, Si, P, and S. For example, an unsubstituted $C_1$-$C_{10}$-heteroaryl has 1 to 10 carbon atoms. For example, the term "heteroaryl" includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like.

The term "substituted $C_n$-heteroaryl" refers to a radical, having either a single aromatic carbon atom or a single aromatic heteroatom as the point of attachment, further having a total of n carbon atoms, at least one hydrogen atom, and at least two heteroatoms, wherein at least one of the carbon atoms and at least one of the heteroatoms are incorporated into one or more aromatic ring structures, further wherein at least one of the heteroatoms is not part of the one or more aromatic ring structures, further wherein each heteroatom is independently selected from the group consisting of N, O, F, Cl, Br, I, Si, P, and S. For example, an substituted $C_1$-$C_{10}$-heteroaryl has 1 to 10 carbon atoms.

The term "unsubstituted $C_n$-heteroaralkyl" refers to a radical, having a single saturated carbon atom as the point of attachment, further having a total of n carbon atoms, at least three hydrogen atoms, and at least one heteroatom, wherein at least one of the carbon atoms and all of the heteroatoms form an aromatic ring structure, further wherein each heteroatom is independently selected from the group consisting of N, O, F, Cl, Br, I, Si, P, and S. For example, an unsubstituted $C_2$-$C_{10}$-heteroaralkyl has 2 to 10 carbon atoms.

The term "substituted $C_n$-heteroaralkyl" refers to a radical having a single saturated carbon atom as the point of attachment, further having a total of n carbon atoms, 0, 1, or more than one hydrogen atom, and at least two heteroatoms, wherein at least one of the carbon atoms and at least one of the heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkyl has 2 to 10 carbon atoms.

The term "unsubstituted $C_n$-acyl" refers to a radical, having a single carbon atom of a carbonyl group as the point of attachment, further having a linear or branched, cyclic or acyclic structure, further having a total of n carbon atoms, I or more hydrogen atoms, a total of one oxygen atom, and no additional heteroatoms. For example, an unsubstituted $C_1$-$C_{10}$-acyl has 1 to 10 carbon atoms. The groups, —COH, —$COCH_3$, —($COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are examples of unsubstituted acyl groups.

The term "substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-acyl has 1 to 10 carbon atoms. The term substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples substituted acyl groups.

The term "unsubstituted $C_n$-alkoxy" refers to a group, having the structure —OR, in which R is an unsubstituted $C_n$- alkyl, as that term is defined above. Unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$.

The term "substituted C$_n$-alkoxy" refers to a group, having the structure —OR, in which R is a substituted C$_n$-alkyl, as that term is defined above. For example, —OCH$_2$CF$_3$ is a substituted alkoxy group.

The term "unsubstituted C$_n$-alkenyloxy" refers to a group, having the structure —OR, in which R is an unsubstituted C$_n$-alkenyl, as that term is defined above.

The term "substituted C$_n$-alkenyloxy" refers to a group, having the structure —OR, in which R is a substituted C$_n$-alkenyl, as that term is defined above.

The term "unsubstituted C$_n$-alkynyloxy" refers to a group, having the structure —OR, in which R is an unsubstituted C$_n$-alkynyl, as that term is defined above.

The term "substituted C$_n$-alkenyloxy" refers to a group, having the structure —OR, in which R is a substituted C$_n$-alkynyl, as that term is defined above.

The term "unsubstituted C$_n$-aryloxy" refers to a group, having the structure —OAr, in which Ar is an unsubstituted C$_n$-aryl, as that term is defined above. An example of an unsubstituted aryloxy group is —OC$_6$H$_5$.

The term "substituted C$_n$-aryloxy" refers to a group, having the structure —OAr, in which Ar is a substituted C$_n$-aryl, as that term is defined above.

The term "unsubstituted C$_n$-aralkyloxy" refers to a group, having the structure —OAr, in which Ar is an unsubstituted C$_n$-aralkyl, as that term is defined above.

The term "substituted C$_n$-aralkyloxy" refers to a group, having the structure —OAr, in which Ar is a substituted C$_n$-aralkyl, as that term is defined above.

The term "unsubstituted C$_n$-heteroaryloxy" refers to a group, having the structure —OAr, in which Ar is an unsubstituted C$_n$-heteroaryl, as that term is defined above.

The term "substituted C$_n$-heteroaryloxy" refers to a group, having the structure —OAr, in which Ar is a substituted C$_n$-heteroaryl, as that term is defined above.

The term "unsubstituted C$_n$-heteroaralkyloxy" refers to a group, having the structure —OAr, in which Ar is an unsubstituted C$_n$-heteroaralkyl, as that term is defined above.

The term "substituted C$_n$-heteroaralkyloxy" refers to a group, having the structure —OAr, in which Ar is a substituted C$_n$-heteroaralkyl, as that term is defined above.

The term "unsubstituted C$_n$-acyloxy" refers to a group, having the structure —OAc, in which Ac is an unsubstituted C$_n$-acyl, as that term is defined above. An unsubstituted acyloxy group includes alkylcarbonyloxy and arylcarbonyloxy groups. For example, —OCOCH$_3$ is an example of an unsubstituted acyloxy group.

The term "substituted C$_n$-acyloxy" refers to a group, having the structure —OAc, in which Ac is a substituted C$_n$-acyl, as that term is defined above. A substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "unsubstituted C$_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, an unsubstituted C$_1$-C$_{10}$-alkylamino has 1 to 10 carbon atoms. An alkylamino group includes dialkylamino groups. An unsubstituted alkylamino group would include —NHCH$_3$, —NHCH$_2$CH$_3$, —NHCH$_2$CH$_2$CH$_3$, —NHCH (CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC (CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "substituted C$_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a; total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted C$_1$-C$_{10}$-alkylamino has 1 to 10 carbon atoms.

The term "unsubstituted C$_n$-alkenylamino" refers to a radical, having a single nitrogen atom as the point of attachment, further having a linear or branched, cyclic or acyclic structure, containing at least one carbon-carbon double bond, a total of n carbon atoms, all of which are nonaromatic, 4 or more hydrogen atoms, a total of one nitrogen atom, and no additional heteroatoms. For example, an unsubstituted C$_2$-C$_{10}$-alkenylamino has 2 to 10 carbon atoms. An alkenylamino group includes dialkenylamino and alkyl(alkenyl) amino groups.

The term "substituted C$_n$-alkenylamino" refers to a radical, having a single nitrogen atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted C$_2$-C$_{10}$-alkenylamino has 2 to 10 carbon atoms.

The term "unsubstituted C$_n$-alkynylamino" refers to a radical, having a single nitrogen atom as the point of attachment, further having a linear or branched, cyclic or acyclic structure, containing at least one carbon-carbon triple bond, a total of n carbon atoms, all of which are nonaromatic, at least one hydrogen atoms, a total of one nitrogen atom, and no additional heteroatoms. For example, an unsubstituted C$_2$-C$_{10}$-alkynylamino has 2 to 10 carbon atoms. An alkynylamino group includes dialkynylamino and alkyl(alkynyl)amino groups.

The term "substituted C$_n$-alkynylamino" refers to a radical, having a single nitrogen atom as the point of attachment, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted C$_2$-C$_{10}$-alkynylamino has 2 to 10 carbon atoms.

The term "unsubstituted C$_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, an unsubstituted $C_6$-$C_{10}$-arylamino has 6 to 10 carbon atoms. An arylamino group includes diarylamino and alkyl(aryl)amino groups.

The term "substituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 0, 1, or more hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_6$-$C_{10}$-arylamino has 6 to 10 carbon atoms.

The term "unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, an unsubstituted $C_7$-$C_{10}$-aralkylamino has 7 to 10 carbon atoms. An aralkylamino group includes diaralkylamino, alkyl(aralkyl)amino, and aryl (aralkyl)amino groups.

The term "substituted $C_n$-aralkylamino" refers to a radical, having a single nitrogen atom as the point of attachment, further having at least one or two saturated carbon atoms attached to the nitrogen atom, further having a total of n carbon atoms, wherein at least 6 of the carbon atoms form an aromatic ring structure containing only carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_7$-$C_{10}$-aralkylamino has 7 to 10 carbon atoms.

The term "unsubstituted $C_n$-heteroaryiamino" refers to a radical, having a single nitrogen atom as the point of attachment, further having a total of n carbon atoms, at least one hydrogen atom, and at least one additional heteroatom, in addition to the nitrogen atom at the point of attachment, wherein at least one of the carbon atoms and all of the additional heteroatoms are incorporated into one or more aromatic ring structures, further wherein each additional heteroatom is independently selected from the group consisting of N, O, F, Cl, Br, I, Si, P, and S For example, an unsubstituted $C_1$-$C_{10}$-heteroarylamino has 1 to 10 carbon atoms. A heteroarylamino group includes alkyl(heteroaryl)amino and aryl (heteroaryl)amino groups.

The term "substituted $C_n$-heteroarylamino" refers to a radical, having a single nitrogen atom as the point of attachment, further having a total of n carbon atoms, at least one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the additional heteroatoms is not part of the one or more aromatic ring structures, further wherein each additional heteroatom is independently selected from the group consisting of N, O, F, Cl, Br, I, Si, P, and S. For example, an substituted $C_1$-$C_{10}$-heteroarylamino has 1 to 10 carbon atoms.

The term "unsubstituted $C_n$-heteroaralkylamino" refers to a radical, having a single nitrogen atom as the point of attachment, further having one or two saturated carbon atoms attached to the nitrogen atom, further having a total of n carbon atoms, at least three hydrogen atoms, at least one additional heteroatom, wherein at least one of the carbon atoms and all of the additional heteroatoms form an aromatic ring structure, further wherein each additional heteroatom is independently selected from the group consisting of N, O, F, Cl, Br, I, Si, P, and S. For example, an unsubstituted $C_2$-$C_{10}$-heteroaralkylamino has 2 to 10 carbon atoms. A heteroaralkylamino group includes alkyl(heteroaralkyl)amino and aryl (heteroaralkyl)amino groups.

The term "substituted $C_n$-heteroaralkylamino" refers to a radical, having a single nitrogen atom as the point of attachment, further having one or two saturated carbon atoms attached to the nitrogen atom, further having a total of n carbon atoms, 0, 1, or more than one hydrogen atoms, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkylamino has 2 to 10 carbon atoms.

The term "unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, an unsubstituted $C_1$-$C_{10}$-amido has 1 to 10 carbon atoms. A amido group includes N-alkyl-amido, N-aryl-amido, N-aralkyl-amido, acylamino, alkylcarbonylamino, arylcarbonylamino, and ureido groups. The group, —NHCOCH$_3$, is an example of an unsubstituted amido group.

The term "substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or non-aromatic carbon atoms, 0, 1, or more than one hydrogen atoms, at least one additional heteroatom in addition to the oxygen of the carbonyl group, wherein each additional heteroatom is independently selected from the group consisting of N, O, F, Cl, Br, L Si, P, and S. For example, a substituted $C_1$-$C_{10}$-amido has 1 to 10 carbon atoms. The group, —NHCO$_2$C(CH$_3$)$_3$, is an example of an substituted amido group.

The term "unsubstituted $C_n$-alkylthio" refers to a group, having the structure —SR, in which R is an unsubstituted $C_n$-alkyl, as that term is defined above. The group, —SCH$_3$, is an example of an unsubstituted alkylthio group.

The term "substituted $C_n$-alkylthio" refers to a group, having the structure —SR, in which R is a substituted $C_1$ alkyl, as that term is defined above.

The term "unsubstituted $C_n$-alkenylthio" refers to a group, having the structure —SR, in which R is an unsubstituted $C_n$-alkenyl, as that term is defined above.

The term "substituted $C_n$-alkenylthio" refers to a group, having the structure —SR, in which R is a substituted $C_n$-alkenyl, as that term is defined above.

The term "unsubstituted $C_n$-alkynylthio" refers to a group, having the structure —SR, in which R is an unsubstituted $C_n$-alkynyl, as that term is defined above.

The term "substituted $C_n$-alkenylthio" refers to a group, having the structure —SR, in which R is a substituted $C_n$-alkynyl, as that term is defined above.

The term "unsubstituted $C_n$-arylthio" refers to a group, having the structure —SAr, in which Ar is an unsubstituted $C_n$-aryl, as that term is defined above. The group, —SC$_6$H$_5$, is an example of an unsubstituted arylthio group.

The term "substituted C-arylthio" refers to a group, having the structure —SAr, in which Ar is a substituted $C_n$-aryl, as that term is defined above.

The term "unsubstituted $C_n$-aralkylthio" refers to a group, having the structure —SAr, in which Ar is an unsubstituted $C_n$-aralkyl, as that term is defined above. The group, —SCH$_2$C$_6$H$_5$, is an example of an unsubstituted aralkyl group.

The term "substituted $C_n$-aralkylthio" refers to a group, having the structure —SAr, in which Ar is a substituted $C_n$-aralkyl, as that term is defined above.

The term "unsubstituted $C_n$-heteroarylthio" refers to a group, having the structure —SAr, in which Ar is an unsubstituted $C_n$-heteroaryl, as that term is defined above.

The term "substituted $C_n$-heteroarylthio" refers to a group, having the structure —SAr, in which Ar is a substituted $C_n$-heteroaryl, as that term is defined above.

The term "unsubstituted $C_n$-heteroaralkylthio" refers to a group, having the structure —SAr, in which Ar is an unsubstituted $C_n$-heteroaralkyl, as that term is defined above.

The term "substituted $C_n$-heteroaralkylthio" refers to a group, having the structure —SAr, in which Ar is a substituted $C_n$-heteroaralkyl, as that term is defined above.

The term "unsubstituted $C_n$-acylthio" refers to a group, having the structure —SAc, in which Ac is an unsubstituted $C_n$-acyl, as that term is defined above. The group, —SCOCH$_3$, is an example of an unsubstituted acylthio group.

The term "substituted $C_n$-acylthio" refers to a group, having the structure —SAc, in which Ac is a substituted $C_n$-acyl, as that term is defined above.

The term "unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, an unsubstituted $C_1$-$C_{10}$-alkylsilyl has 1 to 10 carbon atoms. An alkylsilyl group includes dialkylamino groups. The groups, —Si(CH$_3$)$_3$ and —Si(CH$_3$)$_2$C(CH$_3$)$_3$, are examples of unsubstituted alkylsilyl groups.

The term "substituted $C_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a substituted $C_1$-$C_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolanine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

III. Administration and Formulation of Therapeutic Compounds

In additional embodiments, the present invention concerns formulation of Oncrasin compound compositions in pharmaceutically-acceptable solutions for administration to a cell, tissue, animal, or patient either alone, or in combination with one or more second agent or second therapy.

Aqueous pharmaceutical compositions of the present invention will have an effective amount of a compound that modulates a target protein of interest and/or its related biological functions or activities. Such compositions generally will be dissolved or dispersed in a pharmaceutically acceptable solvent, carrier, or aqueous medium. An "effective amount," for the purposes of therapy, is defined at that amount that causes a clinically measurable difference in the condition of the subject. This amount will vary depending on the condition, the substance, the condition of the patient, the type of treatment, etc.

The phrases "pharmaceutically" or "pharmacologically acceptable" refer to molecular entities and compositions that do not produce a significant adverse, allergic, or other untoward reaction when administered to an animal, or human. As used herein, "pharmaceutically acceptable carrier" includes any and all solvents, dispersion media, coatings, antibacterial and antifungal agents, isotonic, absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as other therapeutic agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, inhalants and the like.

The active compounds of the present invention can be formulated for parenteral administration, e.g., formulated for injection via the intravenous, intramuscular, subcutaneous, or even intraperitoneal routes. The preparation of a composition that contains a Oncrasin compound alone or in combination with a second therapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injection include sterile aqueous solutions or dispersions; formulations including lipids, sesame oil, peanut oil, or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like. Salts formed can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, DMSO, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous or lipid solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 1035-1038 and 1570-1580). Some variation in dosage will necessarily occur depending on the condition of the subject being treated. The person responsible for administration will, in any event, determine the appropriate dose for the individual subject.

In certain aspects of the invention, the route of administering a therapeutic composition may be by parenteral administration. The parenteral administration may be intravenous injection, subcutaneous injection, intramuscular or intratumoral injection, ingestion, or a combination thereof. In certain aspects, the composition comprising an Oncrasin compound is administered from about 0.01, 0.05, 0.1, 0.2, 0.3, 0.4, 0.5, 1.0, 2, 3, 4, 5, 6, 7, 8, 9, to about 10, 20, 30, 40, 50, 60, 70, 80, 90, or 100 nanogram or microgram/kg/body weight per dose, including integers and ranges derivable there between. In certain aspects, the composition comprising an Oncrasin compound is administered from about 1 to about 5 nanogram or microgram/kg/body weight per dose. In certain aspects, the composition comprising a Oncrasin compound is administered from about 1.2 to about 2.4 nanogram or microgram/kg/body weight per dose. In certain aspects, the amount of Oncrasin compound administered per dose may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9. about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9 to about 10.0 or more nanogram/kg/body, microgram/kg/body or milligram/kg/body.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

A. Alimentary Delivery

The term "alimentary delivery" refers to the administration, directly or otherwise, to a portion of the alimentary canal of a subject or patient. The term "alimentary canal" refers to the tubular passage that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastrointestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

1. Oral Delivery

In certain applications, the pharmaceutical compositions disclosed herein may be delivered via oral administration to an animal or human. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

2. Endoscopic Administration

Endoscopy can be used for therapeutic delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., 1992). However, the procedure is unpleasant for the patient, and requires a highly skilled staff.

3. Rectal Administration

Therapeutics administered by the oral route can often be alternatively administered by the lower enteral route, i.e., through the anal portal into the rectum or lower intestine. Rectal suppositories, retention enemas or rectal catheters can be used for this purpose and may be preferred when patient compliance might a otherwise be difficult to achieve (e.g., in pediatric and geriatric applications, or when the patient is vomiting or unconscious). Rectal administration may result in more prompt and higher blood levels than the oral route, but the converse may be true as well (Remington's Pharmaceutical Sciences, 711, 1990). Because about 50% of the therapeutic that is absorbed from the rectum will bypass the liver, administration by this route significantly reduces the potential for first-pass metabolism (Benet et al., 1996).

B. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399, 363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that it is easy to use a syringe.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration (see for example, Remington's Pharmaceutical Sciences, 1035-1038 and 1570-1580. Some variation in dosage will necessarily occur depending on the condition of the subject being treated. The person responsible for administration will, in any event, determine the appropriate dose for the individual subject.

Moreover, for human administration, preparations should meet sterility, pyrogenicity, and the general safety and purity standards as required by governmental regulations and standards.

The term "parenteral delivery" refers to the administration of a therapeutic of the invention to an animal in a manner other than through the digestive canal. Means of preparing and administering parenteral pharmaceutical compositions are known in the art (see, e.g., Remington's Pharmaceutical Sciences, pages 1545-1569, 1990).

C. Intraluminal Administration

Intraluminal administration, for the direct delivery of a therapeutic to an isolated portion of a tubular organ or tissue (e.g., such as an artery, vein, ureter or urethra), may be desired for the treatment of patients with diseases or conditions afflicting the lumen of such organs or tissues. To effect this mode of administration, a catheter or cannula is surgically introduced by appropriate means. After isolation of a portion of the tubular organ or tissue for which treatment is sought, a composition comprising a therapeutic of the invention is infused through the cannula or catheter into the isolated segment. After incubation for from about 1 to about 120 minutes, during which the therapeutic is taken up or in contact with the cells of the interior lumen of the vessel, the infusion cannula or catheter is removed and flow within the tubular organ or tissue is restored by removal of the ligatures which effected the isolation of a segment thereof (Morishita et al., 1993). Therapeutic compositions of the invention may also be combined with a biocompatible matrix, such as a hydrogel material, and applied directly to vascular tissue in vivo.

D. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

E. Epidermal and Transdermal Delivery

Epidermal and transdermal delivery, in which pharmaceutical compositions containing therapeutics are applied topically, can be used to administer drugs to be absorbed by the local dermis or for further penetration and absorption by underlying tissues, respectively. Means of preparing and administering medications topically are known in the art (see, e.g., Remington's Pharmaceutical Sciences, 1596-1609, 1990).

F. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells or to subjects in need of treatment. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the Oncrasin compounds disclosed herein. The formation and use of liposomes is generally known to those of skill in the art (see below and see for example, Couvreur et al., 1977; Couvreur, 1988; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Chonn, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567, 434; 5,552,157; 5,565,213; 5,738,868 and 5,795,587, each specifically incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

The fate and disposition of intravenously injected liposomes depend on their physical properties, such as size, fluidity, and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Alternatively, the invention provides for pharmaceutically-acceptable nanocapsule formulations of the compositions of the present invention. Nanocapsules can generally entrap compounds in a stable and reproducible way (Henry-Michelland et al., 1987; Quintanar-Guerrero et al., 1998). Biodegradable polyalkyl-cyanoacrylate nanoparticles that meet these requirements are contemplated for use in the present invention. Such particles may be are easily made, as described (Couvreur et al., 1980; 1988; zur Muhien et al., 1998; Zambaux et al., 1998; Pinto-Alphandary et al., 1995 and U.S. Pat. No. 5,145,684, specifically incorporated herein by reference in its entirety).

G. Lipid Formulations

The present invention includes liposomal drug formulations' comprising a Oncrasin compound or optimized drug, and any type of lipid composition or liposome known in the art, including those exemplified below. As used herein, a liposome is a structure having lipid-containing membranes enclosing an aqueous interior. Liposomes may have one or more lipid membranes. The invention includes both single-layered liposomes, which are referred to as unilamellar, and multi-layer liposomes, which are referred to as multilamellar. In further aspects, lipid compositions need not contain significant levels of structure as long as the deliver of the Oncrasin compound is facilitated.

1. Liposome/Lipid Composition

Lipid compositions of the invention may include any of a wide variety of different lipids, including, e.g., amphipathic, neutral, cationic, and anionic lipids. Such lipids can be used alone or in combination, and can also include additional components, such as cholesterol, bilayer stabilizing components, e.g., polyamide oligomers (see, U.S. Pat. No. 6,320, 017), peptides, proteins, detergents, and lipid-derivatives, such as PEG coupled to phosphatidylethanolamine and PEG conjugated to ceramides (see U.S. Pat. No. 5,885,613).

In numerous embodiments, amphipathic lipids are included in liposomes of the present invention. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidyicholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and t3-acyloxyacids, can also be used. Additionally, such amphipathic lipids can be readily mixed with other lipids, such as triglycerides and sterols.

Any of a number of neutral lipids can be included, referring to any of a number of lipid species which exist either in an uncharged or neutral zwitterionic form at physiological pH, including, e.g., diacyiphosphatidylcholine, diacylphosphatidylethanolamine, ceramide, sphingomyelin, cephalin, cholesterol, cerebrosides, diacylglycerols, and sterols.

Cationic lipids, which carry a net positive charge at physiological pH, can readily be incorporated into liposomes for use in the present invention. Such lipids include, but are not limited to, N,N-dioleyl-N,N-dimethylammonium chloride ("DODAC"); N-(2,3-d-ioleyloxy)propyl-N, N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 313-(N—(N',N'-dimethylaminoethane)-carbamoyl) cholesterol ("DC-Chol"), N-(1-(2,3-dioleyloxy)propyl)-N2-(sperminecarboxamido)ethyl)-N,N-dimethylammonium trifluoracetate ("DOSPA"), d-ioctadecylamidoglycyl carboxyspermine ("DOGS"), 1,2-dileoyl-sn-3-phosphoethanolamine ("DOPE"), 1,2-dioleoyl-3-dimethylammonium propane (t1DODAP"), and N-(1,2-dimyristyloxyprop-3-yl)-N,N-dimethyl-N-hydroxyethyl ammonium bromide ("DM-RIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL).

Anionic lipids suitable for use in the present invention include, but are not limited to, phosphatidylglycerol, cardiolipin, diacylphosphatidylserine, diacyiphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In one embodiment, cloaking agents, which reduce elimination of liposomes by the host immune system, can also be included in liposomes of the present invention, such as polyamide-oligomer conjugates, and PEG-lipid conjugates (see, U.S. Pat. Nos. 5,820,873, 5,534,499 and 5,885,613).

Also suitable for inclusion in the present invention are programmable fusion lipid formulations. Such formulations have little tendency to fuse with cell membranes and deliver their payload until a given signal event occurs. This allows the lipid formulation to distribute more evenly after injection into an organism or disease site before it starts fusing with cells. The signal event can be, for example, a change in pH, temperature, ionic environment, or time. In the latter case, a fusion delaying or "cloaking" component, such as a PEG-lipid conjugate, can simply exchange out of the liposome membrane over time. By the time the formulation is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, liposomes of the present invention comprises sphingomyelin (SM). As used herein, the general term sphingomyelin (SM) includes SMs having any long chain base or fatty acid chain. Naturally occurring SMs have the phosphocholine head group linked to the hydroxyl group on carbon one of a long-chain base and have a long saturated acyl chain linked to the amide group on carbon 2 of the long-chain base (reviewed in Barenholz (1984)). In cultured cells, about 90 to 95% of the SMs contain sphingosine (1,3-dihydroxy-2-amino-4-octadecene), which contains a trans-double bond between C4 and C5, as the long-chain base, whereas most of the remainder have sphinganine (1,3-dihydroxy-2-amino-4-octadecane) as the base and lack the trans double bond between carbons 4 and 5 of the long chain base. The latter SMs are called dihydrosphingomyelins (DHSM). DHSM may contain one or more cis double bonds in the fatty acid chain. In one embodiment, DHSM contains both a fully saturated fatty acid chain and a saturated long base chain. Liposomes comprising SM or, specifically, DHSM, are described in further detail in U.S. Provisional Patent Application No. 60/571,712.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof. A variety of different targeting agents and methods are described in the art, e.g., in Sapra and Allen (2003); and Abra et al. (2002).

The use of liposomes with a surface coating of hydrophilic polymer chains, such as polyethylene glycol (PEG) chains, for targeting has been proposed (Allen, et al., 1995; Blume, et al., 1993; Klibanov, et al., 1992; Woodle, 1991; Zalipsky, 1993; Zalipsky, 1994; Zalipsky, 1995). In one approach, a ligand, such as an antibody, for targeting the liposomes is linked to the polar head group of lipids forming the liposome. In another approach, the targeting ligand is attached to the distal ends of the PEG chains forming the hydrophilic polymer coating (Klibanov et al., 1992).

Standard methods for coupling the target agents can be used. For example, phosphatidylethanolarine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., J. Bio. Chem., 265:16337-16342 (1990) and Leonetti, et al., Proc. Natl. Acad. Sci. USA), 87:2448-2451 (1990). Other examples of antibody conjugation are disclosed in U.S. Pat. No. 6,027,726. Examples of targeting moieties also include other proteins, specific to cellular components, including antigens associated with neoplasms or tumors. Proteins used as targeting moieties can be attached to the liposomes via covalent bonds (see, Heath, Covalent Attachment of Proteins to Liposomes, 149 Methods in Enzymology 111-119 (Academic Press, Inc. 1987)). Other targeting methods include the biotin-avidin system.

2. Methods of Preparation

A variety of methods for preparing liposomes are known in the art, including e.g. those described in Szoka, et al., (1980); U.S. Pat. Nos. 4,186,183, 4,217,344, 4,235,871, 4,261,975, 4,485,054, 4,501,728, 4,837,028, 4,946,787; PCT Publication No. WO 91/1 7424; Deamer and Bangham (1976); Fraley, et al., (1979); Hope, et al. (1985); Mayer et al. (1986); Williams et al. (1988); Ostro (1983); Hope et al. (1986); and Torchilin et al. (2003), and references cited therein. Suitable methods include, but are not limited to, sonication, extrusion, high pressure/homogenization, microfluidization, detergent dialysis, calcium-induced fusion of small liposome vesicles, and ether-infusion methods, all of which are well known in the art.

Alternative methods of preparing liposomes are also available. For instance, a method involving detergent dialysis based self-assembly of lipid particles is disclosed and claimed in U.S. Pat. No. 5,976,567. Further methods of preparing liposomes using continuous flow hydration are under development and can often provide the most effective large scale manufacturing process.

Unilamellar vesicles can be prepared by sonication or extrusion Sonication is generally performed with a tip sonifier, such as a Branson tip sonifier, in an ice bath. Typically, the suspension is subjected to severed sonication cycles.

Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes that have not been sized during formation may be sized to achieve a desired size range and relatively narrow distribution of liposome sizes. A size range of about 0.2-0.4 microns allows the liposome suspension to be sterilized by filtration through a conventional filter.

The filter sterilization method can be carried out on a high throughput basis if the liposomes have been sized down to about 0.2-0.4 microns.

Several techniques are available for sizing liposomes to a desired size. General methods for sizing liposomes include, e.g., sonication, by bath or by probe, or homogenization, including the method described in U.S. Pat. No. 4,737,323. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield (1981), incorporated herein by reference. Liposomes of any size may be used according to the present invention. In certain embodiments, liposomes of the present invention have a size ranging from about 0.05 microns to about 0.45 microns, between about 0.05 and about 0.2 microns, or between 0.08 and 0.12 microns in diameter. In other embodiments, liposomes of the present invention are between about 0.45 microns to about 3.0 microns, about 1.0 to about 2.5 microns, about 1.5 to about 2.5 microns and about 2.0 microns.

IV. Combination Therapy

In the context of the present invention, it is contemplated that Oncrasin therapies may be used in combination with an additional therapeutic agent(s) to more effectively treat a cancer or viral infection. Additional therapeutic agents contemplated for use in combination with Oncrasin therapies include traditional anticancer therapies. Such anticancer therapies include but are not limited to, radiotherapy, chemotherapy, gene therapy, hormonal therapy or immunotherapy that targets cancer/tumor cells, and are discussed in greater detail below.

To kill cells, induce cell-cycle arrest, inhibit migration, inhibit metastasis, inhibit survival, inhibit proliferation, or otherwise reverse or reduce the malignant phenotype of cancer cells, using the methods and compositions of the present invention, one would generally contact a cell with an Oncrasin therapy in combination with an additional therapy. The compositions/therapies would be provided in a combined amount effective to inhibit a cancer or viral infection. This process may involve contacting the cancer cell(s) or tumor with an Oncrasin therapy in combination with an additional therapeutic agent or method at the same time. This may be achieved by contacting the cell(s)/tumor with a single composition or method, or by contacting the cell with two distinct compositions or methods at the same time, wherein one includes the Oncrasin therapy and the other includes the additional agent.

Alternatively, treatment with an Oncrasin therapy may precede or follow the additional treatment by intervals ranging from minutes to weeks. In embodiments where the additional therapy is applied separately to the cell, one would generally ensure that a significant period of time did not expire between the time of each delivery or treatment, such that the therapies/agents would still be able to exert an advantageously combined effect on the cell(s)/tumor. In such instances, it is contemplated that one would contact the cell(s)/tumor with both modalities within about 12-24 hr of each other and, more preferably, within about 6-12 hr of each other, with a delay time of only about 12 hr being most preferred. Thus, therapeutic levels of the drugs will be maintained. In some situations, it may be desirable to extend the time period for treatment significantly (for example, to reduce toxicity). Thus, several days (2, 3, 4, 5, 6 or 7) to several weeks (1, 2, 3, 4, 5, 6, 7 or 8) may lapse between the respective administrations.

It also is conceivable that more than one administration of an Oncrasin therapy in combination with an additional anticancer agent will be desired. Various combinations may be employed, where an Oncrasin therapy is "A" and the additional therapeutic agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve a therapeutic effect, both agents/treatments are delivered to a cell in a combined amount effective to achieve the desired effect.

V. Therapeutic Targets

A. Cancer

Embodiments of the invention can be used to target a variety of disease or pathological conditions, such as cancer or viral infection. Cancers that may be evaluated by methods and compositions of the invention include cancer cells that include cells and cancer cells from the bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgk's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; mycloid sarcoma; and hairy cell leukemia. Moreover, RNA can be evaluated in pre-cancers, such as metaplasia, dysplasia, and hyperplasia.

B. Viral Infection

Viral infections are a principal cause of illness due to communicable diseases that affect the public at large. Of these, influenza viruses, including types A and B, are a significant factor responsible for causing respiratory symptoms as well as systemic malaise; other respiratory viruses include parainfluenza 1, 2, 3, and 4, respiratory syncytial virus, and adenovirus. The influenza viruses undergo rapid mutation of strains, producing pathogens with varying degrees of virulence and severity of symptoms.

The compounds of the invention and related methods may also be used to treat other viral infection. Formulations containing Oncrasins can be administered to inhibit viral replication. The viral infection can be due to a RNA virus or a DNA virus. Examples of specific viral diseases which may be treated by administered Oncrasins include, but are not limited to, hepatitis A, hepatitis B, hepatitis C, non-A, non-B, non-C hepatitis, Epstein-Barr viral infection, HIV infection, herpes virus (EB, CML, herpes simplex), papilloma, poxvirus, picorna virus, adeno virus, rhino virus, HTLV I, HTLV II, and human rotavirus. The patient may be co-treated with a second antiviral agent.

VI. Screening For Ras Targeting Compounds

Compounds can be screened for that can specifically kill tumor cells but not their normal counterparts, for instance T29, T29Kt1, and T29Ht1 cells. Cells can be treated in parallel with compounds in a diverse chemical library. For example, T29 cells are normal human ovarian surface epithelial cells immortalized with the catalytic subunit of human telomerase reverse transcriptase and the SV40 early genomic region. (Liu et al., 2004). T29Ht1 and T29Kt1 cells were derived from tumors that were established from T29 cells stably transfected with oncogenic H-Ras and K-Ras, respectively, (Liu et al., 2004) and are highly tumorigenic. Cells are seeded and subsequently treated with test compound. Lethal effect are determined by using assays that detect cell cycle status, cell death, or inhibition of cell growth. Compounds found to kill >50% of the target cells but not non-target cells are subjected to additional analysis to confirm the finding. Further analysis of the compounds selected include dose responses of these cells to the compounds and the antitumor effect of the compounds.

VII. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Identification and Characterization of Oncrasins Family of Compounds

Library screening for oncogenic Ras-targeted compounds To screen for compounds that can specifically kill tumor cells but not their normal counterparts, T29, T29Kt1, and T29Ht1 cells were treated in parallel with compounds in a diverse chemical library obtained from Chembridge Corporation. T29 cells are normal human ovarian surface epithelial cells immortalized with the catalytic subunit of human telomerase reverse transcriptase and the SV40 early genomic region. (Liu et al., 2004) T29Ht1 and T29Kt1 cells were derived from tumors that were established from T29 cells stably transfected with oncogenic H-Ras and K-Ras, respectively, (Liu et al., 2004) and were highly tumorigenic. Cells seeded in a 96-well plate were treated with each compound at a final concentration of about 5 μg/mL (about 20-30 μM). Cells treated with solvent (dimethyl sulfoxide, DMSO) were used as controls. A lethal effect was determined in a sulforhodamine B (SRB) assay 4 days after treatment. (Rubinstein et al., 1990) Compounds found to kill >50% of T29Kt1 or T29Ht1 cells but not T29 cells were then subjected to 2 additional tests to confirm the SRB assay finding. In screening 10,000 compounds, six compounds were identified that induced cytotoxic effects in either T29Kt1 or T29Ht1 cells but not in the parental T29 cells.

Figure 1B:
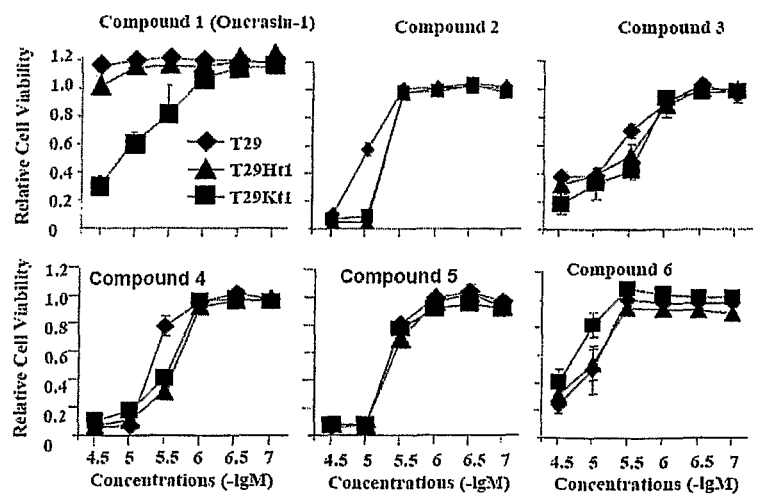

To further study the effect of the compounds that selectively killed T29Kt1 or T29Ht1 cells, the dose responses of these cells to the six compounds were determined (FIG. 1A). Compound 4 was identified previously to induce tumor-selective cytotoxicity (Wu et al., 2003; Zhu et al., 2004). Nevertheless, a dose-response study showed that only Oncrasin-1 was highly selective for T29Kt1 cells at a wide range of doses; the others showed either a limited selectivity or narrow selective dose windows (FIG. 1B). The inventors focused on analyzing the antitumor effect of this compound. Oncrasin-1 induced a dose-dependent cytotoxicity in T29Kt1 cells with an $IC_{50}$ of 2.5 μM. In contrast, there was no detectable cytotoxicity in T29 or T29Ht1 cells up to 100 μM, the highest concentration tested. A time course assay showed that Oncrasin-1 induced time-dependent toxicity in T29Kt1 cells but not in T29 or T29Ht1 cells (FIG. 1C).

Antitumor activity of Oncrasin in human cancer cells To study the effects of Oncorasin-1 on native human cancer cells, cell viability of eight human lung cancer cells were evaluated after treatment with various doses of Oncrasin-1. The result showed that Oncrasin-1 can effectively kill K-Ras mutant H460 cells ($IC_{50}$=0.25 μM), H2122 ($IC_{50}$=0.79), and A549 cells ($IC_{50}$=1.58 μM) (FIG. 2). These three cell lines contain Q61H, G12C, and G12S mutation in the K-Ras gene, respectively. Oncrasin-1 also effectively kills H226B cells ($IC_{50}$=1.2 μM) whose status in the Ras genes is not known. However, Oncrasin-1 has minimal effect to H322 and H1395 cell that have wild-type Ras genes, and has minimal effect to H1299 and H2087 cells that harbor mutant N-Ras genes. This result suggests that Oncrasin-1 is not only effective to ovarian cancer cells with mutant K-Ras gene, but also effective to lung cancer cells with mutant K-Ras gene. It was also found that several pancreatic cancer cell lines and colon cancer cell lines with mutant K-Ras gene were susceptible to Oncrasin-1 treatment. For example, the $IC_{50}$ of Oncrasin-1 in pancreatic cancer cells AsPC-1 (K-Ras G12D mutation) and Capanc-1 (K-Ras G12V mutation) were 0.04 and 0.42 μM, respectively. The $IC_{50}$ for a colon cancer cell line HCT116 (harboring a G13D mutation in K-Ras) is 3.1 μM. Those results suggested that Oncrasin is effective against a variety of lung; colon and pancreatic cancer cells with K-Ras mutations.

Figure 3A:
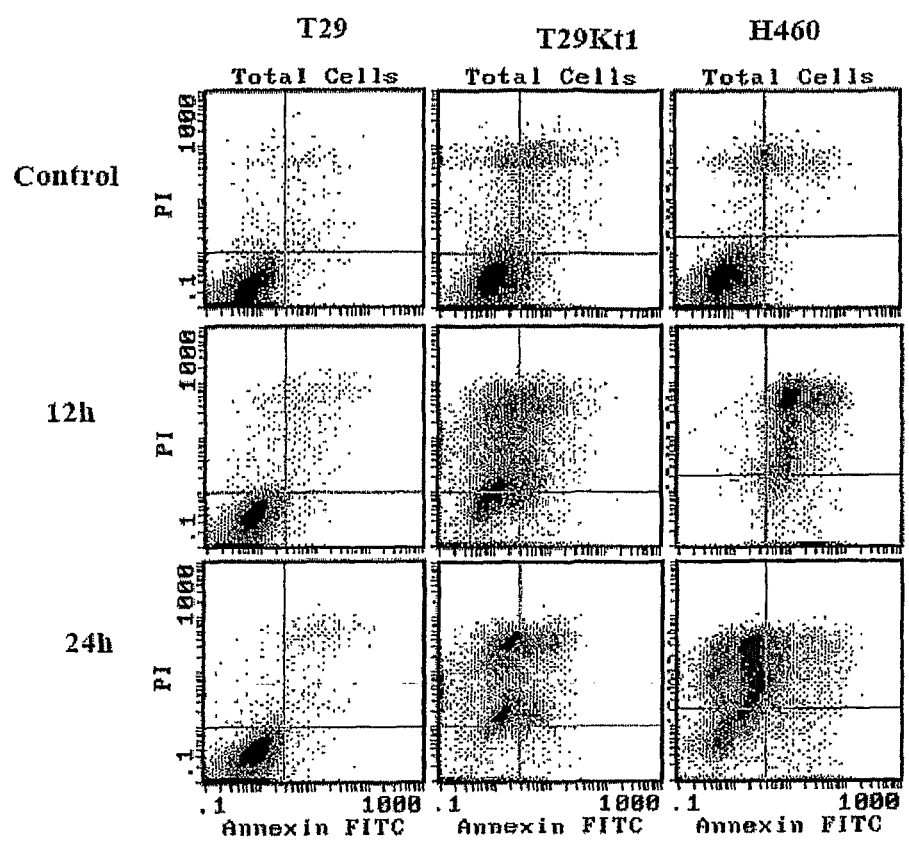
FIGS. 3A and 3B (FIG. 3A) Apoptosis induction by Oncrasin-1. T29, T29Kt1, and H460 cells were treated with Oncrasin-1 at 30 μM (for T29 or T29Kt1) or 3 μM (for H460) and then harvested 12 or 24 h later. Cell death was detected by PI and annexin V staining. From 70% to 90% of H460 and T29Kt1 cells stained with annexin V, PI, or both.
Figure 3B:
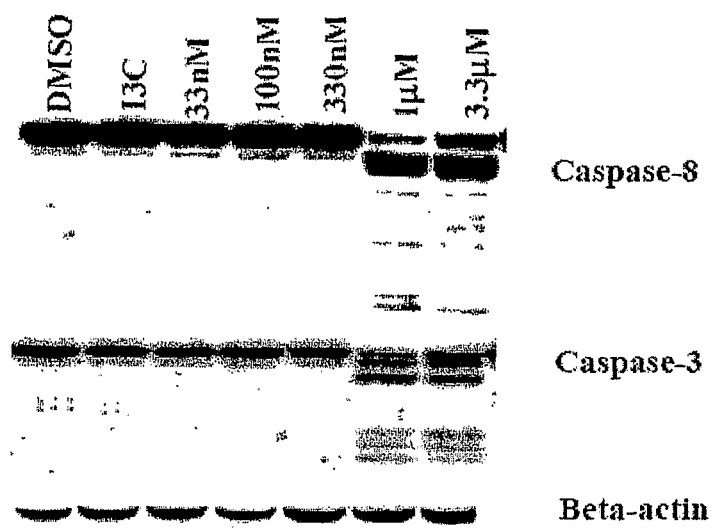

Induction of apoptosis by Oncrasin. Many antitumor therapies act by inducing apoptosis in tumor cells (Fisher, 1994; Thompson, 1995). To determine whether the antitumor activity of Oncrasin-1 is due to the suppression of cell proliferation or to cell killing, T29, T29Kt1, and H460 cells were stained with annexin V/propidium iodide (PI) after treatment with Oncrasin-1 at 30 μM (for T29 or T29Kt1 cells) or 3 μM (for H460 cells). After 12-24 h, 70% to 90% of H460 and T29Kt1 cells showed staining with annexin V, PI, or both (FIG. 3A), indicating that most of the cells were killed by Oncrasin-1. In contrast; <10% of the control H1460 and T29Kt1 cells, which were treated with DMSO, and the T29 cells treated with Oncrasin-1 were stained with annexin V or PI. This result indicated that Oncrasin-1 can effectively induce cell killing in T29Kt1 and H460 cells. Western blot analysis showed further that the treatment of H460 cells with 1 μM Oncrasin-1 effectively activated caspase-3 and caspase-8 (FIG. 3B), indicating that its cytotoxic effect in cancer cells is due to its induction of apoptosis.

Figure 4A:
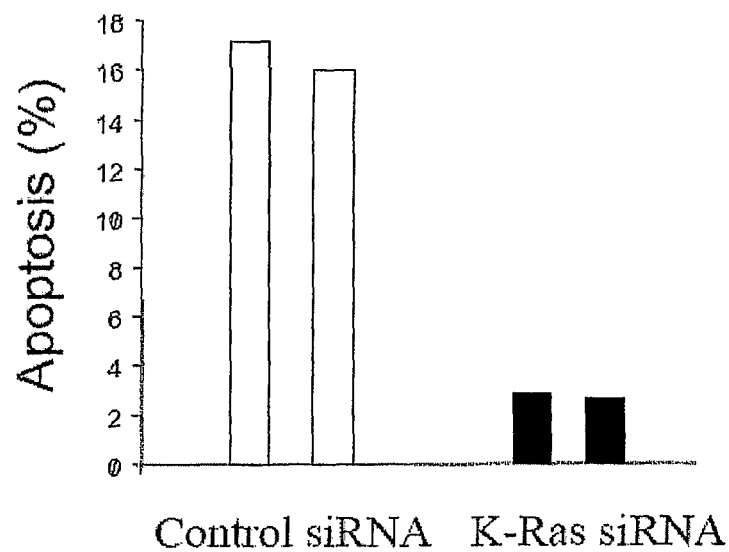
FIGS. 4A and 4B K-Ras knockdown inhibited Oncrasin-mediated apoptosis.
Figure 4B:
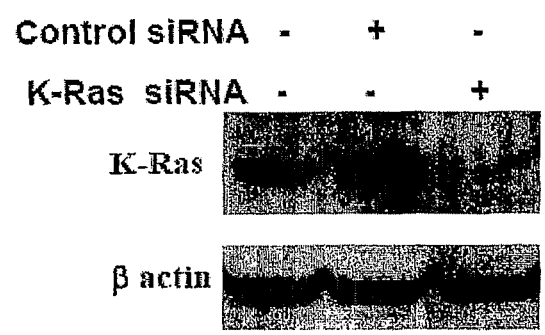

K-Ras knockdown inhibited Oncrasin-induced apoptosis. To further study the role of K-Ras gene in Oncrasin-induced cell death, H460 cells were treated with 200 μM of K-Ras specific siRNA or a control siRNA for 24 h. The cells were then treated with DMSO or 1 μM Oncrasin-1. After another 12 h, the cells were harvested for apoptosis detection by fluorescence-activated cytometric assay. The cell lysate was also used to detect K-Ras gene expression. The results showed that treatment with K-Ras specific siRNA but not a control siRNA suppressed K-Ras expression in H460 cells. In cells treated with control siRNA, treatment with Oncrasin-1 resulted in a dramatic increase of apoptotic cells, when compared with DMSO cells. In contrast, in K-Ras siRNA treated cells, treatment with Oncrasin-1 have the similar levels of apoptosis as that of DMSO (FIG. 4). This result demonstrated that K-Ras activity is indeed required for Oncrasin-1 induced apoptosis in H460 cells.

Figure 5:
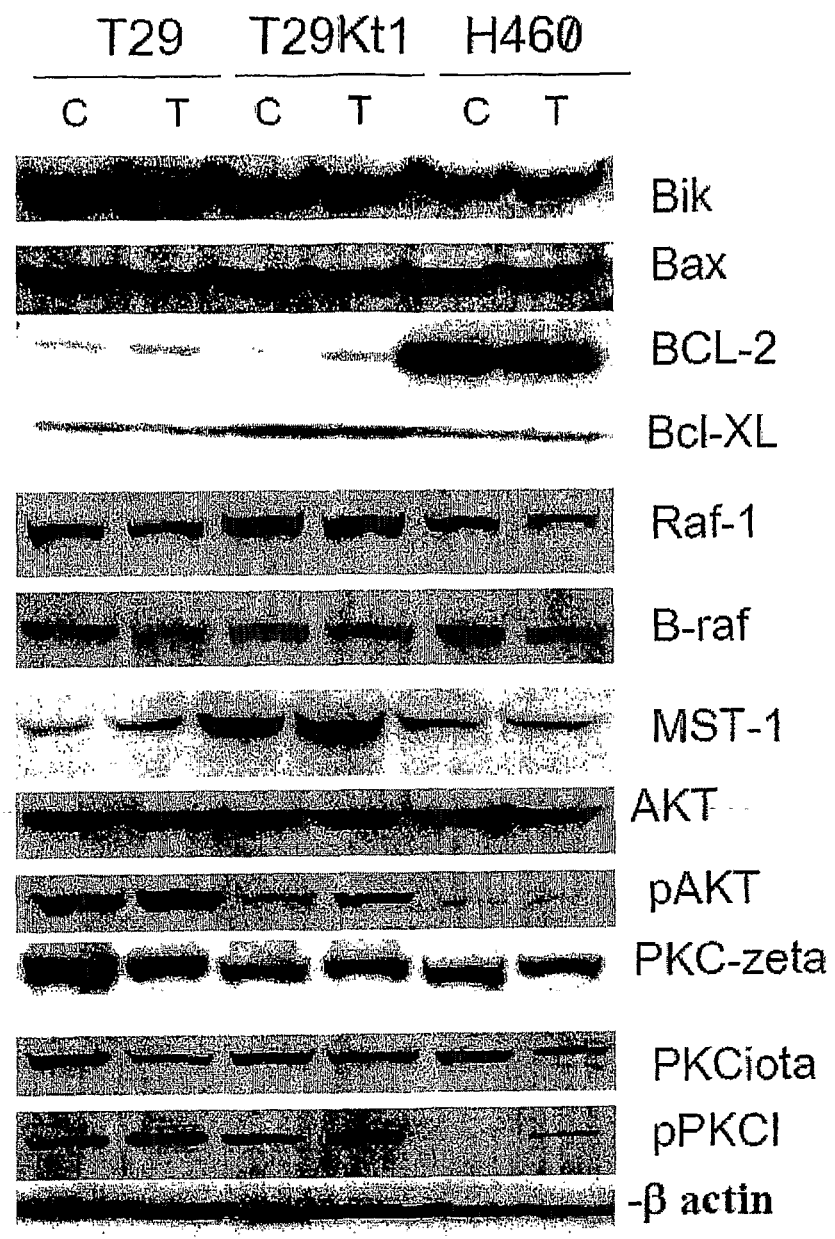
FIG. 5 Molecular changes in resistant and susceptible cells. T29, T29Kt1 and H460 cells were treated with 10 μM (for T29 and T29Kt1) or 1 μM (for H460) Oncrasin-1. 12 h later, the cells were harvested for Western blot analysis for molecules indicated on the right of panel. Cells treated with DMSO were used as control (C). T, cells treated with Oncrasin-1

Ras Signaling Pathway and Molecular Mechanisms of Oncrasin-induced apoptosis. To investigate molecular mechanisms of apoptosis induction by Oncrasin compounds, levels several proteins that are involved in apoptosis and/or involved in Ras signaling pathways were determined, including Bax, Bik, Bcl2, Bcl-XL, Raf-1, B-Raf, Akt, Mst1 and atypical protein kinase C (aPKC) zeta and PKCiota. To study which molecules are affected by Oncrasin treatment, T29, T29Kt1 and H460 cells were treated with Oncrasin-1 at an optimal concentration, around $IC_{60}$ to $IC_{80}$ for T29Kt1 and H460 cells. Cell lysates were collected 12 h after the treatment and subjected to Western blot analysis. The results showed that treatment with Oncrasin-1 did not result in noticeable changes in the levels of Bax, Bik, Bcl-2, Bcl-XL, Mst1, B-Raf, PKCzeta and PKCiota. Treatment with Oncrasin-1 resulted in down regulation of Raf-1 and Akt in H460 cell but not in T29 and T29K cells. Interestingly, treatment with Oncrasin-1 resulted in an increase in phosphorylated PKCiota in both Oncrasin-1 susceptible cells H460 and T29K but not in Oncrasin-1 resistant T29 cells (FIG. 5).

Figure 6A:
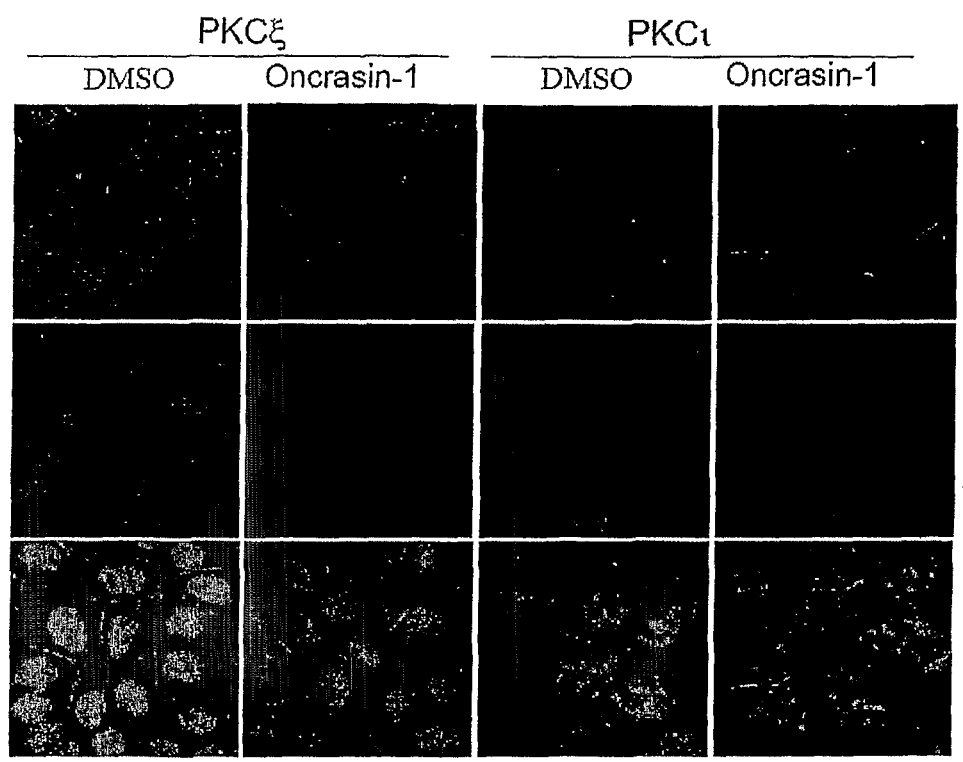
FIGS. 6A-6C Oncrasin-induced aggregation of PKCiota (PKCI). Cells were treated with DMSO or Oncrasin-1 for 12 h and immunohistochemical staining were performed to test PKCzeta and PKCiota in H460 (FIG. 6A) and T29Kt1 (FIG. 6B) cells.
Figure 6B:
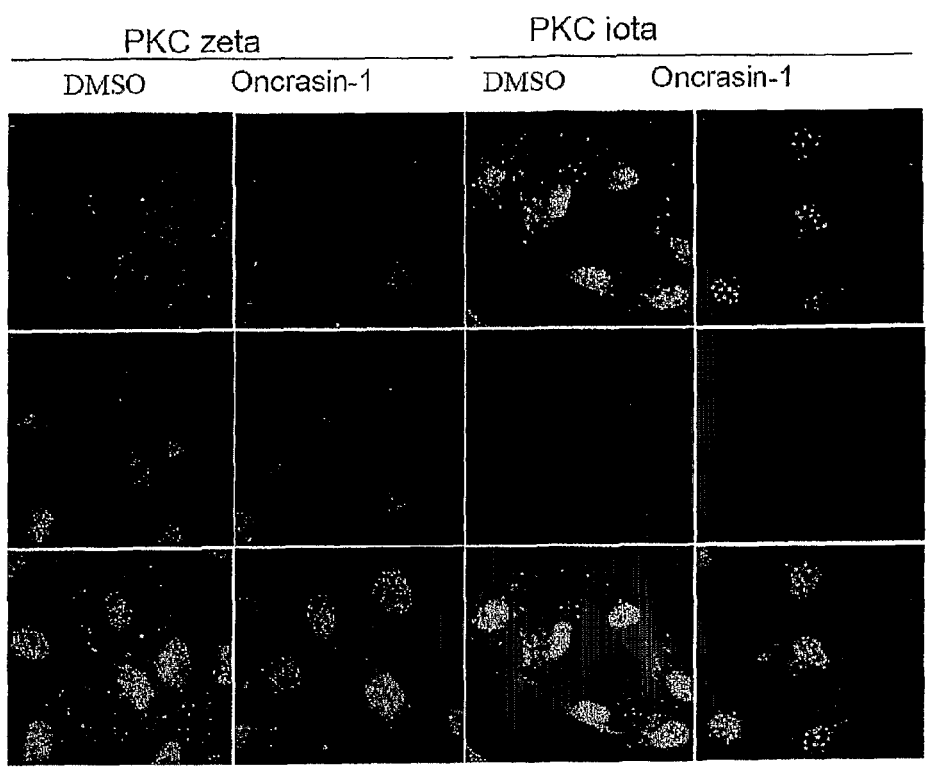

Effects on subcellular localization of PKCiota. The Western blot analysis did not provide definitive information in terms of the mechanisms of Oncrasin-induced apoptosis. To further investigate molecular mechanisms of Oncrasin action the inventors studied the subcellular localization of several molecules involved in Ras-signaling pathway because the functions of Ras and other proteins are directly related to their subcellular localizations. For this purpose, T29Kt1 or H460 cells were seeded on cover glass slides and treated with DMSO or Oncrasin-1 for 12 h. Cells were then fixed with paraformaldehyde, permeabilized with Triton X-100 and stained with various antibodies for immunohistochemical examination. Treatment of Oncrasin did not induce obvious changes in subcellular localization of Raf-1, Akt, PKCzeta, PKCdelta, and p53. Nevertheless, substantial subcellular localization change was detected for PKCiota after Oncrasin-1 treatment (FIG. 6). In both H460 and T29Kt1 cells, both PKCiota and PKCzeta were diffusely distributed in cells with high concentration on cell membrane in nucleus, consisting with previous reports that aPKC contains both nuclear localization signal (NLS) and nuclear export signal (NES), and can shuttle between cytoplasm and nucleus, which was regulated by intramolecular conformational changes, phosphorylation or by treatment with growth factors (Perander et al., 2001; White et al., 2002; Neri et al., 1999). Treatment with PBS or DMSO did not result in obvious changes of aPKC subcellular distributions. Treatment with Oncrasin-1 also did not result in obvious change of subcellular localization of PKCzeta. Interestingly, treatment with Oncrasin-1 resulted in aggregation of PKCiota into large foci in nucleus in both T29Kt1 cells and H460. Such aggregation of PKCiota was not observed in Oncrasin-resistant T29 and H1299 cells. The inventors then tested whether PKCiota aggregation in the nucleus can be induced by other chemotherapeutic agents such as 5-fluorouracil (5-FU) and paclitaxol. The result showed that treatment of T29Kt1 cells with chemotherapeutic agents 5-FLY, taxol, or radiation at doses that resulted in similar cell killing as Oncrasin-1 did not induce PKCiota aggregation in the nucleus. Treatment with PI3K inhibitor LY294003 64 also did not induce PKCiota aggregation, suggesting that PKCioata aggregation in the nucleus is not a general phenomenon occurring in dying cells.

Figure 8A:
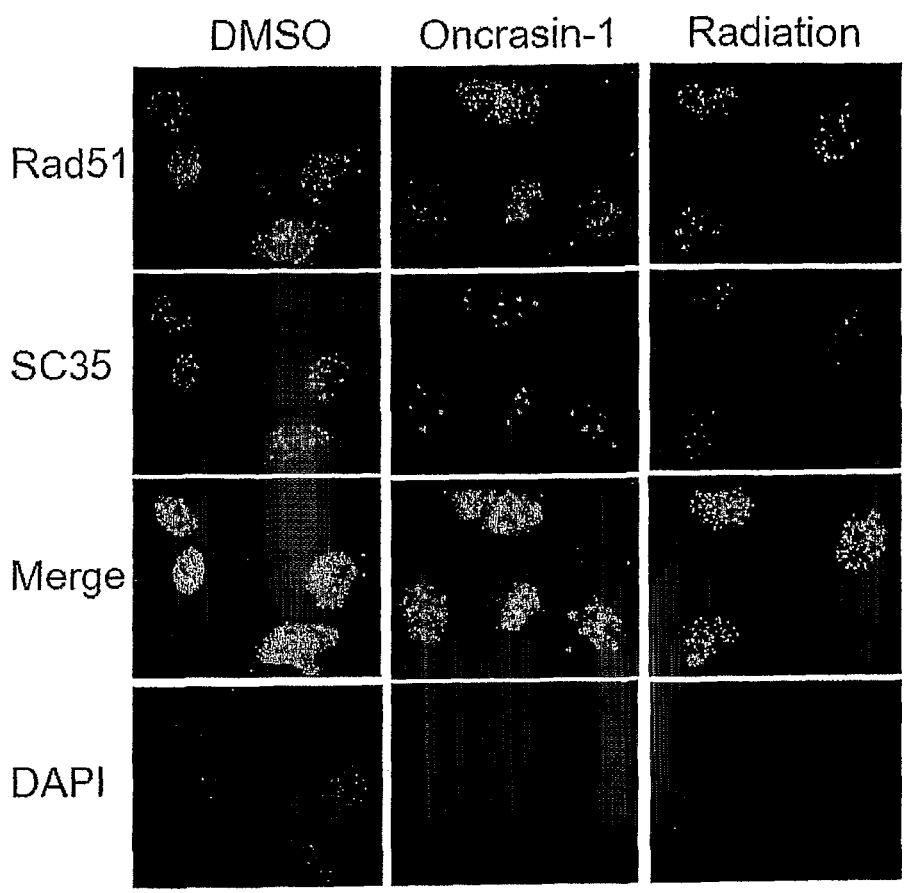
FIGS. 8A-8D Induction of mega-spliceosome speckles by Oncrasin-1.
Figure 8B:
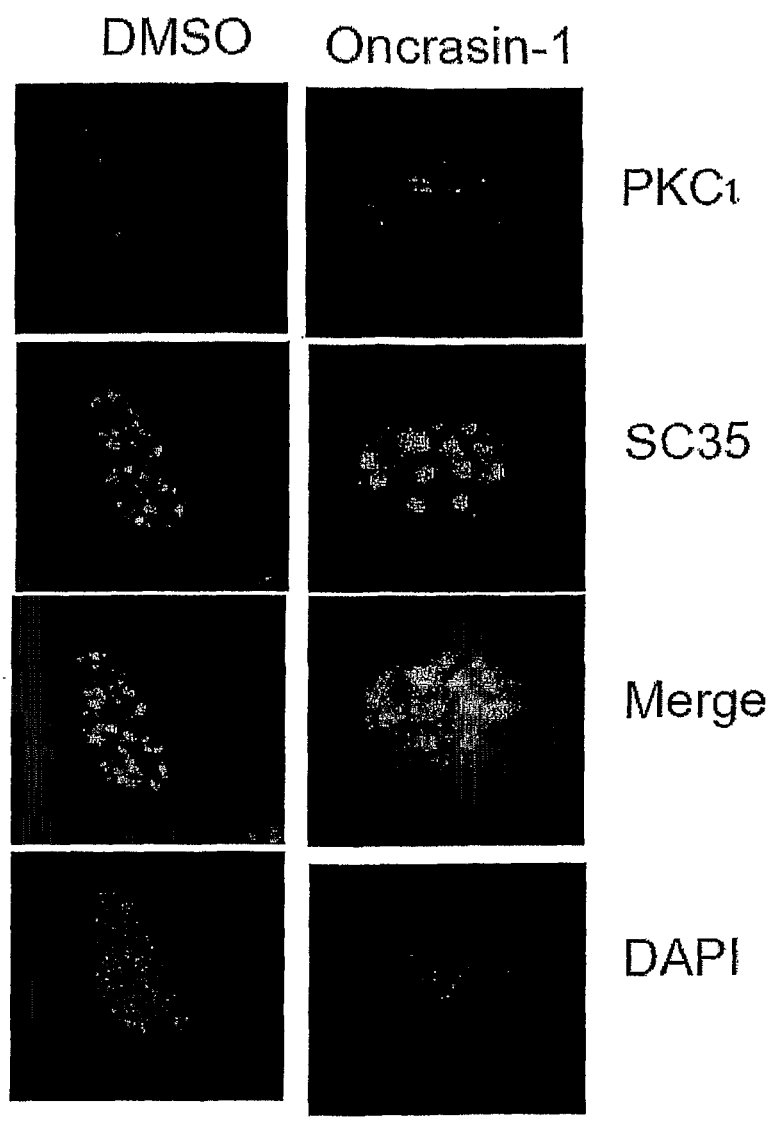
Figure 8C:
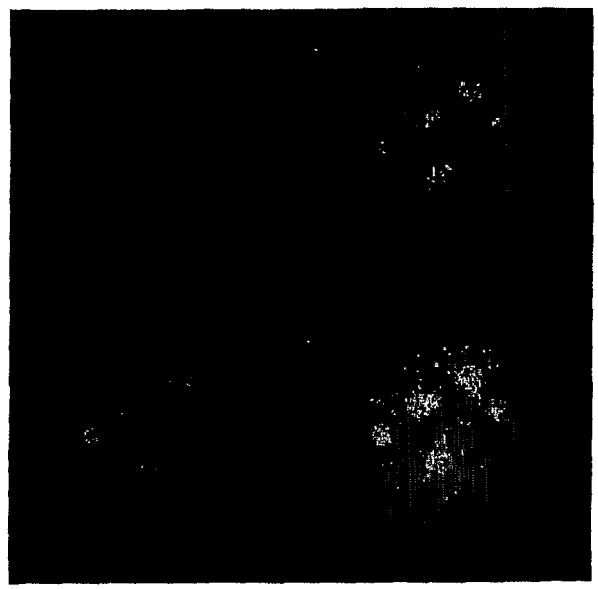
Figure 8D:
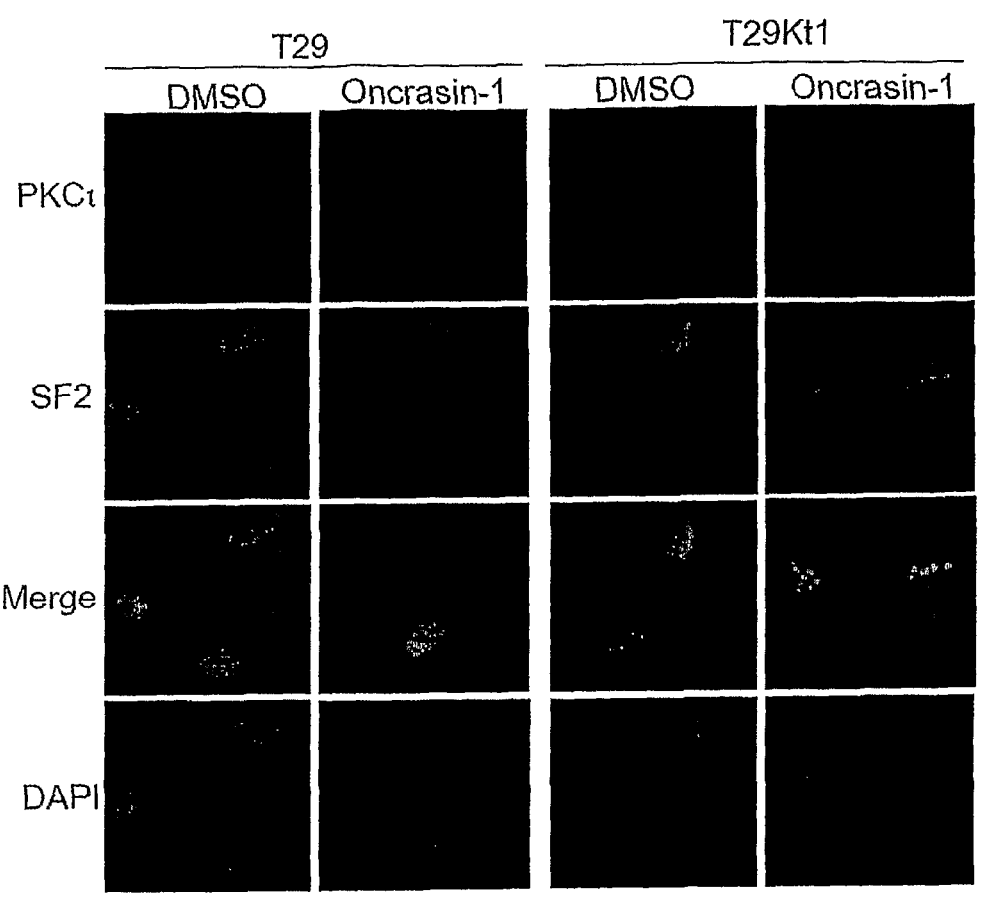

Effects on RNA spliceosome. To investigate the nature of this PKCiota aggregates in the nucleus, the effect of Oncrasin-1 on SC35, a protein required for RNA splicing and assembly of spliceosome (Fu et al., 1992; Vellard et al., 1992), and on Rad51, a homologous DNA recombinase that involves in DNA repair (Benson et al., 1994; Baumann et al., 1996) were studied. ANA processing and DNA repairing are the two important functions executed in the nucleus. In untreated or DMSO-treated cells, SC35 was localized in nucleus as speckles, either diffusely distributed or concentrated as granule clusters (Mistele et al., 1997), whereas Rad51 was more uniformly distributed inside the nucleus. Treatment of T29Kt1 cells with Oncrasin-1 resulted in aggregation of SC35 into several large foci, a phenomenon similar to that seen for PKCiota (FIG. 8). This aggregation of SC35 was not observed in Oncrasin resistant T29 cells upon the treatment with Oncrasin-1. On the other hand, treatment with radiation (10 gray) resulted in formation of tiny foci of Rad51 in nucleus, without noticeable effect on SC35. Nevertheless, treatment with Oncrasin-1 had no obvious effect for Rad51. Immunohistochemical co-staining of PKCiota and SC35 showed that, upon the treatment of Oncrasin-1, PKCiota and SC35 were co-localized in the mega spliceosome. This result was confirmed by examination under confocal microscope (FIG. 8B). The effects of Oncrasin on another spliceosome protein, alternative splicing factor/splicing factor 2 (ASF/SF2), was studied (Krainer et al., 1991). Similar to SC35, treatment with Oncrasin-1 induced ASF/SF2 aggregation inside nucleus in sensitive T29Kt1 cells that overlaps with PKCiota. In the resistant T29 cells, however, such an aggregation is not observed (FIG. 8C).

Splicing factors like SC35 and ASF/SF2 are present in mammalian cell nucleus in high concentrations in compartments called speckles. Under electron microscopy, speckles are consisting of morphologically two distinct parts: (1) the larger and more concentrated regions referred as interchromatin granule clusters (IGCs), which are inactive for transcription and serves as a storage pools for splicing factors; (2) the more diffusely distributed splicing factors at regions of the periphery of IGCs correspond to perichromatin fibrils, which contain nascent transcripts and active spliceosome (Spector et al., 1993; Fakan et al., 1978). The morphology of spliceosome speckles is dynamically changing between IGCs and perichromatin fibrils, a process affected by RNA polymerase II-mediated transcription (isteli et al., 1997). Upon inhibition of RNA polymerase II transcription (Camo-Fonseca et al., 1992; Zeng et al., 1997) or pre-mRNA splicing by antisense oligos or antibodies (O'Keefe et al., 1994), splicing factors redistribute and preferentially localize to interchromatin granule clusters, which become larger and more uniform in shape, or become mega-spliceosome speckles. Thus, Oncrasin-mediated aggregation of SC35 and ASF/SF2 into mega foci suggested that Oncrasin compounds may suppress either RNA transcription or splicing. Together, the above results indicate that Oncrasin compounds may not be DNA damaging agents but the agents that interrupt RNA processing, either transcription, splicing, or both.

Figure 6C:
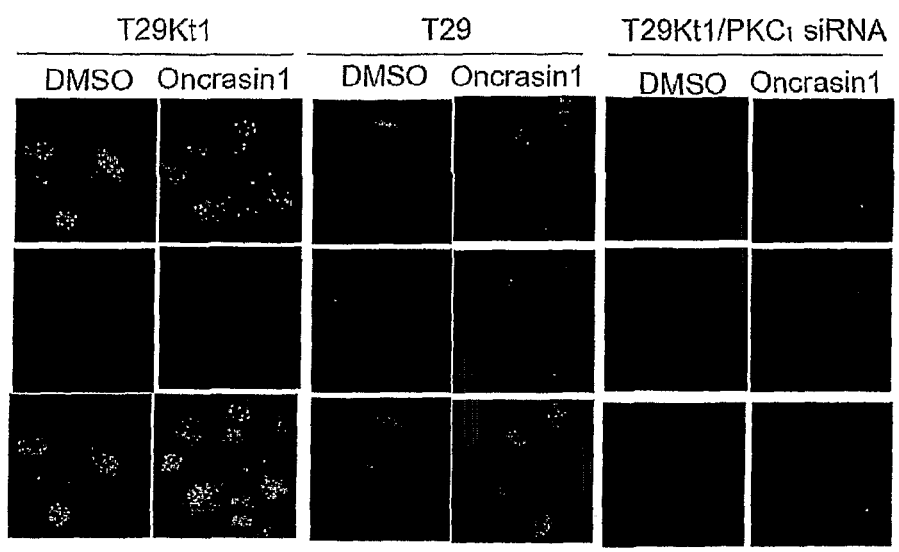
Figure 7:
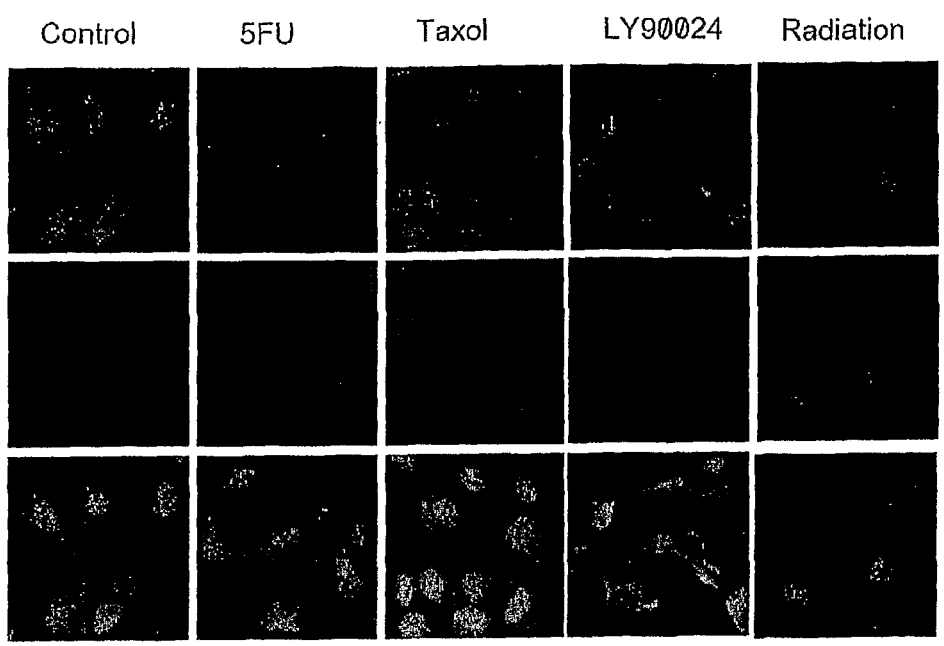
FIG. 7 Subcellular localization of PKCiota in T29Kt1 cells treated with different anticancer agents.

Knockdown of PKCiota suppressed Oncrasin-mediated apoptosis and cytotoxicity. To investigate possible role of PCKiota in Oncrasin-1 mediated cytotoxicity, PKCiota was knocked down in H460 cells by using oligo ribonucleotides. H460 cells were treated with 200 pM PKCiota siRNA for 24 h, and then with DMSO or 1 μM Oncrasin for another 12 h. After that, cells harvested for analysis of apoptosis by fluorescence-activated cell sorting (FACS) and for expression of PKCiota by Western blot analysis. The results showed that knockdown of PKCiota by siRNA also dramatically suppressed Oncrasin-induced apoptosis in H460 cells (FIG. 9A). To further study the effect of atypical PKC in Oncrasin-induced cytotoxicity, the inventors obtained plasmids encoding PKCiota and PKCzeta siRNA from Origene Corporation and made stable PKCiota and PKCzeta knockdown T29Kt1 cells. As shown in FIG. 6C, stably knockdown of PKCiota in T29Kt1 cells abolished PKCiota aggregation into foci in nucleus. Cell viability analysis showed that stably knockdown of PKCiota in T29Kt1 cells by siRNA constructs resulted in almost complete resistance to Oncrasin-1. The $IC_{50}$ in PKCiota knockdown T29Kt1 cells were 100 fold higher than parental T29K cells. This value is comparable to that of Oncrasin-resistant T29 cells. In contrast, knockdown of PKCiota by the same vector system did not change the susceptibility of T29Kt1 cells to Oncrasin. Those results indicate that Oncrasin-mediated cytotoxicity is also related to PKCiota activity which is reportedly required for Ras-induced oncogenesis (Murray et al., 2004). Recently, it was found that the PKCiota gene is amplified in about 44% of ovarian cancers (Zhang et al., 2006) and that overexpression of PKCiota predict poor survival in lung and ovarian cancer patients (Regala et al., 2005; eder et al., 2005). Thus, compounds with synthetic lethality for PKCiota might be useful for treatment of those cancers.

Figure 10A:
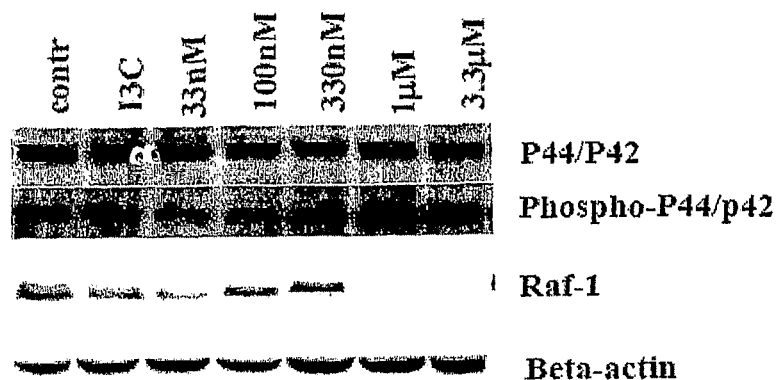
FIGS. 10A-10D Effect of Oncrasin-1 on Raf-1 expression.
Figure 10B:
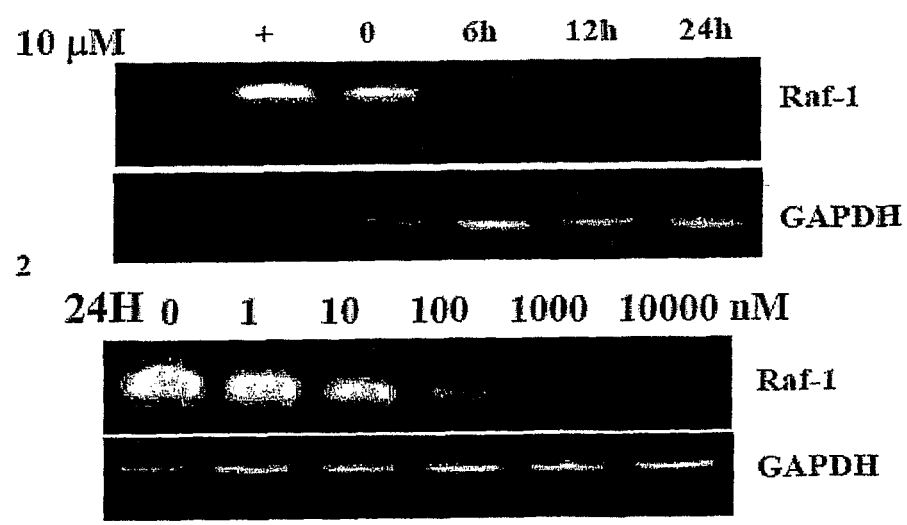
Figure 10C:
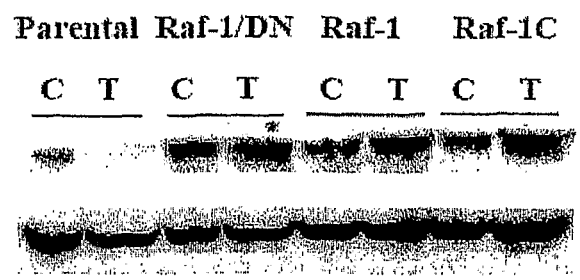
Figure 10D:
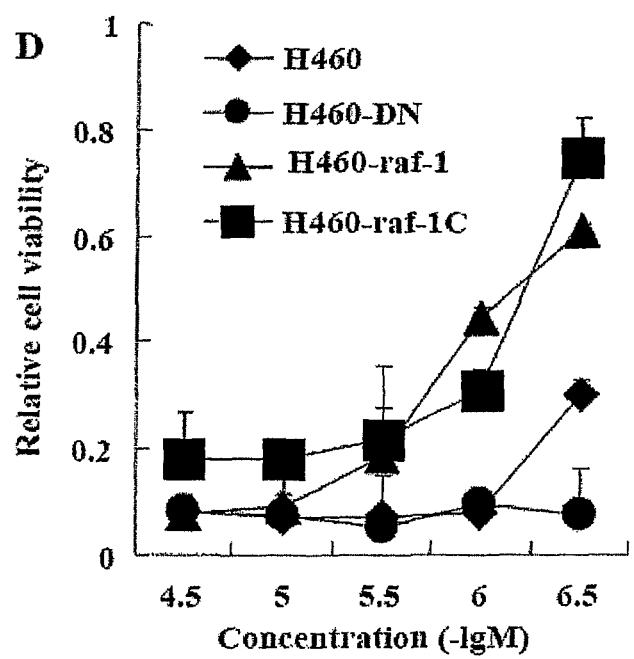

Suppression of Raf-1 expression by Oncrasin-1. The Western blot analysis shown in FIG. 5 indicates that Raf-1 expression was down regulated in H460 cells after treatment with Oncrasin-1. To elucidate the roles of Raf-1 in Oncrasin-induced apoptosis, the inventors evaluated the expression of Raf-1 in H460 cells after treatment with different concentrations of Oncrasin-1. Western blot analysis showed that the treatment of H460 cells with Oncrasin-1 dramatically reduced Raf-1 production (FIG. 10A). Reverse transcriptase-coupled polymerase chain reaction (RT-PCR) analysis further showed that the Raf-1 mRNA level decreased in a dose- and time-dependent fashion after Oncrasin-1 treatment (FIG. 10B), suggesting that the downregulation of Raf-1 occurred at the RNA level. Whether this down regulation of Raf-1 in H460 cells was correlated to interruption of RNA processing or formation of mega-speckles is not clear. However, down regulation of Raf-1 did not result in suppression of ERK as phosphorylation of ERK was increased at the same samples. Because Raf-1 executes anti-apoptosis function via a variety of pathways. The inventors studied whether down regulation of Raf-1 contributes to Oncrasin-1 induced apoptosis by stably transfected H460 cells with wild-type Raf-1, constitutively active Raf-1, and dominant-negative Raf-1 and tested their effects on the response to Oncrasin-1. Because the plasmid constructs used do not contain introns, the expression of those constructs were likely not affected by RNA splicing. Study on those stably transfected cells showed that H1460 cells transfected with wild-type or constitutively active Raf-1 were less susceptible than parental H460 cells to Oncrasin-1. However, the resistance to Oncrasin-1 was more prominent in the constitutively active Raf-1-transfected cells than in cells with the wild-type Raf-1 (FIG. 10C and FIG. 10D). In contrast, transfection with the dominant-negative form of Raf-1 rendered H460 cells more sensitive to Oncrasin-1. This result demonstrated that the cellular status of Raf-1 could dramatically affect the response to Oncrasin compounds.

Figure 11A:
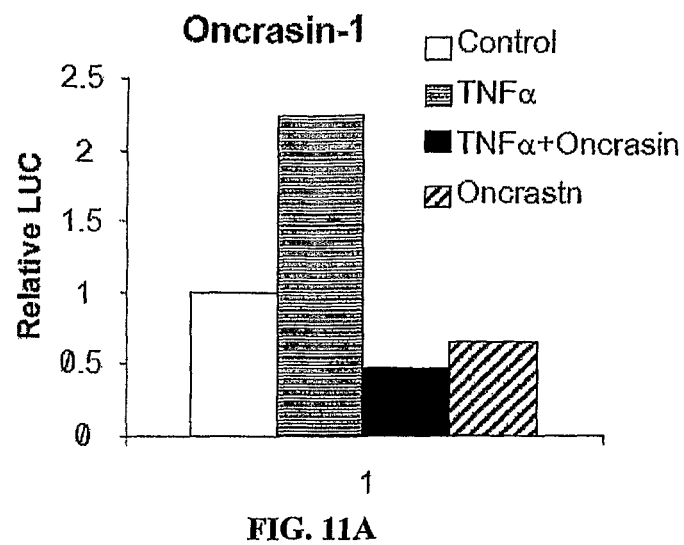
FIGS. 11A-11C Suppression of TNFα-induced NFκB activation. NKκB reporter plasmid assay. T29K cells were transfected with pNFκB-Luc and pCMV-lacZ. 12 h later, the cells were treated with TNFα (1 ng/ml) with or without (FIG. 11A) Oncrasin-1 (10 μM) or (FIG. 11B) Sulindac (10 μm). The luciferase activity was determined at 8 h after the treatment and normalized with beta-gal activity.
Figure 11B:
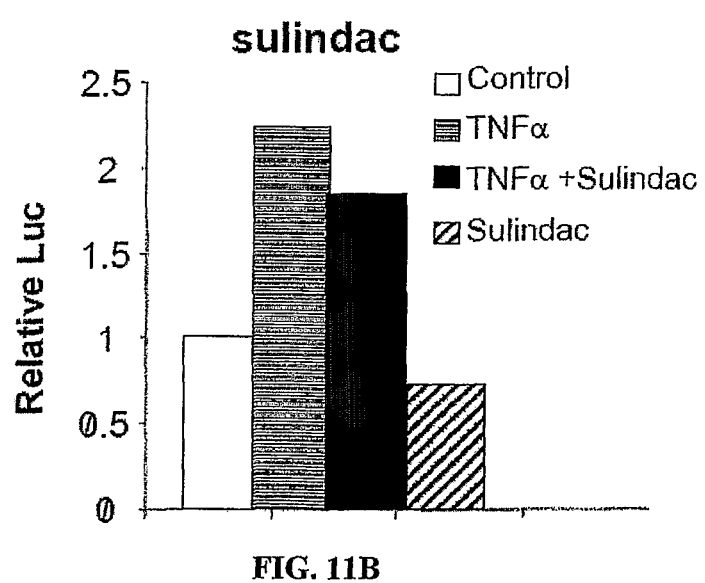
Figure 11C:
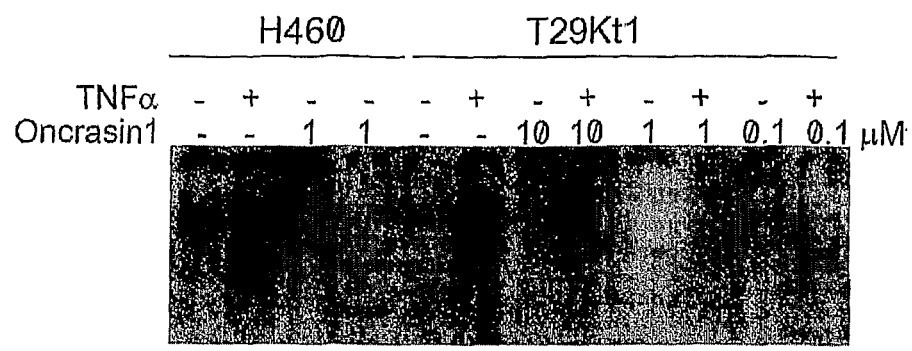

Suppression of NFκB. In a separated study, the effect of Oncrasin compounds on NF-κB activity was assessed. Nuclear factor-κB (NF-κB)/Rel represents a group of structurally related and evolutionarily conserved transcriptional factors that play critical roles in chronic and acute inflammatory diseases, autoimmune diseases and various type of cancers (Karin and Neriah, 2000; Karin and Karin, 2006; Barnes et al., 1997). In unstimulated cells, most NF-κB/Rel dimers are bound to IκBs and retained in the cytoplasm. Upon a various stimulations, IκBs are phosphorylated and rapidly degraded, releasing NF-κB, which then enters the nucleus and executes transcriptional functions. Because of its critical roles in inflammatory diseases and in cancer developments, NFκB pathway is an important target in treatment of those diseases (Karin et al., 2004). Several non-steroidal anti-inflammatory drugs such as sulindac and aspirin are capable of inhibiting NFκB activation (Yamamoto et al., 1999; Yin et al., 1998). Because Oncrasin compounds have some structure similarity as sulindac, the effects of Oncrasin-1 and sulindac on tumor-necrosis factor α (TNFα)-mediated NFκB activation in T29Kt1 cells was compared. T29Kt1 cells transfected with the plasmid pNFκB-Luc (from Clontech Corp. San Diego, Calif.) which expresses luciferase from a synthetic promoter containing four tandem copies of the NFκB consensus sequence and a TATA-like sequence. A plasmid expressing CMV-lacZ gene was used as a control for transfection. Twenty-four hours after the transfection, the cells were treated with TNFα (1 ng/ml) with or without 10 μM Oncrasin-1 or 10 μM Sulindac. Cells were harvested eight hours after the treatment. The luciferase activity was determined and normalized for transfection with beta-galactosidase activity. The results showed that Oncrasin-1 is more active than Sulindac in suppressing TNFα-induced NFκB activation (FIG. 11A). To further test the effect of Oncrasin-1 on NFκB activation, H460 and T29Kt1 cells treated with DMSO or Oncrasin-1 at various concentrations, with or without 1 ng/ml of TNFα. Twelve hours later, cell lysates were harvested and were subjected to nuclear extracts and electrophoretic mobility shift assay (EMSA) as we have previously described (Zhu et al., 2005). The results showed that at concentrations of 1 μM or above, Oncrasin-1 can effectively suppress TNFα-mediated NFκB activation in both H460 and T29Kt1 cells (FIG. 11B). Because NFκB not only plays critical roles in cancer development and progression but also is an important factor in cells' resistance to apoptosis-induction by other anticancer agents (Karin and Karin, 2006), the suppressive effect on NFκB activation indicates that Oncrasin-1 could be useful for combination therapy with other anticancer agents or for palliative treatment of pain and cachexia.

Example 2

Oncrasin and Oncrasin Analogs

The inventors submitted two compounds, Oncrasin-27 and Oncrasin-60 to the National Cancer Center (NCI) for testing in a panel of 60 cancer cell lines derived from various tissues or organs. The tests performed at NCI showed that Oncrasin-27 and Oncrasin-60 had similar anticancer spectrum and were active in a number of cancer cell lines derived from leukemia, non small lung cancer, colon cancer, melanoma, ovarian cancer, renal cancer and breast cancer (see Table 3A and 3B). For example, of 54 cell cancer cell lines tested, the medium 50% growth inhibition ($GI_{50}$) concentration for Oncrasin-60 is 1.12 μM. 17 cell lines (31%) have $GI_{50}$<1 μM; and 12 (22%) cell lines have $GI_{50}$ below 0.1 μM; 5 cell lines (9.3%) have $GI_{50}$<10 nM. Those results demonstrated that Oncrasin compounds could be effective against a variety of cancers with high potency. According to gene mutation data for NCI 60 cancer cell lines (sanger.ac.uk/genetics/CGP/NCI60/), the inventors compared gene mutations in the sensitive and resistant cell lines. The result showed that 35% of sensitive cell lines have K-Ras mutations versus 14% in resistant cell lines. Twenty-four percent of sensitive cell lines contain mutations in PI3K catalytic subunit (PIK3CA) versus 8% in resistant cells. The percentage of cell lines containing mutations in p53, p16, and PTEN genes are comparable among sensitive and resistant cells (Table 4A and 4B). Thus, those data also suggested that Oncrasin compounds may be useful for treatment of cancers containing K-Ras or PI3K mutation. It is also interesting that 65% of sensitive cancer cells have wild-type K-Ras gene. Whether those cells have increased Ras activity or increased PKCiota activity is not yet clear. Nevertheless, the results indicate that Oncrasin compounds are effective against some cancers even if they do not have K-Ras gene mutations.

TABLE 3A

Oncrasin 60
National Cancer Institute Developmental Therapeutics Program
In-Vitro Testing Results NSC: D741909/1  Experiment ID: 0606RS75  Test Type: 08  Units: Molar
Report Date: Oct. 03, 2006  Test Date: Jun. 26, 2006  QNS:  MC:
COMI: FL-K60 (48727)  Stain Reagent: SRB Dual-Pass Related  SSPL: OPNH

| Panel/Cell Line | Time Zero | Ctrl | Mean Optical Densities Log10 Concentration | | | | | Percent Growth Log10 Concentration | | | | | GI50 | TGI | LC50 |
|---|---|---|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 | | | |
| Leukemia | | | | | | | | | | | | | | | |
| CCRF-CEM | 0.349 | 1.946 | 1.946 | 1.900 | 1.841 | 0.167 | 0.116 | 100 | 97 | 81 | −47 | −67 | 1.74E−6 | 4.31E−6 | 1.48E−5 |
| HL-60(TB) | 0.321 | 1.182 | 1.135 | 1.057 | 0.918 | 0.402 | 0.072 | 95 | 85 | 89 | 9 | −78 | 2.10E−6 | 1.28E−5 | 4.31E−6 |
| K-562 | 0.092 | 0.641 | 0.717 | 0.840 | 0.468 | 0.135 | 0.027 | 114 | 100 | 67 | 8 | −71 | 1.92E−5 | 1.26E−6 | 6.46E−6 |
| MOLT-4 | 0.471 | 1.801 | 1.982 | 1.827 | 1.921 | 1.630 | 0.177 | 114 | 102 | 109 | 87 | −62 | 1.77E−6 | 3.82E−5 | 8.28E−5 |
| RPMI-8226 | 0.379 | 1.513 | 1.733 | 1.341 | 0.649 | 0.290 | 0.248 | 119 | 85 | 24 | −23 | −35 | 3.72E−7 | 3.19E−6 | >1.00E−4 |
| SR | 0.575 | 1.138 | 0.818 | 0.429 | 0.166 | 0.474 | 0.167 | 43 | −26 | −71 | −18 | −71 | <1.00E−6 | 1.26E−8 | — |
| Non-Small Cell Lung Cancer | | | | | | | | | | | | | | | |
| EKVX | 0.809 | 1.582 | 1.511 | 1.828 | 1.662 | 1.526 | 0.470 | 103 | 105 | 107 | 94 | −22 | 2.40E−5 | 6.47E−5 | >1.00E−4 |
| HOP-62 | 0.474 | 1.250 | 1.182 | 0.985 | 0.756 | 0.569 | 0.290 | 91 | 07 | 36 | 15 | −37 | 3.00E−7 | 1.93E−5 | >1.00E−4 |
| HOP-92 | 0.441 | 0.826 | 0.816 | 0.763 | 0.785 | 0.573 | 0.175 | 97 | 81 | 88 | 34 | −60 | 5.17E−6 | 2.39E−5 | 7.76E−5 |
| NCI-H226 | 0.479 | 0.935 | 0.884 | 0.375 | 0.182 | 0.151 | 0.168 | 40 | −22 | −82 | −68 | −65 | <1.00E−8 | 4.48E−8 | 5.01E−7 |
| NCI-H23 | 0.390 | 1.101 | 1.059 | 0.975 | 0.865 | 0.807 | 0.141 | 94 | 82 | 67 | 31 | −54 | 2.90E−6 | 2.10E−5 | 7.11E−5 |
| NCI-H322M | 0.541 | 1.147 | 1.258 | 1.262 | 1.200 | 0.870 | 0.418 | 118 | 117 | 109 | 54 | −23 | 1.13E−5 | 5.05E−5 | >1.00E−4 |
| NCI-H450 | 0.221 | 2.282 | 1.847 | 1.219 | 0.638 | 0.483 | 0.201 | 79 | 48 | 20 | 13 | −9 | 8.88E−8 | 3.79E−5 | >1.00E−4 |
| NCI-H622 | 0.711 | 1.541 | 1.465 | 1.392 | 1.344 | 0.773 | 0.187 | 91 | 82 | 76 | 7 | −74 | 2.41E−6 | 1.24E−5 | 5.10E−5 |
| Colon Cancer | | | | | | | | | | | | | | | |
| COLO 205 | 0.166 | 0.891 | 0.873 | 0.839 | 0.533 | 0.295 | 0.047 | 98 | 93 | 61 | 18 | −72 | 1.05E−6 | 1.58E−5 | 5.69E−5 |
| HCC-2998 | 0.388 | 1.199 | 1.162 | 1.088 | 0.887 | 0.740 | 0.012 | 95 | 86 | 62 | 43 | −97 | 4.33E−6 | 2.04E−5 | 4.52E−5 |
| HCT-116 | 0.265 | 2.129 | 1.526 | 0.625 | 0.448 | 0.296 | 0.095 | 68 | 30 | 10 | 2 | −64 | 2.04E−8 | 1.06E−5 | 6.06E−6 |
| HCT-15 | 0.308 | 1.654 | 1.635 | 1.514 | 1.238 | 0.597 | 0.214 | 99 | 90 | 69 | 21 | −31 | 2.52E−6 | 2.58E−5 | >1.00E−4 |
| HT20 | 0.266 | 1.860 | 1.910 | 1.533 | 1.183 | 0.725 | 0.090 | 103 | 79 | 68 | 29 | −66 | 1.83E−6 | 2.01E−6 | 6.76E−5 |
| KM12 | 0.400 | 1.365 | 1.441 | 1.495 | 1.387 | 1.236 | 0.156 | 108 | 113 | 102 | 87 | −64 | 1.83E−5 | 1.15E−6 | 9.44E−6 |
| SW-620 | 0.216 | 1.524 | 1.444 | 1.298 | 0.732 | 0.423 | 0.116 | 94 | 83 | 39 | 16 | −46 | 5.71E−7 | 1.80E−5 | >1.00E−4 |
| CNS Cancer | | | | | | | | | | | | | | | |
| SF-268 | 0.336 | 1.237 | 1.294 | 1.215 | 1.179 | 0.859 | 0.238 | 106 | 98 | 94 | 56 | −30 | 1.24E−5 | 4.58E−5 | >1.00E−4 |
| SF-295 | 0.711 | 2.300 | 2.364 | 1.964 | 1.603 | 0.991 | 0.608 | 104 | 80 | 56 | 18 | −15 | 1.43E−5 | 3.52E−5 | >1.00E−4 |
| SF-539 | 0.420 | 1.452 | 1.534 | 1.556 | 1.496 | 0.987 | 0.116 | 108 | 110 | 104 | 55 | −73 | 1.09E−5 | 2.70E−5 | 6.00E−5 |
| SNB-19 | 0.526 | 1.553 | 1.682 | 1.518 | 1.463 | 1.287 | 0.400 | 103 | 97 | 91 | 74 | −24 | 1.76E−5 | 5.69E−5 | >1.00E−4 |
| SNB-75 | 0.840 | 1.132 | 1.223 | 1.227 | 1.193 | 0.846 | 0.171 | 118 | 119 | 112 | 42 | −73 | 7.64E−5 | 2.31E−5 | 6.28E−5 |
| U251 | 0.394 | 1.765 | 1.673 | 1.550 | 1.299 | 0.737 | 0.258 | 93 | 84 | 55 | 25 | −35 | 2.46E−6 | 2.63E−5 | >1.00E−4 |
| Melanoma | | | | | | | | | | | | | | | |
| LOX IMVI | 0.386 | 2.087 | 2.124 | 2.007 | 2.024 | 0.814 | 0.053 | 102 | 96 | 96 | 26 | −86 | 4.48E−6 | 1.58E−6 | 4.72E−5 |
| MALME-3M | 0.517 | 0.731 | 0.742 | 0.760 | 0.704 | 0.592 | 0.217 | 105 | 114 | 88 | 35 | −58 | 5.17E−5 | 2.37E−5 | 8.20E−5 |
| M14 | 0.424 | 1.382 | 1.333 | 1.327 | 1.259 | 0.760 | 0.090 | 95 | 94 | 87 | 35 | −79 | 6.16E−6 | 2.03E−5 | 5.59E−5 |
| SK-MEL-2 | 0.797 | 1.353 | 1.341 | 1.285 | 1.172 | 0.640 | 0.287 | 98 | 84 | 67 | −20 | −64 | 1.58E−6 | 5.94E−6 | 4.82E−5 |
| SK-MEL-28 | 0.204 | 0.794 | 0.754 | 0.786 | 0.702 | 0.600 | 0.113 | 93 | 99 | 93 | 82 | −15 | 1.80E−5 | 4.44E−5 | >1.00E−4 |
| SK-MEL-5 | 0.295 | 1.709 | 1.633 | 1.602 | 1.339 | 0.855 | 0.010 | 95 | 92 | 74 | 40 | −97 | 4.97E−6 | 1.95E−5 | 4.55E−5 |
| UACC-62 | 0.727 | 2.107 | 1.885 | 1.238 | 0.715 | 0.383 | 0.041 | 79 | 35 | −2 | −47 | −94 | 4.51E−8 | 8.97E−7 | 1.14E−5 |
| Ovarian Cancer | | | | | | | | | | | | | | | |
| OVCAR-3 | 0.391 | 1.398 | 1.349 | 1.164 | 0.807 | 0.399 | 0.158 | 95 | 77 | 42 | 1 | −60 | 5.69E−7 | 1.03E−5 | 6.91E−5 |
| OVCAR-4 | 0.411 | 1.180 | 1.135 | 0.950 | 0.553 | 0.487 | 0.294 | 94 | 71 | 31 | 10 | −29 | 3.40E−7 | 1.80E−5 | >1.00E−4 |
| OVCAR-5 | 0.367 | 0.976 | 0.628 | 0.428 | 0.940 | 0.283 | 0.185 | 43 | 10 | −7 | −23 | −50 | <1.00E−8 | 3.72E−7 | >1.00E−4 |
| SK-OV-3 | 0.555 | 1.116 | 1.084 | 1.035 | 0.904 | 0.645 | 0.456 | 96 | 85 | 52 | 16 | −16 | 1.82E−6 | 2.96E−5 | >1.00E−4 |
| Renal Cancer | | | | | | | | | | | | | | | |
| 786-0 | 0.481 | 1.940 | 1.923 | 1.758 | 1.586 | 0.870 | 0.232 | 99 | 88 | 76 | 27 | −52 | 3.40E−5 | 2.19E−5 | 9.47E−5 |
| A498 | 0.926 | 1.692 | 1.394 | 0.408 | 0.120 | 0.048 | 0.056 | 61 | −56 | −87 | −95 | −94 | 1.24E−8 | 3.33E−8 | 8.90E−8 |
| ACHN | 0.489 | 1.601 | 1.589 | 1.516 | 1.323 | 0.608 | 0.345 | 99 | 92 | 75 | 10 | −30 | 2.00E−6 | 2.25E−5 | >1.00E−4 |
| CAK1-1 | 0.428 | 0.901 | 0.431 | 0.416 | 0.337 | 0.226 | 0.433 | 1 | −3 | −21 | −47 | 1 | <1.00E−8 | — | >1.00E−4 |
| RXF 393 | 0.268 | 0.630 | 0.380 | 0.295 | 0.237 | 0.186 | 0.041 | 31 | 7 | −12 | −30 | −85 | <1.00E−8 | 2.44E−7 | 2.32E−5 |
| SN12C | 0.806 | 2.736 | 2.103 | 2.047 | 1.874 | 1.234 | 0.308 | 97 | 93 | 78 | 27 | −68 | 3.56E−6 | 1.94E−5 | 8.72E−5 |
| TK-10 | 0.627 | 1.348 | 1.074 | 0.607 | 0.685 | 0.574 | 0.514 | 82 | −3 | −10 | −8 | −18 | 1.53E−8 | 8.94E−8 | >1.00E−4 |
| UO-31 | 0.507 | 1.373 | 1.290 | 1.200 | 1.026 | 0.594 | 0.292 | 90 | 80 | 60 | 10 | −42 | 1.58E−6 | 1.55E−5 | >1.00E−4 |
| Prostate Cancer | | | | | | | | | | | | | | | |
| DU-145 | 0.211 | 0.836 | 0.885 | 0.888 | 0.821 | 0.475 | 0.100 | 108 | 105 | 96 | 42 | −53 | 7.25E−6 | 2.78E−5 | 9.33E−5 |

TABLE 3A-continued

Oncrasin 60
National Cancer Institute Developmental Therapeutics Program
In-Vitro Testing Results Breast Cancer

| | | | | | | | | | | | | | | | |
|---|---|---|---|---|---|---|---|---|---|---|---|---|---|---|---|
| MCF7 | 0.377 | 2.090 | 1.653 | 1.146 | 0.551 | 0.509 | 0.340 | 75 | 45 | 10 | 8 | −10 | 5.73E-8 | 2.75E-5 | >1.00E-4 |
| NCI/ADR-RES | 0.347 | 1.162 | 1.191 | 1.117 | 1.045 | 0.744 | 0.192 | 103 | 94 | 86 | 49 | −45 | 9.22E-6 | 3.32E-5 | >1.00E-4 |
| MDA-MB-231/ATCC | 0.558 | 1.205 | 1.237 | 1.932 | 1.255 | 0.904 | 0.380 | 105 | 120 | 109 | 53 | −32 | 1.10E-5 | 4.23E-5 | >1.00E-4 |
| HS S78T | 0.425 | 0.996 | 1.023 | 0.984 | 0.946 | 0.595 | 0.263 | 105 | 98 | 91 | 30 | −36 | 4.68E-5 | 2.75E-5 | >1.00E-4 |
| MDA-MB-435 | 0.418 | 1.789 | 1.811 | 1.793 | 1.739 | 1.535 | 0.297 | 102 | 100 | 96 | 81 | −29 | 1.93E-5 | 5.47E-5 | >1.00E-4 |
| BT-549 | 0.426 | 0.794 | 0.831 | 0.856 | 0.782 | 0.524 | 0.066 | 110 | 118 | 97 | 26 | −85 | 4.62E-6 | 1.73E-5 | 4.88E-6 |
| T-47D | 0.537 | 1.284 | 1.079 | 0.684 | 0.474 | 0.453 | 0.465 | 73 | 20 | −12 | −16 | −14 | 2.67E-8 | 4.23E-7 | >1.00E-4 |

TABLE 3B

Oncrasin 60
National Cancer Institute Developmental Therapeutics Program
Mean Graphs

| Panel/Cell Line | Log$_{10}$ GI50 | GI50 |
|---|---|---|
| Leukemia | | |
| CCRF-CEM | −5.76 | |
| HL-60(TB) | −5.68 | |
| K-562 | −5.72 | |
| MOLT-4 | −4.75 | |
| RPMI-8226 | −6.43 | |
| SR | <−8.00 | |
| Non-Small Cell Lung Cancer | | |
| EKVX | −4.62 | |
| HOP-62 | −6.44 | |
| HOP-92 | −5.29 | |
| NCI-H226 | <−8.00 | |
| NCI-H23 | −5.54 | |
| NCI-H322M | −4.96 | |
| NCI-H460 | −7.05 | |
| NCI-H522 | −5.62 | |
| Colon Cancer | | |
| COLO 205 | −5.98 | |
| HCC-2998 | −5.36 | |
| HCT-116 | −7.53 | |
| HCT-15 | −5.60 | |
| HT29 | −5.74 | |
| KM12 | −4.74 | |
| SW-620 | −6.24 | |
| CNS Cancer | | |
| SF-268 | −4.91 | |
| SF-295 | −5.85 | |
| SF-539 | −4.96 | |
| SNB-19 | −4.75 | |
| SNB-75 | −5.12 | |
| U251 | −5.61 | |
| Melanoma | | |
| LOX IMVI | −5.35 | |
| MALME-3M | −5.29 | |
| M14 | −5.29 | |
| SK-MEL-2 | −5.80 | |
| SK-MEL-28 | −4.75 | |
| SK-MEL-5 | −5.30 | |
| UACC-62 | −7.35 | |

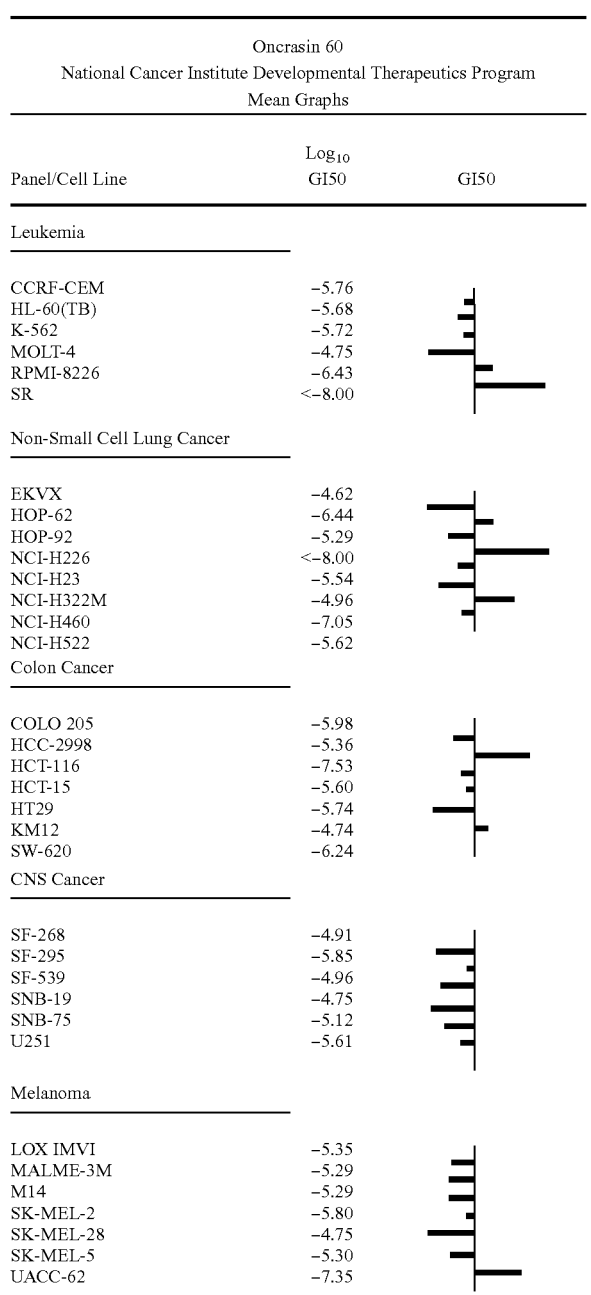

TABLE 3B-continued

Oncrasin 60
National Cancer Institute Developmental Therapeutics Program
Mean Graphs

| Panel/Cell Line | Log$_{10}$ GI50 | GI50 |
|---|---|---|
| Ovarian Cancer | | |
| OVCAR-3 | −6.24 | |
| OVCAR-4 | −6.47 | |
| OVCAR-5 | <−8.00 | |
| SK-OV-3 | −5.74 | |
| Renal Cancer | | |
| 786-0 | −5.47 | |
| A498 | −7.91 | |
| ACHN | −5.58 | |
| CAKI-1 | <−8.00 | |
| RXF 393 | <−8.00 | |
| SN12C | −5.45 | |
| TK-10 | −7.82 | |
| UO-31 | −5.80 | |
| | −5.14 | |
| Prostate Cancer | | |
| DU-145 | | |
| Breast Cancer | | |
| MCF7 | −7.17 | |
| NCI/ADR-RES | −5.04 | |
| MDA-MB-231/ATCC | −4.96 | |
| HS 578T | −5.33 | |
| MDA-MB-435 | −4.72 | |
| BT-549 | −5.34 | |
| T-47D | −7.57 | |
| MG_MID | −5.95 | |
| Delta | 2.05 | |
| Range | 3.38 | |

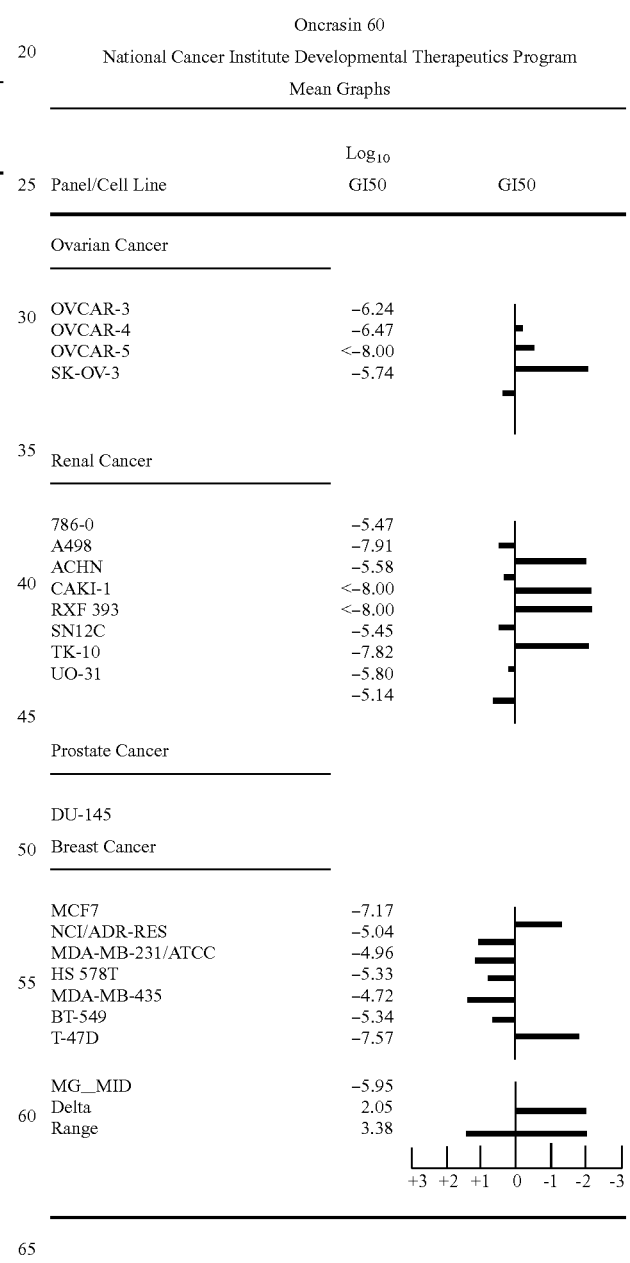

TABLE 4A

Oncrasin 27
National Cancer Institute Developmental Therapeutics Program
In-Vitro Testing Results NSC: D741909/1 Experiment ID: 0606RS75 Test Type: 08 Units: Molar
Report Date: Oct. 03, 2006 Test Date: Jun. 26, 2006 QNS: MC:
COMI: FL-K60 (48727) Stain Reagent: SRB Dual-Pass Related SSPL: 0PNH

| | Time | | Log10 Concentration | | | | | | | | | | | | | |
| | | | Mean Optical Densities | | | | | | Percent Growth | | | | | | | |
| Panel/Cell Line | Zero | Ctrl | −8.0 | −7.0 | −6.0 | −5.0 | −4.0 | −8.0 | −7.0 | −6.0 | −5.0 | −4.0 | GI50 | TGI | LC50 |
|---|---|---|---|---|---|---|---|---|---|---|---|---|---|---|---|
| Leukemia | | | | | | | | | | | | | | | |
| CCRF-CEM | 0.349 | 1.948 | 1.946 | 1.900 | 1.641 | 0.187 | 0.116 | 100 | 97 | 87 | −47 | −67 | 1.74E−6 | 4.31E−5 | 1.48E−5 |
| HL-60(TB) | 0.321 | 1.182 | 1.135 | 1.057 | 0.918 | 0.402 | 0.072 | 95 | 85 | 89 | 9 | −78 | 2.10E−6 | 1.28E−5 | 4.81E−5 |
| K-562 | 0.092 | 0.641 | 0.717 | 0.640 | 0.458 | 0.135 | 0.027 | 114 | 100 | 87 | 8 | −71 | 1.92E−8 | 1.26E−5 | 5.45E−5 |
| MOLT-4 | 0.471 | 1.807 | 1.982 | 1.827 | 1.928 | 1.630 | 0.177 | 114 | 102 | 109 | 87 | −62 | 1.77E−8 | 3.82E−5 | 8.26E−5 |
| RPMI-8226 | 0.379 | 1.513 | 1.733 | 1.941 | 0.849 | 0.290 | 0.248 | 119 | 85 | 24 | −23 | −35 | 3.72E−7 | 3.19E−6 | >1.00E−4 |
| SR | 0.576 | 1.138 | 0.818 | 0.429 | 0.168 | 0.474 | 0.187 | 43 | −25 | −71 | −18 | −71 | <1.00E−8 | 4.26E−8 | — |
| Non-Small Cell Lung Cancer | | | | | | | | | | | | | | | |
| EKVX | 0.609 | 1.582 | 1.611 | 1.628 | 1.852 | 1.525 | 0.476 | 103 | 105 | 107 | 94 | −22 | 2.10E−5 | 6.47E−5 | >1.00E−4 |
| HOP-62 | 0.474 | 1.250 | 1.102 | 0.885 | 0.756 | 0.509 | 0.298 | 91 | 87 | 35 | 15 | −37 | 3.50E−7 | 1.93E−5 | >1.00E−4 |
| HOP-92 | 0.441 | 0.826 | 0.616 | 0.763 | 0.785 | 0.573 | 0.175 | 97 | 81 | 89 | 34 | −60 | 5.17E−6 | 2.30E−6 | 7.78E−5 |
| NCI-H226 | 0.479 | 0.935 | 0.664 | 0.376 | 0.182 | 0.161 | 0.160 | 40 | −22 | −62 | −59 | −65 | <1.00E−8 | 4.46E−8 | 5.01E−7 |
| NCI-H23 | 0.380 | 1.101 | 1.059 | 0.875 | 0.555 | 0.507 | 0.141 | 94 | 82 | 57 | 31 | −54 | 2.90E−6 | 2.10E−5 | 7.11E−5 |
| NCI-H322M | 0.541 | 1.147 | 1.258 | 1.252 | 1.200 | 0.870 | 0.418 | 118 | 117 | 109 | 54 | −23 | 1.13E−5 | 5.05E−5 | >1.00E−4 |
| NCI-H450 | 0.221 | 2.282 | 1.847 | 1.219 | 0.698 | 0.483 | 0.201 | 79 | 48 | 20 | 13 | −9 | 8.88E−8 | 3.79E−5 | >1.00E−4 |
| NCI-H622 | 0.711 | 1.541 | 1.465 | 1.392 | 1.344 | 0.773 | 0.187 | 91 | 82 | 76 | 7 | −74 | 2.41E−6 | 1.24E−5 | 5.10E−5 |
| Colon Cancer | | | | | | | | | | | | | | | |
| COLO 205 | 0.166 | 0.891 | 0.873 | 0.839 | 0.533 | 0.295 | 0.047 | 88 | 93 | 51 | 18 | −72 | 1.05E−6 | 1.58E−5 | 5.69E−6 |
| HCC-2998 | 0.388 | 1.199 | 1.162 | 1.088 | 0.887 | 0.740 | 0.012 | 85 | 86 | 62 | 43 | −97 | 4.33E−6 | 2.04E−5 | 4.62E−5 |
| HCT-116 | 0.266 | 2.129 | 1.626 | 0.025 | 0.448 | 0.296 | 0.095 | 68 | 30 | 10 | 2 | −84 | 2.94E−6 | 1.06E−5 | 6.06E−5 |
| HCT-15 | 0.308 | 1.654 | 1.835 | 1.514 | 1.238 | 0.597 | 0.214 | 99 | 90 | 69 | 21 | −31 | 2.52E−8 | 2.58E−6 | >1.00E−4 |
| HT29 | 0.266 | 1.860 | 1.910 | 1.533 | 1.183 | 0.725 | 0.090 | 103 | 79 | 68 | 29 | −66 | 1.83E−9 | 2.01E−6 | 6.76E−6 |
| KM12 | 0.400 | 1.365 | 1.441 | 1.495 | 1.987 | 1.238 | 0.188 | 108 | 113 | 102 | 87 | −54 | 1.83E−6 | 4.15E−5 | 9.44E−6 |
| SW-620 | 0.215 | 1.524 | 1.444 | 1.208 | 0.732 | 0.423 | 0.116 | 84 | 83 | 39 | 16 | −46 | 5.71E−7 | 1.80E−5 | >1.00E−4 |
| CNS Cancer | | | | | | | | | | | | | | | |
| SF-268 | 0.336 | 1.237 | 1.294 | 1.215 | 1.179 | 0.859 | 0.235 | 106 | 93 | 94 | 58 | −30 | 1.24E−6 | 4.58E−5 | >1.00E−4 |
| SF-295 | 0.711 | 2.308 | 2.354 | 1.884 | 1.603 | 0.991 | 0.608 | 104 | 80 | 56 | 18 | −15 | 1.43E−6 | 3.52E−5 | >1.00E−4 |
| SF-539 | 0.420 | 1.452 | 1.634 | 1.568 | 1.496 | 0.987 | 0.115 | 108 | 110 | 104 | 55 | −73 | 1.09E−5 | 2.70E−5 | 8.66E−5 |
| SNB-19 | 0.526 | 1.553 | 1.682 | 1.518 | 1.483 | 1.287 | 0.400 | 103 | 97 | 97 | 74 | −24 | 1.76E−5 | 5.89E−5 | >1.00E−4 |
| SNB-75 | 0.540 | 1.132 | 1.223 | 1.227 | 1.193 | 0.846 | 0.171 | 118 | 119 | 112 | 42 | −73 | 7.64E−6 | 2.31E−5 | 6.28E−5 |
| U251 | 0.394 | 1.766 | 1.673 | 1.560 | 1.299 | 0.737 | 0.258 | 93 | 84 | 56 | 25 | −35 | 2.46E−6 | 2.53E−5 | >1.00E−4 |
| Melanoma | | | | | | | | | | | | | | | |
| LOX IMVI | 0.386 | 2.087 | 2.124 | 2.007 | 2.024 | 0.814 | 0.053 | 102 | 95 | 96 | 25 | −86 | 4.48E−8 | 1.68E−5 | 4.72E−5 |
| MALME-3M | 0.517 | 0.731 | 0.742 | 0.760 | 0.704 | 0.592 | 0.217 | 105 | 114 | 88 | 35 | −58 | 5.17E−6 | 2.37E−5 | 8.20E−5 |
| M14 | 0.425 | 1.382 | 1.333 | 1.327 | 1.259 | 0.760 | 0.090 | 95 | 94 | 87 | 35 | −79 | 5.16E−6 | 2.03E−5 | 5.59E−5 |
| SK-MEL-2 | 0.797 | 1.353 | 1.341 | 1.265 | 1.172 | 0.640 | 0.287 | 98 | 84 | 67 | −20 | −64 | 1.58E−6 | 5.94E−8 | 4.82E−5 |
| SK-MEL-28 | 0.204 | 0.794 | 0.754 | 0.780 | 0.762 | 0.690 | 0.113 | 83 | 93 | 93 | 82 | −45 | 1.80E−5 | 4.44E−6 | >1.00E−4 |
| SK-MEL-5 | 0.295 | 1.709 | 1.633 | 1.602 | 1.339 | 0.855 | 0.010 | 95 | 92 | 74 | 40 | −97 | 4.97E−6 | 1.95E−5 | 4.55E−5 |
| UACC-62 | 0.727 | 2.197 | 1.885 | 1.238 | 0.715 | 0.383 | 0.041 | 79 | 35 | −2 | −47 | −94 | 4.51E−8 | 8.97E−7 | 1.14E−5 |
| Ovarian Cancer | | | | | | | | | | | | | | | |
| OVCAR-3 | 0.391 | 1.398 | 1.349 | 1.184 | 0.807 | 0.399 | 0.158 | 95 | 77 | 41 | 1 | −60 | 5.69E−7 | 1.03E−5 | 6.91E−5 |
| OVCAR-4 | 0.411 | 1.180 | 1.135 | 0.958 | 0.553 | 0.487 | 0.294 | 94 | 71 | 31 | 10 | −29 | 3.40E−7 | 1.80E−5 | >1.00E−4 |
| OVCAR-5 | 0.357 | 0.975 | 0.628 | 0.428 | 0.340 | 0.283 | 0.185 | 43 | 10 | −7 | −23 | −50 | <1.00E−8 | 3.72E−7 | >1.00E−4 |
| SK-OV-3 | 0.555 | 1.118 | 1.094 | 1.035 | 0.904 | 0.645 | 0.456 | 96 | 85 | 62 | 16 | −18 | 1.82E−6 | 2.95E−5 | >1.00E−4 |
| Renal Cancer | | | | | | | | | | | | | | | |
| 785-0 | 0.481 | 1.940 | 1.923 | 1.758 | 1.580 | 0.370 | 0.232 | 69 | 88 | 70 | 27 | −52 | 3.40E−6 | 2.19E−5 | 8.47E−5 |
| A498 | 0.926 | 1.892 | 1.394 | 0.408 | 0.120 | 0.048 | 0.058 | 61 | −66 | −87 | −95 | −94 | 1.24E−8 | 3.33E−8 | 8.90E−8 |
| ACHN | 0.489 | 1.601 | 1.589 | 1.516 | 1.323 | 0.668 | 0.345 | 99 | 92 | 76 | 16 | −30 | 2.88E−6 | 2.25E−5 | >1.00E−4 |
| CAK1-1 | 0.428 | 0.901 | 0.431 | 0.416 | 0.337 | 0.226 | 0.433 | 1 | −3 | −21 | −47 | 1 | <1.00E−0 | — | >1.00E−4 |
| RXF 393 | 0.288 | 0.530 | 0.380 | 0.295 | 0.237 | 0.188 | 0.041 | 31 | 7 | −12 | −30 | −85 | <1.00E−8 | 2.44E−7 | 2.32E−5 |
| SN12C | 0.906 | 2.138 | 2.103 | 2.047 | 1.874 | 1.234 | 0.308 | 97 | 93 | 79 | 27 | −66 | 3.56E−6 | 1.94E−5 | 6.72E−5 |
| TK-10 | 0.627 | 1.348 | 1.074 | 0.607 | 0.565 | 0.574 | 0.514 | 62 | −3 | −10 | −8 | −16 | 1.53E−8 | 8.84E−8 | >1.00E−4 |
| UO-31 | 0.507 | 1.373 | 1.290 | 1.200 | 1.026 | 0.594 | 0.292 | 90 | 80 | 50 | 10 | −42 | 1.58E−6 | 1.55E−6 | >1.00E−4 |
| Prostate Cancer | | | | | | | | | | | | | | | |
| DU-145 | 0.211 | 0.836 | 0.885 | 0.888 | 0.821 | 0.475 | 0.100 | 108 | 108 | 98 | 42 | −53 | 7.25E−6 | 2.78E−5 | 9.33E−5 |

TABLE 4A-continued

Oncrasin 27
National Cancer Institute Developmental Therapeutics Program
In-Vitro Testing Results Breast Cancer

| | | | | | | | | | | | | | | | |
|---|---|---|---|---|---|---|---|---|---|---|---|---|---|---|---|
| MCF7 | 0.377 | 2.090 | 1.653 | 1.146 | 0.551 | 0.509 | 0.340 | 75 | 45 | 10 | 8 | −10 | 8.73E−8 | 2.75E−5 | >1.00E−4 |
| NCI/ADR-RES | 0.347 | 1.162 | 1.191 | 1.117 | 1.045 | 0.744 | 0.192 | 103 | 94 | 85 | 48 | −45 | 9.22E−6 | 3.32E−6 | >1.00E−4 |
| MDA-MB-231/ATCC | 0.558 | 1.205 | 1.237 | 1.332 | 1.265 | 0.904 | 0.380 | 105 | 120 | 109 | 55 | −32 | 1.10E−5 | 4.23E−5 | >1.00E−4 |
| HS 578T | 0.425 | 0.995 | 1.023 | 0.984 | 0.945 | 0.595 | 0.283 | 105 | 98 | 91 | 30 | −38 | 4.68E−6 | 2.75E−6 | >1.00E−4 |
| MDA-MB-435 | 0.418 | 1.789 | 1.801 | 1.793 | 1.790 | 1.535 | 0.297 | 102 | 100 | 96 | 81 | −29 | 1.93E−6 | 5.47E−5 | >1.00E−4 |
| BT-549 | 0.426 | 0.794 | 0.831 | 0.655 | 0.782 | 0.524 | 0.066 | 110 | 116 | 97 | 28 | −85 | 4.82E−6 | 1.73E−5 | 4.88E−4 |
| T-47D | 0.537 | 1.284 | 1.079 | 0.884 | 0.474 | 0.459 | 0.485 | 73 | 20 | −12 | −16 | −14 | 2.67E−8 | 4.23E−7 | >1.00E−4 |

TABLE 4B

Oncrasin 27
National Cancer Institute Developmental Therapeutics Program
Mean Graphs

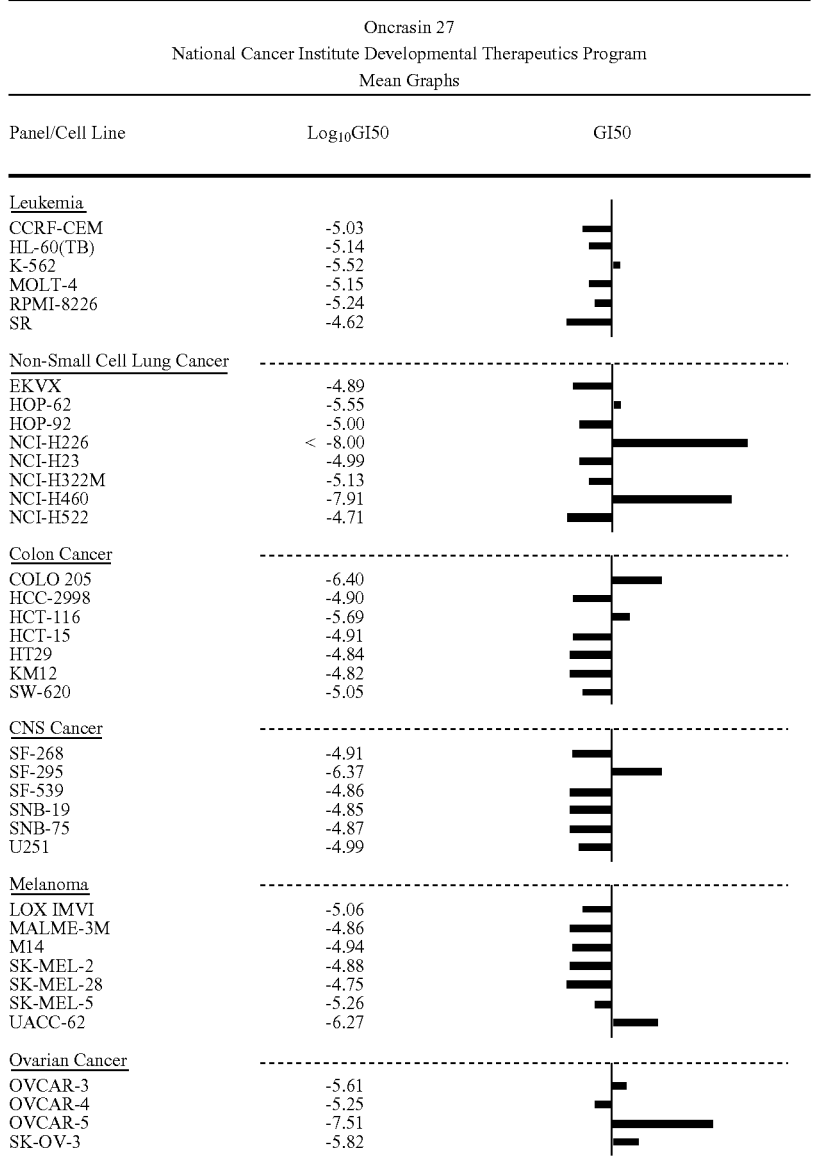

| Panel/Cell Line | $Log_{10}GI50$ | GI50 |
|---|---|---|
| Leukemia | | |
| CCRF-CEM | −5.03 | |
| HL-60(TB) | −5.14 | |
| K-562 | −5.52 | |
| MOLT-4 | −5.15 | |
| RPMI-8226 | −5.24 | |
| SR | −4.62 | |
| Non-Small Cell Lung Cancer | | |
| EKVX | −4.89 | |
| HOP-62 | −5.55 | |
| HOP-92 | −5.00 | |
| NCI-H226 | < −8.00 | |
| NCI-H23 | −4.99 | |
| NCI-H322M | −5.13 | |
| NCI-H460 | −7.91 | |
| NCI-H522 | −4.71 | |
| Colon Cancer | | |
| COLO 205 | −6.40 | |
| HCC-2998 | −4.90 | |
| HCT-116 | −5.69 | |
| HCT-15 | −4.91 | |
| HT29 | −4.84 | |
| KM12 | −4.82 | |
| SW-620 | −5.05 | |
| CNS Cancer | | |
| SF-268 | −4.91 | |
| SF-295 | −6.37 | |
| SF-539 | −4.86 | |
| SNB-19 | −4.85 | |
| SNB-75 | −4.87 | |
| U251 | −4.99 | |
| Melanoma | | |
| LOX IMVI | −5.06 | |
| MALME-3M | −4.86 | |
| M14 | −4.94 | |
| SK-MEL-2 | −4.88 | |
| SK-MEL-28 | −4.75 | |
| SK-MEL-5 | −5.26 | |
| UACC-62 | −6.27 | |
| Ovarian Cancer | | |
| OVCAR-3 | −5.61 | |
| OVCAR-4 | −5.25 | |
| OVCAR-5 | −7.51 | |
| SK-OV-3 | −5.82 | |

TABLE 4B-continued

Oncrasin 27
National Cancer Institute Developmental Therapeutics Program
Mean Graphs

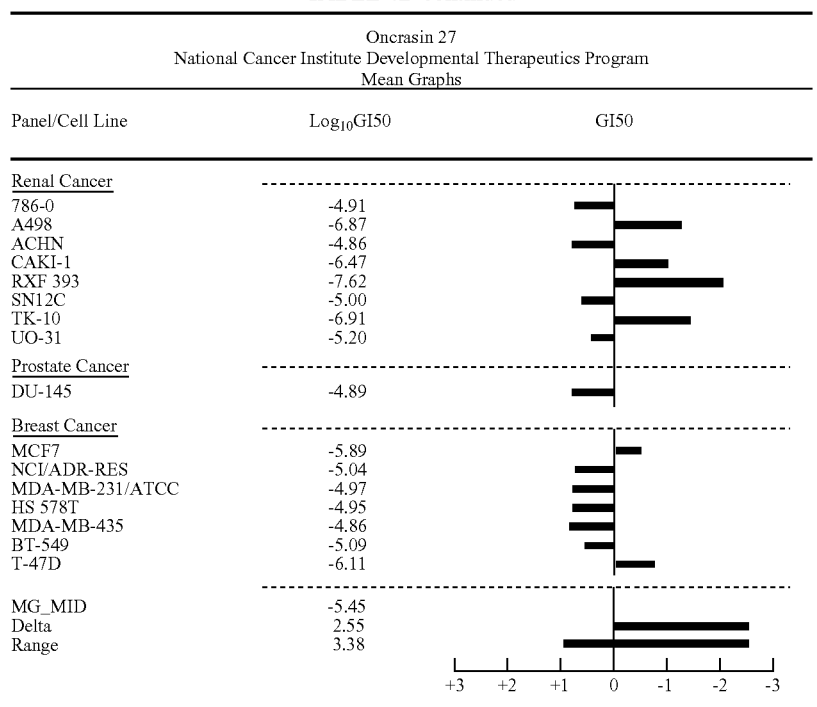

| Panel/Cell Line | Log$_{10}$GI50 | GI50 |
|---|---|---|
| Renal Cancer | | |
| 786-0 | -4.91 | |
| A498 | -6.87 | |
| ACHN | -4.86 | |
| CAKI-1 | -6.47 | |
| RXF 393 | -7.62 | |
| SN12C | -5.00 | |
| TK-10 | -6.91 | |
| UO-31 | -5.20 | |
| Prostate Cancer | | |
| DU-145 | -4.89 | |
| Breast Cancer | | |
| MCF7 | -5.89 | |
| NCI/ADR-RES | -5.04 | |
| MDA-MB-231/ATCC | -4.97 | |
| HS 578T | -4.95 | |
| MDA-MB-435 | -4.86 | |
| BT-549 | -5.09 | |
| T-47D | -6.11 | |
| MG_MID | -5.45 | |
| Delta | 2.55 | |
| Range | 3.38 | |

Example 3

IN VIVO Activity of Oncrasin Compounds

Figure 14A:
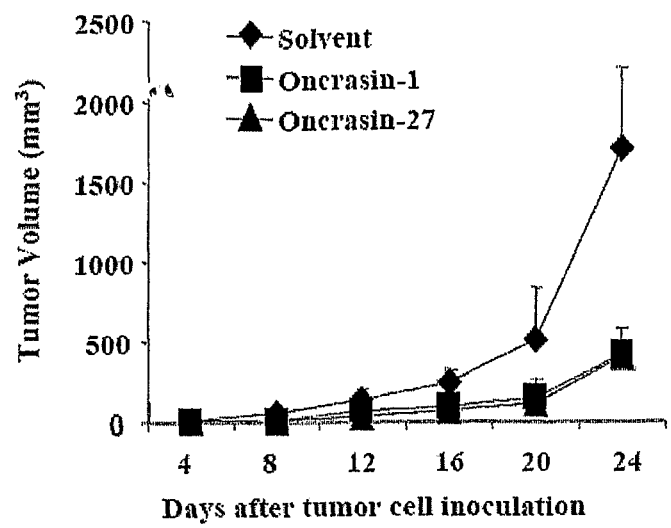
FIGS. 14A and 14B Antitumor activity in vivo.
Figure 14B:
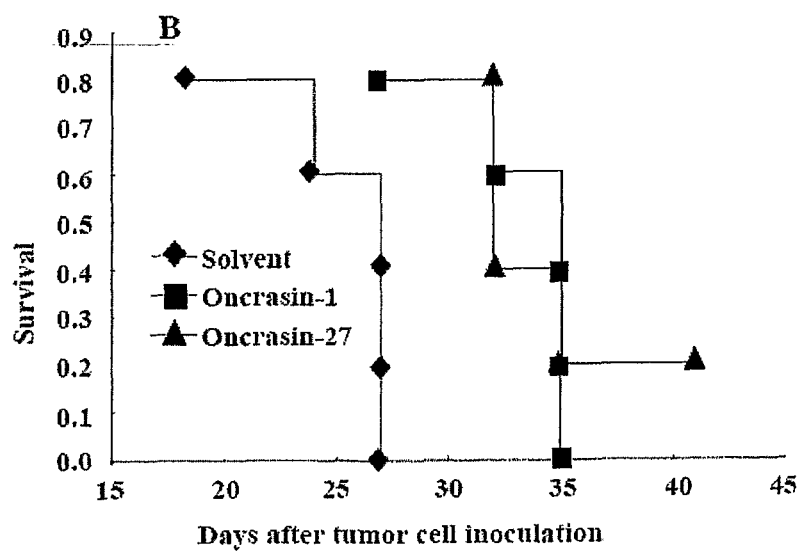
Figure 15A:
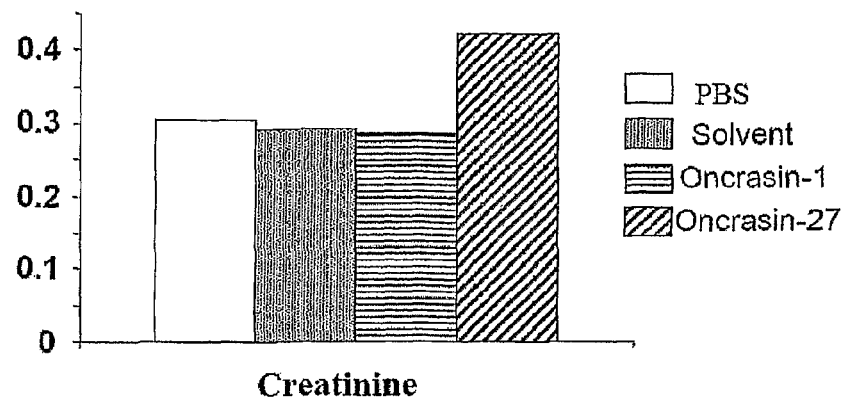
FIGS. 15A and 15B In vivo toxicity assay. The blood was collected from animals described in FIG. 14 at two days after the last treatment and (FIG. 15B) serum ALT, AST and (FIG. 15A) creatinine levels were determined. The values represent mean of three animals.
Figure 15B:
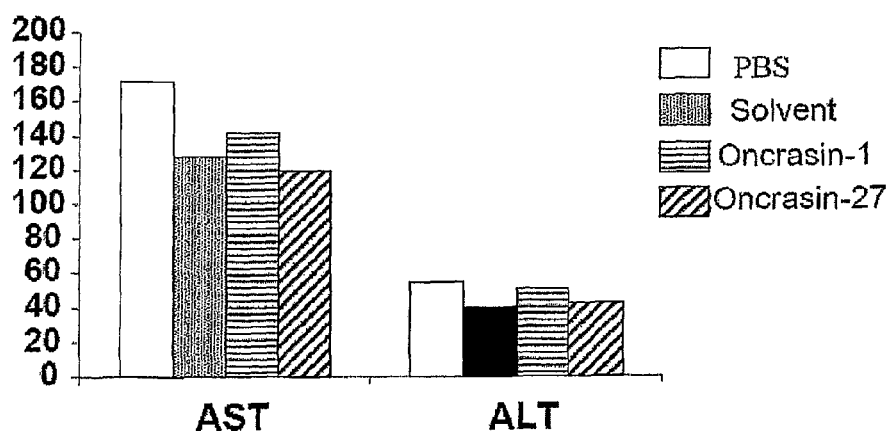

The inventors have investigated the in vivo antitumor activity of Oncrasin compounds, such as Oncrasin-1 and Oncrasin-27, both are available at relatively larger scale. Subcutaneous tumors were established in 4- to 6-week-old female nude mice (Charles River Laboratories Inc., Wilmington, Mass.) by the inoculation of $1.5 \times 10^6$ H460 cells into the dorsal flank of each mouse. After the tumors grew to 5 mm in diameter, mice were treated with intraperitoneal injections of Oncrasin-1 (for 10 days) or Oncrasin-27 (for 3 days, because of limited availability of the compound) at a dose of 100 mg/kg/injection daily (the agents were dissolved in 0.5 mL of solvent containing 10% DMSO, 10% Cremophor EL, and 10% ethanol), or they were given intraperitoneal injections of solvent alone. The tumor volumes were calculated using the formula $a \times b^2 \times 0.5$, where a and b represent the larger and smaller diameters, respectively (Gu et al., 2000; Terashi et al., 2005). Mice were killed when the tumors grew to 1.5 cm in diameter. To evaluate the toxicity of treatment, blood samples were collected from the tail vein before treatment and 2 days after the last treatment, and serum alanine transaminase, aspartate transaminase, and creatinine levels were determined as described elsewhere (Gu et al., 2000; Terashi et al., 2005). Hematopoietic toxicity was monitored by counting red blood cells, white blood cells, and platelets (Gu et al., 2002; Terashi et al., 2005). The lung, heart, liver, intestine, spleen, and kidney were harvested after the mice were killed to test the toxic effects of both compounds on these organs. The histopathologic analysis was performed in the histology laboratory of the Department of Veterinary Medicine and Surgery at M. D. Anderson Cancer Center. The results showed that Oncrasin-1 and Oncrasin-27 significantly suppressed tumor growth. In comparison with solvent, Oncrasin-1 and Oncrasin-27 suppressed growth of tumor volume by 75.4% and 76.3%, respectively (FIG. 14A). The two agents also prolonged survival (FIG. 14B). The mean survivals for mice treated with solvent, Oncrasin-1, and Oncrasin-27 were 24, 32, and 34 days, respectively. No difference was observed in the body weights of mice treated with solvent, Oncrasin-1, or Oncrasin-27. In addition, blood cell counts were the same among the groups, all in the normal ranges. The serum alanine aminotransferase (ALT), aspartate aminotransferase (AST), and creatinine levels were within the normal range in all mice tested, regardless of the treatment received (FIG. 15). Histopathologic examination further showed that there were no significant lesions in any mice or in any organs tested (i.e., the lung, heart, stomach, small intestine, liver, spleen, pancreas, and kidney), suggesting that in vivo antitumor activity can be achieved without observable toxicity. Those data demonstrated that Oncrasin compounds might be useful for the treatment of cancers.

Example 4

Modulation of RNA Processing

Figure 16A:
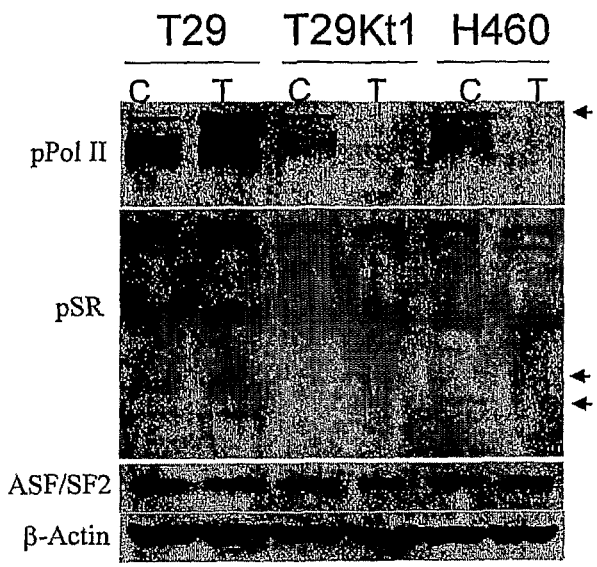
FIGS. 16A and 16B Effect on RNA processing machinary.
Figure 16B:
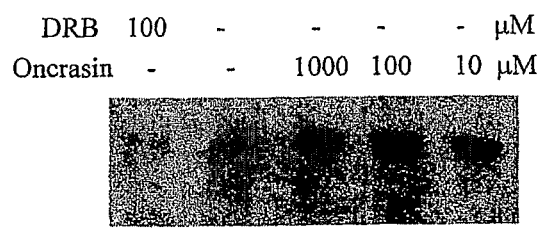

The study on intracellular distribution of SC35 and ASF/SF2 showed that Oncrasin compounds can induce aggregation of the splicing factors, suggesting the Oncrasin may affect RNA processing, either transcription, splicing, or both. To further test the role of RNA transcription and splicing in Oncrasin-mediated antitumor activity the phosphorylation of the largest subunit of RNA polymerase II and splicing factors were analyzed. T29, T29Kt1 and H460 cells were treated with Oncrasin-1 at an optimal concentration, around $IC_{60}$ to $IC_{80}$ for T29Kt1 and H460 cells. Cell lysates were collected 12 h after the treatment and subjected to Western blot analysis with antibodies specific for phosphorylated RNA polymerase If (H5, Covance Research Products, Inc., Berkeley, Calif.) and SR proteins (1H4, Zymed, obtained from Invitrogen, Carlsbad, Calif.). The result showed that treatment with Oncrasin-1 led to a dramatic suppression of phosphorylated RNA polymerase II and certain SR proteins (See FIG. 16A), demonstrating that treatment with Oncrasin indeed disrupts RNA processing. Interestingly, however, in vitro transcription assay with HeLa nuclear extracts (Promega, Madison, Wis.) showed that, unlike the RNA polymerase II inhibitor 5,6-dichloro-1-β-D ribofuranosylbenzimidazole (DRB) (Chodosh et al., 1989; Zandomeni et al., 1984). Oncrasin-1 does not inhibit in vitro RNA transcription directly (FIG. 16B), suggesting that the effect on RNA polymerase II phosphorylation could be indirect.

The serine-arginine rich (SR) proteins constitute a family of about a dozen polypeptides, including SC35 and ASF/SF2, that are essential for both the operational and regulation of splicing. Specific phosphorylation of SR proteins is one of the key determinants regulating splicing events. Several kinases involved in SR protein phosphorylation have been identified and characterized, including SR protein kinases SRPK-1 and SRPK-2 (Wang et al., 1998), CLK/STY (Colwill et al., 1996), and DNA topoisomerase I (Rossi et al., 1996). It was reported that both hyper- and hypophosphorylation inhibited SR protein splicing activity (Prasad et al., 1999). More recently, it was reported that a SRPK inhibitor can effectively inhibit HIV production and propagation (Fukuhara et al., 2006).

The C-terminal domain (CTD) of the largest subunit of eukaryotic RNA polymerase II contains multiple heptapeptide repeats of the sequence YSPTSPS, 26 in yeast CTD and 52 in mammalian CTD (Oelgeschlager and Oelgeschlager, 2002). The serine and threonine in the CTD are variably phosphorylated, which leads to the production of two forms of RNA polymerase II in vivo: a hypophosphorylated form called IIa, and a hyperphosphorylated form called IIo. Three major cyclin-dependent protein kinases CDK7/cyclin H (TFIIH) (Iarochelle et al., 2001; Shiekhattar et al., 1995), CDK8/cyclin C (Akoulitchev et al., 2000; Leclerc et al., 2000) and CDK9/cyclin T (P-TEFb) (Kim et al., 2002) are known to phosphorylate CTD. In addition to the CDKs, there are other protein kinases that also efficiently phosphorylate CTD, including the DNA-dependent protein kinase (DNA-PK) (Peterson et al., 1995), the extracellular regulated kinase (ERK) (Bonnet et al., 1999), and the c-abl tyrosine kinase (Baskaran et al., 1996; Baskaran et al., 1993). Phosphorylation of the CTD is required for efficient transcription elongation, and recruitment of mRNA processing factors, including capping enzyme and splicing factors required for efficient processing of RNA transcripts (McCracken et al., 1997; Misteli et al., 1999; Mortillaro et al., 1996). Pol II enters into the assembling transcription complex with its CTD unphosphorylated (IIa form). Phosphorylation of the CTD by CDK7 and CDK9 convert Pol II to IIo form, enabling efficient RNA elongation and processing (McCracken et al., 1997; Misteli et al., 1999). At the end of the transcription cycle, the polymerase II is dephosphorylated by the phosphatase FCP1 (Kamenski et al., 2004; Achamubault et al., 1997). FCP1 is required for the regeneration of initiation-competent RNA polymerase II and may also antagonize the action of CDK8, which inhibits transcription by phosphorylation of the polymerase 1 prior to its recruitment to the preinitiation complex (Hengartner et al., 1998).

Evidence also indicated that transformed cells require continuous activity of RNA polymerase II to resist oncogene-induced apoptosis (Koumenis et al., 1997). Inhibition of the polymerase II in untransformed cells resulted in growth arrest but not apoptosis. In contrast, transforming cells with c-Myc dramatically increased sensitivity to 5,6-dichloro-1-β-D ribofuranosylbenzimidazole (DRB), indicating that apoptosis following inhibition of RNA polymerase II function is greatly enhanced by oncogenic expression. The phosphorylation of CTD also plays roles in replication of HIV (Wei et al., 1998) and hepatitis delta virus (Yamaguchi et al., 2001). Recent studies have indicated that human CDK7 and CDK9 are recruited to the HIV-1 promoter through a cis-acting element called transactivation response (TAR) on the nascent transcript by Tat, the human immunodeficiency virus 1 (HIV-1) transactivator protein, and hyperphosphorylates the CTD. Tat binds to the TAR RNA stem-loop in the viral long terminal repeat (LTR) and increases rates of elongation of transcription by RNA polymerase II (Pol II) (Kim et al., 2002; Cujec et al., 1997). RNA polymerase II inhibitors, such as (DRB) (Chodosh et al., 1989; Zandomeni et al., 1984), inhibit the production of long transcripts from the HIV LTR in vitro and in vivo (Critchfield et al., 1997; Marciniak et al., 1991), although basal transcription and the production of short transcripts from the HIV LTR is independent of the CTD.

Together, the phosphorylation inhibition of RNA polymerase II and SR protein by Oncrasin compounds indicate that they could be useful for treatment cancer and/or certain viral diseases, such as ADS and hepatitis D.

REFERENCES

The following references, to the extent that they provide exemplary procedural or other details supplementary to those set forth herein, are specifically incorporated herein by reference.

U.S. Pat. No. 4,837,028
U.S. Pat. No. 4,186,183
U.S. Pat. No. 4,217,344
U.S. Pat. No. 4,235,871
U.S. Pat. No. 4,261,975
U.S. Pat. No. 4,485,054
U.S. Pat. No. 4,501,728
U.S. Pat. No. 4,603,044
U.S. Pat. No. 4,737,323
U.S. Pat. No. 4,946,787
U.S. Pat. No. 4,957,773
U.S. Pat. No. 5,795,587
U.S. Pat. No. 5,145,684
U.S. Pat. No. 5,399,363
U.S. Pat. No. 5,466,468
U.S. Pat. No. 5,534,499
U.S. Pat. No. 5,543,158
U.S. Pat. No. 5,552,157
U.S. Pat. No. 5,565,213
U.S. Pat. No. 5,567,434
U.S. Pat. No. 5,580,579
U.S. Pat. No. 5,641,515
U.S. Pat. No. 5,641,515
U.S. Pat. No. 5,725,871
U.S. Pat. No. 5,738,868
U.S. Pat. No. 5,741,516
U.S. Pat. No. 5,756,353
U.S. Pat. No. 5,780,045
U.S. Pat. No. 5,792,451
U.S. Pat. No. 5,804,212
U.S. Pat. No. 5,820,873
U.S. Pat. No. 5,885,613
U.S. Pat. No. 5,976,567
U.S. Pat. No. 6,027,726
U.S. Pat. No. 6,320,017
U.S. Prov. Appln. 60/571,712
Abra et al., *J. Liposome Res.*, 12:1-3, 2002.
Akoulitchev et al., *Nature*, 407:102-106, 2000.
Alessi et al., *Current Biology*, 7:776-789, 1997.

Algarra et al., *Invasion and Metastasis*, 18: 261-270, 1998.
Allen and Chonn, *FEBS Lett.*, 223(1):42-46, 1987.
Allen et al., *Biochim Biophys Acta*, 1237(2):99-108, 1995.
Archambault et al., *Proc. Natl. Acad. Sci. USA*, 94:14300-14305, 1997.
Barenholz, In: *Physiology of Membrane Fluidity*, Shinitsky (Ed.), CRC Press, FL. (1):131-174, 1984.
Barnes et al., *NE J. Medicine*, 336:1066-1071, 1997.
Bar-Sagi and Hall, *STKE*, RE13, 2004.
Baskaran et al., *Molec. Cell. Biol.*, 16:3361-3369, 1996.
Baskaran et al., *Proc. Natl: Acad. Sci. USA*, 90:11167-11171, 1993.
Baum and Kirschmeier, *Current Oncology Reports*, 5:99-107, 2003.
Baumann et al., *Cell*, 87:757-766, 1996.
Benson et al., *EMBO J.*, 13:5764-5771, 1994.
Bergo et al., *J. Clinical Investigation*, 113:539-550, 2004.
Bernards and Settleman, *Trends in Cell Biology*, 14:377-385, 2004.
Bernhard et al., *Cancer Res.*, 60: 6597-6600, 2000.
Berra et al., *Cell*, 74:555-563, 1993.
Bloomfield, *Ann. Rev. Biophys. Bioeng.*, 10:421-450, 1981.
Blume et al., *Biochim Biophys Acta*, 1146(2):157-168, 1993.
Bonnet et al., *Nucleic Acids Research*, 27:4399-4404, 1999.
Bos et al., *Nature*, 327: 293-297, 1987.
Bos, *Cancer Res.*, 49: 4682-4689, 1989.
Brignall, *Alternative Medicine Review*, 6: 580-589, 2001.
Cadwallader et al., *Molecular and Cellular Biology*, 14: 4722-4730, 1994.
Carmo-Fonseca et al., *J. Cell Biology*, 117: 1-14, 1992.
Chandran et al., *Indian J. Exp. Biol*, 35(8):801-809., 1997.
Chinni et al., *Oncogene*, 20: 2927-2936, 2001.
Chodosh et al., *J. Biological Chemistry*, 264: 2250-2257, 1989.
Coleman et al., *Carcinogenesis*, 15: 1005-1012, 1994.
Colwill et al., *EMBO J*, 15: 265-275, 1996.
Couvreur et al., *FEBS Lett.*, 84(2):323-326, 1977.
Couvreur, *Crit. Rev. Ther. Drug Carrier Syst.*, 5(1):1-20, 1988.
Critchfield et al., *Proc. Natl. Acad. Sci. USA*, 94: 6110-6115, 1997.
Cujec et al., *Genes and Development*, 11: 2645-2657, 1997.
Davies et al., *Nature*, 417: 949-954, 2002.
Deamer and Bangham, *Biochim. Biophys. Acta*, 443:629-634, 1976.
Diaz-Meco et al., *J. Biological Chemistry*, 269: 31706-31710, 1994.
Eder et al., *Proc. Natl. Acad. Sci. USA*, 102: 12519-12524, 2005.
Ehrhardt et al., *Molecular & Cellular Biology*, 24: 6311-6323, 2004.
Fakan et al., *Experimental Cell Research*, 113: 327-337, 1978.
Fedorov et al., *Molecular and Cellular Biology*, 22: 1140-1149, 2002.
Filmus et al., *Cancer Res.*, 45: 4468-4472, 1985.
Fiorucci and Hall, *Biochimica et Biophysica Acta*, 950: 81-83, 1988.
Fisher, *Cell*, 78: 539-42, 1994.
Fraley et al., *Proc. Natl. Acad. Sci. USA*, 76:3348-3352, 1979.
Fu et al., *Science*, 256: 535-538, 1992.
Fukuhara et al., *Proc. Natl. Acad. Sci. USA*, 103: 11329-11333, 2006.
Gabizon and Papahadjopoulos, *Proc. Natl. Acad. Sci. USA*, 85(18):6949-6953, 1988.
Galiana et al., *Molecular Carcinogenesis*, 14: 286-293, 1995.
Garnett and Marais, *Cancer Cell*, 6: 313-319, 2004.
Gu et al., *Cancer Res.*, 60: 5359-5364, 2000.
Gu et al., *Gene Ther.*, 9: 30-37, 2002.
Guerrero et al., *Cancer Res.*, 60: 6750-6756, 2000.
Hancock et al., *Cell*, 63: 133-139, 1990.
Hancock, *Nature Reviews Molecular Cell Biology*, 4: 373-384, 2003.
Heath, In: *Methods in Enzymology*, (149):111-119, Academic Press, Inc. 1987.
Hengartner et al., *Molecular Cell*, 2: 43-53, 1998.
Hirahata et al., *Gan To Kagaku Ryoho.*, 19(10 Suppl):1591-1594, 1992.
Hoa et al., *Cancer Res.*, 62: 7154-7156, 2002.
Hope et al., *Biochim. Biophys. Acta*, 812:55-65, 1985.
Hope et al., *Chem. Phys. Lip.*, 40:89, 1986.
Hwang et al., *Crit. Rev. Ther. Drug Carrier Syst.*, 15(3):243-284, 1998.
James et al., *J. Biological Chemistry*, 270: 6221-6226, 1995.
James et al., *Proc. Natl. Acad. Sci. USA*, 93: 4454-4458, 1996.
Jun et al., *Science's STKE [Electronic Resource]: Signal Transduction Knowledge Environment*, 1999: E1, 1999.
Kaelin, *Nature Reviews Cancer*, 5: 689-698, 2005.
Kamenski et al., *Molecular Cell*, 15: 399-407, 2004.
Karin and Ben Neriah, *Annual Review of Immunology*, 18: 621-663, 2000.
Karin and Karin, *Nature*, 441: 431-436, 2006.
Karin et al., *Nature Reviews, Drug Discovery.* 3: 17-26, 2004.
Kelloff et al., *Journal of Cellular Biochemistry*—Supplement, 26: 1-28, 1996.
Kim et al., *Molecular and Cellular Biology*, 22: 4622-4637, 2002.
Klibanov et al., *Ann. NY Acad. Sci.*, 672, 1992.
Koumenis et al., *Molecular and Cellular Biology*, 17: 7306-7316, 1997.
Krainer et al., *Cell*, 66: 383-394, 1991.
Larochelle et al., *EMBO Journal*, 20: 3749-3759, 2001.
Lasic, *Trends Biotechnol.*, 16(7):307-321, 1998.
Le Good et al., *Science*, 281: 2042-2045, 1998.
Leclerc et al., *Molecular Biology of the Cell*, 7: 505-513, 1996.
Leonetti et al., *Proc. Natl. Acad. Sci. USA*, 87:2448-2451, 1990.
Liu et al., *Cancer Res.*, 64: 1655-1663, 2004.
Marciniak et al., *EMBO Journal*, 10: 4189-4196, 1991.
Mathiowitz et al., *Nature*, 386(6623):410-414, 1997.
Mayer et al., *Biochim. Biophys. Acta*, 858:161-168, 1986.
McCracken et al., *Nature*, 385: 357-361, 1997.
Mills et al., *Cancer Res.*, 55: 1444-1447, 1995.
Misteli et al., *Molecular Cell*, 3: 697-705, 1999.
Misteli et al., *Nature*, 387: 523-527, 1997.
Morishita et al., *Proc. Natl. Acad. Sci. USA*, 90:8474, 1993.
Mortillaro et al., *Proc. Natl. Acad. Sci. U.S.A.*, 93: 8253-8257, 1996.
Murray et al., *Journal of Cell Biology*, 164: 797-802, 2004.
Nakanishi et al., *Journal of Biological Chemistry*, 268: 13-16, 1993.
Nemunaitis et al., *American Journal of Clinical Oncology*, 20: 527-529, 1997.
Neri et al., *FASEB Journal*, 13: 2299-2310, 1999.
Oelgeschlager and Oelgeschlager, *Journal of Cellular Physiology*, 190: 160-169, 2002.
O'Keefe et al., *Journal of Cell Biology*, 124: 249-260, 1994.
Oltvai et al., *Cell*, 74: 609-19, 1993.
O'Neill et al., *Science*, 306: 2267-2270, 2004.
Ostro, In: *Liposomes*, Marcel Dekker, Inc., Chap. 1, NY, 1983.
Pacold et al., *Cell*, 103: 931-943, 2000.

Papaldo et al., *Journal of Clinical Oncology*, 21: 3462-3468, 2003.
PCT Appln. WO 91/17424
Pellegata et al., *Cancer Res.*, 54: 1556-1560, 1994.
Pells et al., *Oncogene*, 15: 1781-1786, 1997.
Perander et al., *Journal of Biological Chemistry*, 276: 13015-13024, 2001.
Peterson et al., *Journal of Biological Chemistry*, 270: 1449-1454, 1995.
Pinto-alphandary et al., *J. Drug Target*, 3(2):167-169, 1995.
Prasad et al., *Molecular and Cellular Biology*, 19: 6991-7000, 1999.
Pullen et al., *Science*, 279: 707-710, 1998.
Quintanar-Guerrero et al., *Pharm. Res.*, 15(7):1056-1062, 1998.
Ravagnan et al., *Oncogene*, 18: 2537-2546, 1999.
Regala et al., *Cancer Res.*, 65: 8905-8911, 2005.
Remington's Pharmaceutical Sciences" 15th Edition, pages 1035-1038 and 1570-1580, 1990.
Remington's Pharmaceutical Sciences, 1035-1038 and 1570-1580
Remington's Pharmaceutical Sciences, 18th Ed. Mack Printing Company, pp. 1289-1329, 1990.
Renneisen et al., *J. Bio. Chem.*, 265:16337-16342, 1990.
Rodriguez-Viciana et al., *Nature*, 370: 527-532, 1994.
Rossi et al., *Nature*, 381: 80-82, 1996.
Rossman et al., *Nature Reviews Molecular Cell Biology*, 6: 167-180, 2005.
Rowley and Van Ness, *Oncogene*, 21: 8769-8775, 2002.
Rubinstein et al., *Journal of the National Cancer Institute*, 82: 1113-1118, 1990.
Sapra and Allen, *Prog. Lipid Res.*, 42(5):439-462, 2003.
Sebti and Adjei, *Seminars in Oncology*, 31: 28-39, 2004.
Shiekhattar et al., *Nature*, 374: 283-287, 1995.
Spector and Spector, *Annual Review of Cell Biology*, 9: 265-315, 1993.
Stephens et al., *Science*, 279: 710-714, 1998.
Sun et al., *Clinical Cancer Research*, 8: 3100-3104, 2002.
Szoka et al., *Ann. Rev. Biophys. Bioeng.*, 9:467, 1980.
Takakura, *Nippon Rinsho.*, 56(3):691-695, 1998.
Takenaga et al., *J. Control Release*, 52(1-2):81-87, 1998.
Taylor et al., *Cancer Res.*, 60: 6607-6610, 2000.
Teraishi et al., *Journal of Pharmacology and Experimental Therapeutics*, 314: 355-362, 2005.
Thompson, *Science*, 267: 1456-62, 1995.
Torchilin et al., In: *Liposomes: A Practical Approach*, Oxford University Press, 2003.
Vellard et al., *Proc. Natl. Acad. Sci. U.S.A.*, 89: 2511-2515, 1992.
Vivanco and Sawyers, *Nature Reviews, Cancer.* 2: 489-501, 2002.
Vlahos et al., *Journal of Biological Chemistry*, 269: 5241-5248, 1994.
Vogelstein et al., *New England Journal of Medicine*, 319: 525-532, 1988.
von Gise et al., *Molecular and Cellular Biology*, 21: 2324-2336, 2001.
Wang et al., *Cell*, 87: 629-638, 1996.
Wang et al., *Journal of Cell Biology*, 140: 737-750, 1998.
Wei et al., *Cell*, 92: 451-462, 1998.
Wellbrock et al., *Nature Reviews Molecular Cell Biology*, 5: 875-885, 2004.
White et al., *Journal of Cellular Biochemistry*, 85: 42-53, 2002.
Whyte et al., *Journal of Biological Chemistry*, 272: 14459-14464, 1997.
Williams et al., *Proc. Natl. Acad. Sci. USA*, 85:242-246, 1988.
Winter-Vann et al., *Proc. Natl. Acad. Sci. U.S.A.*, 102: 4336-4341, 2005.
Woodle, *Proc. Natl. Acad. Sci. USA*, 88(24):11460-11464, 1991.
Wu et al., *Cancer Res.*, 64: 1110-1113, 2003.
Yamaguchi et al., *Science*, 293: 124-127, 2001.
Yamamoto et al., *Journal of Biological Chemistry*, 274: 27307-27314, 1999.
Yin et al., *Nature*, 396: 77-80, 1998.
Zalipsky et al., *FEBS Lett.*, 353(1):71-74, 1994.
Zalipsky, *Bioconjug Chem.*, 4(4):296-299, 1993.
Zalipsky, *Bioconjug Chem.*, 6(6):705-708, 1995.
Zambaux et al., *J. Control Release*, 50(1-3):31-40, 1998.
Zandomeni et al., *Journal of Biological Chemistry*, 259: 14804-14811, 1984.
Zeng et al., *EMBO Journal*, 16: 1401-1412, 1997.
Zhang et al., *Cancer Res.*, 66: 4627-4635, 2006.
Zhang et al., *Science*, 290: 989-992, 2000.
Zhu et al., *Current Opinion in Investigational Drugs*, 4: 1428-1435, 2003.
Zhu et al., *Oncogene*, 23: 4984-4992, 2004.
Zhu et al., *Oncogene*, 24: 4993-4999, 2005.
zur Muhlen et al., *Eur. J. Pharm. Biopharm.*, 45(2):149-155, 1998.

The invention claimed is:

1. A method of inhibiting activity of a Ras protein comprising contacting a cell expressing elevated levels of Ras protein or expressing a mutant Ras protein with a compound, or a salt thereof, in an amount sufficient to inhibit the activity of the mutant Ras protein, wherein the compound has a formula:

wherein:

$R_1$ is halo, hydrogen, carboxymethyl, carboxyethyl, carboxypropyl, or carboxybutyl;
$R_2$ is methanol, —C(O)H, —OC(O)CH$_3$, or amino;
$R_3$ is halo or hydrogen;
$R_4$ is halo or hydrogen;
$R_5$ is halo or hydrogen;
$R_6$ is halo or hydrogen;
$R_7$ is halo or hydrogen;
$R_8$ is halo, hydrogen, —CF$_3$, —NO$_2$, or —CH$_3$;
$R_9$ is halo, hydrogen, —CF$_3$, —NO$_2$, or —CH$_3$;
$R_{10}$ is halo, hydrogen, —CF$_3$, —NO$_2$, or —CH$_3$; and
$R_{11}$ is halo, hydrogen, —CF$_3$, —NO$_2$, or —CH$_3$.

2. The method of claim 1, where $R_1$ is a halo group.
3. The method of claim 2, where $R_1$ is a chloro or bromo group.
4. The method of claim 1, where $R_2$ is methanol or —C(O)H.
5. The method of claim 1, where $R_9$ is a chloro group.
6. The method of claim 4, wherein $R_9$ is a bromo group.
7. The method of claim 1, where $R_3$ is a halo group.
8. The method of claim 1, where $R_4$ is halo.
9. The method of claim 1, wherein $R_7$ is chloro or bromo group.

10. The method of claim 1, wherein $R_8$ is chloro or bromo group.

11. The method of claim 1, where $R_9$ is a chloro or bromo group.

12. The method of claim 1, wherein $R_{10}$ is a chloro or bromo group.

13. The method of claim 1, wherein $R_{11}$ is chloro group.

14. The method of claim 1, wherein $R_2$ is methanol.

15. The method of claim 4, wherein $R_2$ is —C(O)H.

16. The method of claim 4, wherein $R_9$ is —CH$_3$.

17. The method of claim 1, wherein $R_8$, $R_9$, or $R_{10}$ is —CF$_3$.

18. The method of claim 1, wherein $R_8$, $R_9$, or $R_{10}$ is —NO$_2$.

19. The method of claim 1, wherein $R_3$, $R_4$, $R_5$, and $R_6$ are hydrogen.

20. The method of claim 1, wherein $R_1$ is hydrogen.

21. The method of claim 1, wherein $R_7$ and $R_9$ are —Cl.

22. The method of claim 1, wherein $R_8$ and $R_9$ are —Cl.

23. The method of claim 11, wherein $R_7$, $R_8$, $R_{10}$, and $R_{11}$ are hydrogen.

24. The method of claim 1, wherein the compound is 1-[(4-chlorophenyl)methyl]-1H-indole-3-carboxaldehyde (Oncrasin 1), 1-(3-chlorobenzyl)-1H-indole-3-carbaldehyde (Oncrasin 27), 1-(4-bromobenzyl)-1H-indole-3-carbaldehyde (Oncrasin 29), [1-(3,4-dichlorobenzyl)-1H-indole-3-yl]methanol (Oncrasin 49), [1-(2-fluorobenzyl)-1H-indole-3-carbaldehyde (Oncrasin 51), 1-[(4-chlorophenyl)methyl]-1H-indole-3-methanol (Oncrasin 60), (1-[3-(trifluoromethyl)benzyl]-1H-indole-3-yl)methanol (Oncrasin 63), 1-(3-nitrobenzyl)-1H-indole-3-carbaldehyde (Oncrasin 68), 1-[(3-nitrophenyl)methyl]-1H-indole-3-methanol (Oncrasin 69), 1-[(4-nitrophenyl)methyl]-1H-indole-3-methanol (Oncrasin 71), 1-[(3-chlorophenyl)methyl]-1H-indole-3-methanol (Oncrasin 72), or 1-[(4-bromophenyl)methyl]-1H-indole-3-methanol (Oncrasin 73).

25. The method of claim 24, wherein the compound is 1-[(4-chlorophenyl)methyl]-1H-indole-3-carboxaldehyde (Oncrasin 1), 1-(3-chlorobenzyl)-1H-indole-3-carbaldehyde (Oncrasin 27), 1-[(4-chlorophenyl)methyl]-1H-indole-3-methanol (Oncrasin 60), or 1-[(3-chlorophenyl)methyl]-1H-indole-3-methanol (Oncrasin 72).

26. The method of claim 1, wherein the mutant Ras protein is a mutant K-Ras protein.

27. The method of claim 26, wherein the K-Ras is mutated at amino acid glycine 12, glycine 13, glutamine 61, or a combination thereof.

28. The method of claim 1, wherein the cell is cancer cell.

29. The method of claim 28, wherein the cancer cell is a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell.

30. The method of claim 28, wherein the cancer cell is in a human.

31. The method of claim 16, further comprising administering a second anticancer therapy.

32. The method of claim 31, wherein the second anticancer therapy is surgery, chemotherapy, radiation therapy, or immunotherapy.

33. A method of treating cancer comprising administering a compound cytotoxic to a cancer cell in a subject in an amount sufficient to induce apoptosis or inhibit growth of the cancer cell; wherein the cytotoxic compound, or a salt thereof is a compound having the formula:

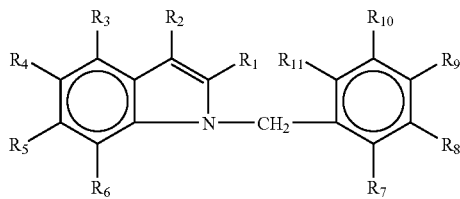

wherein:
$R_1$ is halo, hydrogen, carboxymethyl, carboxyethyl, carboxypropyl, or carboxybutyl;
$R_2$ is methanol, —C(O)H, —OC(O)CH$_3$, or amino;
$R_3$ is halo or hydrogen;
$R_4$ is halo or hydrogen;
$R_5$ is halo or hydrogen;
$R_6$ is halo or hydrogen;
$R_7$ is halo or hydrogen;
$R_8$ is halo, hydrogen, —CF$_3$, —NO$_2$, or —CH$_3$;
$R_9$ is halo, hydrogen, —CF$_3$, —NO$_2$, or —CH$_3$;
$R_{10}$ is halo, hydrogen, —CF$_3$, —NO$_2$, or —CH$_3$; and
$R_{11}$ is halo, hydrogen, —CF$_3$, —NO$_2$, or —CH$_3$.

34. The method of claim 33, wherein the subject is a human.

35. The method of claim 33, wherein $R_2$ is —C(O)H.

36. The method of claim 33, where $R_8$ or $R_9$ is a halo group.

37. The method of claim 36, where $R_9$ is —Cl or —Br.

38. The method of claim 36, where $R_9$ is —Cl.

39. The method of claim 33, wherein $R_7$, $R_8$, $R_{10}$, and $R_{11}$ are hydrogen.

40. The method of claim 33, wherein $R_3$, $R_4$, $R_5$, and $R_6$ are hydrogen.

41. The method of claim 33, wherein $R_7$ is chloro or bromo group.

42. The method of claim 33, where $R_8$ is chloro or bromo group.

43. The method of claim 33, wherein $R_8$, $R_9$, or $R_{10}$ is —CF$_3$.

44. The method of claim 33, wherein $R_8$, $R_9$, or $R_{10}$ is —NO$_2$.

45. The method of claim 33, wherein $R_1$ is hydrogen.

46. The method of claim 33, wherein $R_7$ and $R_9$ are —Cl.

47. The method of claim 33, wherein $R_8$ and $R_9$ are —Cl.

48. The method of claim 33, wherein the compound is 1-[(4-chlorophenyl)methyl]-1H-indole-3-carboxaldehyde (Oncrasin 1), 1-(3-chlorobenzyl)-1H-indole-3-carbaldehyde (Oncrasin 27), 1-(4-bromobenzyl)-1H-indole-3-carbaldehyde (Oncrasin 29), [1-(3,4-dichlorobenzyl)-1H-indole-3-yl]methanol (Oncrasin 49), [1-(2-fluorobenzyl)-1H-indole-3-carbaldehyde (Oncrasin 51), 1-[(4-chlorophenyl)methyl]-1H-indole-3-methanol (Oncrasin 60), (1-[3-(trifluoromethyl)benzyl]-1H-indole-3-yl)methanol (Oncrasin 63), 1-(3-nitrobenzyl)-1H-indole-3-carbaldehyde (Oncrasin 68), 1-[(3-nitrophenyl)methyl]-1H-indole-3-methanol (Oncrasin 69), 1-[(4-nitrophenyl)methyl]-1H-indole-3-methanol (Oncrasin 71), 1-[(3-chlorophenyl)methyl]-1H-indole-3-methanol (Oncrasin 72), or 1-[(4-bromophenyl)methyl]-1H-indole-3-methanol (Oncrasin 73).

49. The method of claim 33, wherein the cancer is a cancer of the bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus.

50. The method of claim 33, further comprising administering a second anticancer therapy.

51. The method of claim 50, wherein the second anticancer therapy is surgery, chemotherapy, radiation therapy, or immunotherapy.

52. The method of claim 45, wherein the compound is 1-[(4-chlorophenyl)methyl]-1H-indole-3-carboxaldehyde (Oncrasin 1), 1-(3-chlorobenzyl)-1H-indole-3-carbaldehyde (Oncrasin 27), 1-[(4-chlorophenyl)methyl]-1H-indole-3-methanol (Oncrasin 60), or 1-[(3-chlorophenyl)methyl]-1H-indole-3-methanol (Oncrasin 72).

* * * * *

UNITED STATES PATENT AND TRADEMARK OFFICE
CERTIFICATE OF CORRECTION

PATENT NO. : 8,883,841 B2  
APPLICATION NO. : 12/094739  
DATED : November 11, 2014  
INVENTOR(S) : Bingliang Fang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,136 days.

Item (60) Related U.S. Application Data, delete "60/739,856" and insert --60/739,865-- therefor.

In the Claims:

In claim 35, column 80, line 27, after "is", insert --methanol or--.

In claim 38, column 80, line 30, delete "claim 36" and insert --claim 37-- therefor.

Signed and Sealed this
Twenty-fifth Day of August, 2015

Michelle K. Lee
*Director of the United States Patent and Trademark Office*